US 008815847B2

(12) United States Patent
Freddo

(10) Patent No.: US 8,815,847 B2
(45) Date of Patent: Aug. 26, 2014

(54) [1,2,4]THIADIAZINE 1,1-DIOXIDE COMPOUNDS FOR LOWERING SERUM URIC ACID

(75) Inventor: James L. Freddo, Del Mar, CA (US)

(73) Assignee: Anadys Pharmaceuticals, Inc., South San Francisco, CA (US)

( * ) Notice: Subject to any disclaimer, the term of this patent is extended or adjusted under 35 U.S.C. 154(b) by 39 days.

(21) Appl. No.: 13/490,046

(22) Filed: Jun. 6, 2012

(65) Prior Publication Data

US 2012/0316156 A1 Dec. 13, 2012

Related U.S. Application Data

(60) Provisional application No. 61/494,288, filed on Jun. 7, 2011.

(51) Int. Cl.
*A61K 31/54* (2006.01)

(52) U.S. Cl.
USPC .............. 514/223.2; 514/222.8; 514/223.5

(58) Field of Classification Search
USPC ........... 514/222.2, 222.5, 222.8, 223.2, 223.5
See application file for complete search history.

(56) References Cited

U.S. PATENT DOCUMENTS

| | | | |
|---|---|---|---|
| 3,969,518 A | 7/1976 | Novello | |
| 7,939,524 B2 | 5/2011 | Tran et al. | |
| 8,097,613 B2 * | 1/2012 | Ruebsam et al. | 514/222.8 |
| 8,101,800 B2 | 1/2012 | Tran et al. | |
| 8,236,948 B2 | 8/2012 | Tran et al. | |
| 2012/0302744 A1 | 11/2012 | Tran et al. | |

FOREIGN PATENT DOCUMENTS

| | | | | |
|---|---|---|---|---|
| WO | WO2008124450 A1 * | 10/2008 | ............ | A01N 46/66 |
| WO | WO-2009/152166 A1 | 12/2009 | | |

OTHER PUBLICATIONS

Matsuzaki et al., "Chronic Inflammation Associated with Hepatitis C Virus Infection Perturbs Hepatic Transforming Growth Factor Beta Signaling, Promoting Cirrhosis and Hepatocellular Carcinoma", 2007, Hepatology, vol. 46, No. 1, pp. 48-57.*
International Search Report, International Application No. PCT/US12/41106, mailed Sep. 26, 2012.
Zhu et al., "Establishment and Application of a High-Throughput Screening Assay for Xanthine Oxidase Inhibitor in Vitro," Chinese Pharmaceutical Journal 42(03), pp. 187-189, 2007, abstract only.

* cited by examiner

*Primary Examiner* — My-Chau T Tran
(74) *Attorney, Agent, or Firm* — Womble Carlyle Sandridge & Rice

(57) ABSTRACT

The present invention describes [1,2,4]thiadiazine 1,1-dioxide compounds and pharmaceutically acceptable salts thereof, which are useful in lowering serum uric acid in a patient in need thereof comprising administering to the patient a therapeutically or prophylactically effective amount of a [1,2,4]thiadiazine 1,1-dioxide compound.

22 Claims, No Drawings

[1,2,4]THIADIAZINE 1,1-DIOXIDE COMPOUNDS FOR LOWERING SERUM URIC ACID

CROSS REFERENCE TO RELATED APPLICATIONS

This application claims priority to U.S. Provisional Application No. 61/494,288, filed Jun. 7, 2011, the contents of which are herein incorporated by reference.

FIELD OF THE INVENTION

The invention provides [1,2,4]thiadiazine 1,1-dioxide compounds and pharmaceutical compositions containing such compounds, useful for lowering serum uric acid and treating or preventing diseases such as hyperuricemia, gout, inflammation disease, urinary urolithiasis, reperfusion disease, renal dysfunction, tumor lysis syndrome, hypertension and cardiovascular disease.

BACKGROUND OF THE INVENTION

An abnormal increase in blood uric acid level, i.e., hyperuricemia, is a disorder that has close relation to gout, renal dysfunction, urolithiasis, etc. (*Diagnosis and Treatment,* 220-224, 244-248 (2002)). It is known that, in organ transplantation (*Ren. Fail.,* 361-7 (2002)) or chemotherapy for cancer (*Am. J. Health Syst. Pharm.,* 2213-22 (2003)), serum uric acid levels increase significantly, thereby causing renal dysfunction, or in the case of chemotherapy, serum uric acid levels increase significantly due to the rapid amount of cellular destruction (tumor lysis syndrome).

Hyperuricemia is a condition or disorder that precedes gout, resulting from increased production or decreased excretion of uric acid, or from a combination of the two processes. In an individual with hyperuricemia, plasma and extracellular fluids are supersaturated with urate, and crystal deposition in tissue is likely to occur, resulting in the clinical manifestations of gout. When crystals form in the joints it causes recurring attacks of joint inflammation. Chronic gout can also lead to deposits of hard lumps of uric acid in and around the joints and may cause joint destruction and decreased kidney function.

An agent for treating hyperuricemia may be roughly classified into an uricosuric agent or an uric acid synthesis inhibitor. The uricosuric agent may be ineffective for cases whose renal function has lowered, and therefore allopurinol, an uric acid synthesis inhibitor, is suitably used for patients having a lowered renal function.

Xanthine oxidase is an enzyme that controls the biosynthesis of uric acid, and use of a xanthine oxidase inhibitor to inhibit this enzyme is an effective treatment of hyperuricemia and various diseases caused thereby, as an uric acid synthesis inhibitor. Allopurinol is the only xanthine oxidase inhibitor that has been put into practical use at present for clinical treatment, though it is known to induce undesirable side effects.

SUMMARY OF THE INVENTION

The present invention describes [1,2,4]thiadiazine 1,1-dioxide compounds and pharmaceutically acceptable salts thereof, which are useful in lowering serum uric acid in a patient comprising administering to the patient a therapeutically effective amount of a [1,2,4]thiadiazine 1,1-dioxide compound.

In a general aspect, the invention relates to a method of lowering serum uric acid in a patient with a compound of Formula I

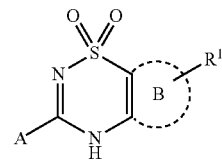

wherein
Ring B is

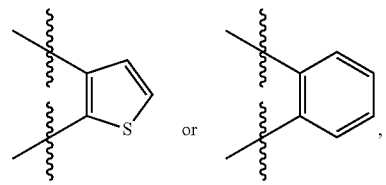 [SMILES: *c1ccsc1* ; *c1ccccc1*]

A is

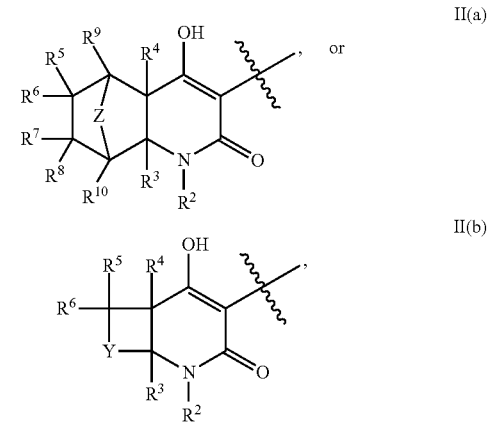

Z is $-(CR^{11}R^{12})_n-$,
Y is $-(CR^{13}R^{14})_m-$,
n is 1 or 2,
m is 2 or 3,
$R^1$ is H, $-NH_2$, or $-(CH_2)_q-NH-S(O)_2CH_3$, wherein q is 0 or 1,
$R^2$ is $C_1$-$C_6$ alkyl, $C_3$-$C_6$ cycloalkyl, aryl, or $-(CH_2)-R^{15}$, wherein $R^{15}$ is

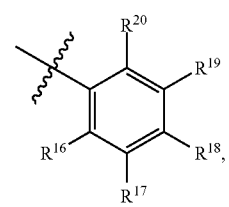

wherein $R^{16}$, $R^{17}$, $R^{18}$, $R^{19}$ and $R^{20}$ are independently H, $C_1$-$C_6$ alkyl, hydroxy, or halo, $R^3$, $R^4$, $R^5$, $R^6$, $R^7$, $R^8$, $R^9$, $R^{10}$, $R^{11}$, $R^{12}$, $R^{13}$, and $R^{14}$ are independently H or $C_1$-$C_6$ alkyl, wherein each alkyl, cycloalkyl, or aryl are optionally substituted by one or more alkyl, hydroxyl, or halo substituents, or a pharmaceutically acceptable salt, hydrate, solvate, tautomer or stereoisomer thereof.

In one embodiment, the invention relates to a method of using compounds of Formula I wherein Ring B is

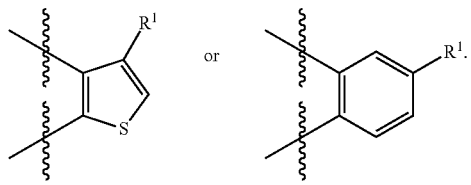

In one embodiment, the invention relates to a method of using compounds of Formula I wherein q is 1 and Ring B is

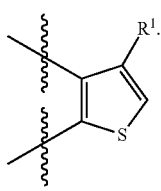

In one embodiment, the invention relates to a method of using compounds of Formula I wherein $R^1$ is H.

In one embodiment, the invention relates to a method of using compounds of Formula I wherein $R^2$ is —(CH$_2$)—$R^{15}$ and $R^{15}$ is selected from

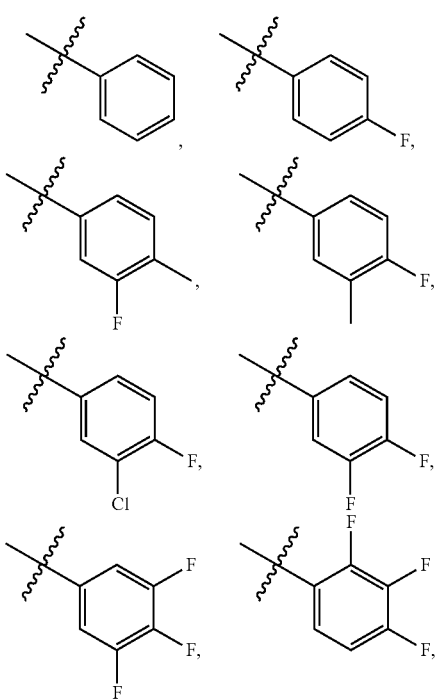

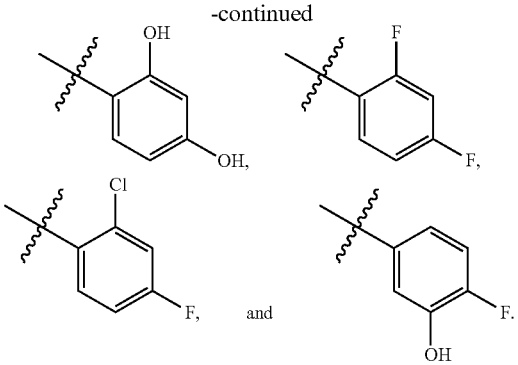

In one embodiment, the invention relates to a method of using compounds of Formula I wherein q is 0.

In one embodiment, the invention relates to a method of using compounds of Formula I wherein n is 1.

In one embodiment, the invention relates to a method of using compounds of Formula I wherein q is 0 and n is 1.

In one embodiment, the invention relates to a method of using compounds of Formula I wherein $R^3$, $R^4$, $R^5$, $R^6$, $R^7$, $R^8$, $R^9$, $R^{10}$, $R^{11}$, $R^{12}$, $R^{13}$, and $R^{14}$ are H.

In one embodiment, the invention relates to a method of using compounds of Formula I wherein $R^{16}$, $R^{17}$, $R^{18}$, $R^{19}$, and $R^{20}$ are independently H, methyl, or halo.

In one embodiment, the invention relates to a method of using compounds of Formula I wherein $R^{16}$, $R^{17}$, $R^{18}$, $R^{19}$, and $R^{20}$ are independently H or halo.

In one embodiment, the invention relates to a method of using compounds of Formula I wherein $R^{18}$ is fluoro and $R^{16}$, $R^{17}$, $R^{19}$, and $R^{20}$ are H.

In one embodiment, the invention relates to a method of using compounds of Formula I wherein
q is 0 and n is 1,
$R^3$, $R^4$, $R^5$, $R^6$, $R^7$, $R^8$, $R^9$, $R^{10}$, $R^{11}$, $R^{12}$, $R^{13}$, and $R^{14}$ are H, and
$R^{16}$, $R^{17}$, $R^{18}$, $R^{19}$, and $R^{20}$ are independently H or halo.

In another embodiment, the invention relates to compounds selected from

N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-ylmethyl}-methanesulfonamide, N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide, (1R,2S,7R,8S)-5-(1,1-Dioxo-1,4-dihydro-1λ$^6$-benzo[1,2,4]thiadiazin-3-yl)-3-(4-fluoro-benzyl)-6-hydroxy-3-aza-tricyclo[6.2.1.0$^{2,7}$]undec-5-en-4-one, (4aR,7aS)—N-{3-[1-(4-Fluoro-benzyl)-4-hydroxy-2-oxo-2,4-a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide, N-[3-(1R,2S,7R,8S)-3-Cyclopentyl-6-hydroxy-4-oxo-3-aza-tricyclo[6.2.1.0$^{2,7}$]undec-5-en-5-yl)-1,1-dioxo-1,4-dihydro-1λ$^6$-benzo[1,2,4]thiadiazin-7-yl]-methanesulfonamide, (1R,2S,7R,8S)-5-(7-Amino-1,1-dioxo-1,4-dihydro-1λ$^6$-benzo[1,2,4]thiadiazin-3-yl)-3-(4-fluoro-benzyl)-6-hydroxy-3-aza-tricyclo[6.2.1.0$^{2,7}$]undec-5-en-4-one, N-{3-[(1S,2R,7S,8R)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide, (1R,2S,7R,8S)—N-{3-[3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-yl-methyl}-methanesulfonamide, N-{3-[(2S,7R)-3-(4-Fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide, N-{3-[(1S,2S,7R,8R)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide, and N-{3-[1R,2R,7S,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide, or pharmaceutically acceptable salt thereof.

In one aspect, the invention encompasses a method for treating or preventing hyperuricemia, gout, inflammation disease, urinary urolithiasis, a reperfusion disease, renal dysfunction, tumor lysis syndrome, hypertension, or cardiovascular disease, in a patient in need thereof, comprising administering to the patient a therapeutically effective amount of a compound of Formula I and a pharmaceutically acceptable excipient, carrier, or vehicle.

In another aspect, the invention encompasses a method for lowering serum uric acid in a patient in need thereof, comprising administering to the patient a therapeutically effective amount of a compound of Formula I and a pharmaceutically acceptable excipient, carrier, or vehicle.

In another aspect, the invention encompasses a method for treating or preventing a disease associated with an abnormality of plasma uric acid level selected from hyperuricemic nephropathy and acute uric acid nephropathy.

In another aspect, the invention encompasses a method for treating or preventing hyperuricemia, gout, inflammation disease, urinary urolithiasis, a reperfusion disease, renal dysfunction, tumor lysis syndrome, hypertension, or cardiovascular disease in a patient in need thereof, comprising administering to the patient a therapeutically effective amount of a compound of Formula I and an additional therapeutic agent.

DETAILED DESCRIPTION OF THE INVENTION

Where the following terms are used in this specification, they are used as defined below:

The terms "comprising," "having" and "including" are used herein in their open, non-limiting sense.

The term "Me" means methyl, "Et" means ethyl, and "Ac" means acetyl.

The term "alkyl", as used herein, unless otherwise indicated, includes 1-6 saturated monovalent hydrocarbon radicals having straight or branched moieties.

The term "cycloalkyl", as used herein, unless otherwise indicated refers to a non-aromatic, saturated or partially saturated, monocyclic or fused, spiro or unfused bicyclic or tricyclic hydrocarbon referred to herein containing a total of from 3 to 10 carbon atoms, preferably 5-8 ring carbon atoms. Exemplary cycloalkyls include monocyclic rings having from 3-7, preferably 3-6, carbon atoms, such as cyclopropyl, cyclobutyl, cyclopentyl, cyclohexyl, cycloheptyl and the like. Illustrative examples of cycloalkyl are derived from, but not limited to, the following:

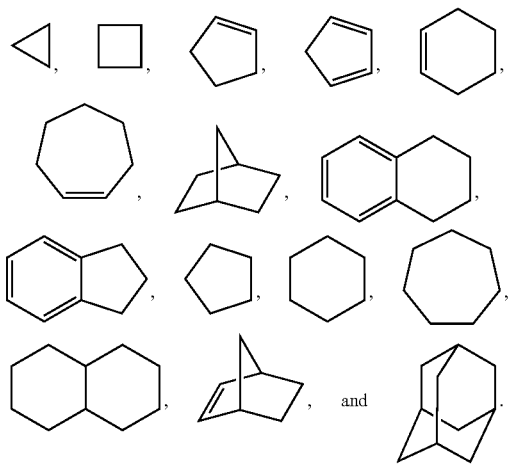

The term "aryl", as used herein, unless otherwise indicated, includes an organic radical derived from an aromatic hydrocarbon by removal of one hydrogen, and has from 6-14 carbon atoms in its ring system, such as phenyl or naphthyl.

The term "preventing" refers to the ability of a compound or composition of the invention to prevent a disease identified herein in patients diagnosed as having the disease or who are at risk of developing such disease. The term also encompasses preventing further progression of the disease in patients who are already suffering from or have symptoms of such disease.

The term "patient" or "subject" means an animal (e.g., cow, horse, sheep, pig, chicken, turkey, quail, cat, dog, mouse, rat, rabbit, guinea pig, etc.) or a mammal, including chimeric and transgenic animals and mammals. In the treatment or prevention of, e.g., gout or hyperuricemia, the term "patient" or "subject" preferably means a monkey, chimpanzee or a human, most preferably a human.

The term a "therapeutically effective amount" refers to an amount of the compound of the invention sufficient to provide a benefit in the treatment or prevention of, e.g., gout or hyperuricemia, to delay or minimize symptoms associated with preventing gout or hyperuricemia, or to cure or ameliorate the disease or infection or cause thereof. In particular, a therapeutically effective amount means an amount sufficient to provide a therapeutic benefit in vivo. Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

The term "gout" refers to a group of disorders including inflammatory arthritis, deposition of urate crystals in joints, deposition of urate crystals in renal parenchyma, urolithiasis, and nephrolithiasis.

The term "in combination" refers to the use of more than one prophylactic and/or therapeutic agents simultaneously or sequentially and in a manner that their respective effects are additive or synergistic.

The term "treating" refers to:
(i) preventing a disease, disorder, or condition from occurring in an animal that may be predisposed to the disease, disorder and/or condition, but has not yet been diagnosed as having it;
(ii) inhibiting the disease, disorder, or condition, i.e., arresting its development; and
(iii) relieving the disease, disorder, or condition, i.e., causing regression of the disease, disorder, and/or condition.

The terms "R" and "S" indicate the specific stereochemical configuration of a substituent at an asymmetric carbon atom in a chemical structure as drawn.

The term "rac" indicates that a compound is a racemate, which is defined as an equimolar mixture of a pair of enantiomers. A "rac" compound does not exhibit optical activity. The chemical name or formula of a racemate is distinguished from those of the enantiomers by the prefix (±)- or rac- (or racem-) or by the symbols RS and SR.

The terms "endo" and "exo" are descriptors of the relative orientation of substituents attached to non-bridgehead atoms in a bicyclo[x.y.z]alkane (x≥y>z>0).

The terms "syn" and "anti" are descriptors of the relative orientation of substituents attached to bridgehead atoms in a bicyclo[x.y.z]alkane (x≥y>z>0).

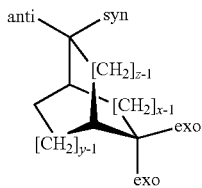

The term "exo" is given to a substituent (e.g., Br attached to C-2 in the example below) that is oriented towards the highest numbered bridge (z bridge, e.g., C-7 in example below); if the substituent is oriented away from the highest numbered bridge it is given the description "endo".

The term "syn" is given to a substituent attached to the highest numbered bridge (z bridge, e.g., F attached to C-7 in the example below) and is oriented towards the lowest numbered bridge (x bridge, e.g., C-2 and C-3 in example below); if the substituent is oriented away from the lowest numbered bridge it is given the description "anti."

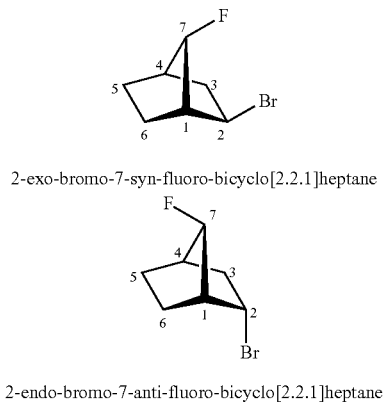

2-exo-bromo-7-syn-fluoro-bicyclo[2.2.1]heptane 2-endo-bromo-7-anti-fluoro-bicyclo[2.2.1]heptane The terms "cis" and "trans" are descriptors which show the relationship between two ligands attached to separate atoms that are connected by a double bond or are contained in a ring. The two ligands are said to be located cis to each other if they lie on the same side of a plane. If they are on opposite sides, their relative position is described as trans. The appropriate reference plane of a double bond is perpendicular to that of the relevant σ-bonds and passes through the double bond. For a ring it is the mean plane of the ring(s).

The compounds utilized in the methods of the invention may exhibit the phenomenon of tautomerism. While Formula I cannot expressly depict all possible tautomeric forms, it is to be understood that Formula I is intended to represent any tautomeric form of the depicted compound and is not to be limited merely to a specific compound form depicted by the formula drawings.

Some of the compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds utilized in the methods of the present invention are used in a form that is at least 90% free of other enantiomers or diastereomers of the compounds, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, Formula I is intended to cover solvated as well as unsolvated forms of the identified structures. For example, Formula I includes compounds of the indicated structure in both hydrated and non-hydrated forms. Other examples of solvates include the structures in combination with isopropanol, ethanol, methanol, DMSO, ethyl acetate, pentyl acetate, acetic acid, or ethanolamine.

In addition to compounds of Formula I, the invention includes pharmaceutically acceptable prodrugs, pharmaceutically active metabolites, and pharmaceutically acceptable salts of such compounds and metabolites.

"A pharmaceutically acceptable prodrug" is a compound that may be converted under physiological conditions or by solvolysis to the specified compound or to a pharmaceutically acceptable salt of such compound prior to exhibiting its pharmacological effect(s). Typically, the prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the compounds of Formula I using methods known in the art, such as those described by *Burger's Medicinal Chemistry and Drug Chemistry*, 1, 172-178, 949-982 (1995). See also Bertolini et al., *J. Med. Chem.*, 40, 2011-2016 (1997); Shan, et al., *J. Pharm. Sci.*, 86 (7), 765-767; Bagshawe, *Drug Dev. Res.*, 34, 220-230 (1995); Bodor, *Advances in Drug Res.*, 13, 224-331 (1984); Bundgaard, *Design of Prodrugs* (Elsevier Press 1985); Larsen, *Design and Application of Prodrugs*, Drug Design and Development (Krogsgaard-Larsen et al., eds., Harwood Academic Publishers, 1991); Dear et al., *J. Chromatogr. B*, 748, 281-293 (2000); Spraul et al., *J. Pharmaceutical & Biomedical Analysis*, 10, 601-605 (1992); and Prox et al., *Xenobiol.*, 3, 103-112 (1992).

"A pharmaceutically active metabolite" is intended to mean a pharmacologically active product produced through metabolism in the body of a specified compound or salt thereof. After entry into the body, most drugs are substrates for chemical reactions that may change their physical properties and biologic effects. These metabolic conversions, which usually affect the polarity of the Formula I compounds, alter the way in which drugs are distributed in and excreted from the body. However, in some cases, metabolism of a drug is required for therapeutic effect. For example, anticancer drugs of the anti-metabolite class must be converted to their active forms after they have been transported into a cancer cell.

Since most drugs undergo metabolic transformation of some kind, the biochemical reactions that play a role in drug metabolism may be numerous and diverse. The main site of drug metabolism is the liver, although other tissues may also participate.

A feature characteristic of many of these transformations is that the metabolic products, or "metabolites," are more polar than the parent drugs, although a polar drug does sometime yield a less polar product. Substances with high lipid/water partition coefficients, which pass easily across membranes, also diffuse back readily from tubular urine through the renal tubular cells into the plasma. Thus, such substances tend to have a low renal clearance and a long persistence in the body. If a drug is metabolized to a more polar compound, one with a lower partition coefficient, its tubular reabsorption will be greatly reduced. Moreover, the specific secretory mechanisms for anions and cations in the proximal renal tubules and in the parenchymal liver cells operate upon highly polar substances.

As a specific example, phenacetin (acetophenetidin) and acetanilide are both mild analgesic and antipyretic agents, but are transformed within the body to a more polar and more effective metabolite, p-hydroxyacetanilid (acetaminophen), which is widely used today. When a dose of acetanilide is given to a person, the successive metabolites peak and decay in the plasma sequentially. During the first hour, acetanilide is the principal plasma component. In the second hour, as the acetanilide level falls, the metabolite acetaminophen concentration reaches a peak. Finally, after a few hours, the principal plasma component is a further metabolite that is inert and can be excreted from the body. Thus, the plasma concentrations of one or more metabolites, as well as the drug itself, can be pharmacologically important.

"A pharmaceutically acceptable salt" is intended to mean a salt that retains the biological effectiveness of the free acids and bases of the specified compound and that is not biologically or otherwise undesirable. A compound utilized in the methods of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an α-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the compounds and salts may exist in different crystal, co-crystal, or polymorphic forms, all of which are intended to be within the scope of the present invention and specified formulas.

Methods of Treatment and Prevention of Hyperuricemia, Etc.

The present invention provides methods for lowering serum uric acid and treating or preventing hyperuricemia, gout, inflammation disease, urinary urolithiasis, a reperfusion disease, renal dysfunction, tumor lysis syndrome, hypertension, or cardiovascular disease in a patient in need thereof, comprising administering to the patient a therapeutically effective amount of a compound of Formula I and a pharmaceutically acceptable excipient, carrier, or vehicle.

The magnitude of a prophylactic or therapeutic dose of a Formula I compound of the invention or a pharmaceutically acceptable salt, solvate, or hydrate, thereof in the acute or chronic treatment or prevention of elevated uric acid levels will vary. The dose, and in some cases the dose frequency, will also vary according to the disease or condition to be treated, the age, body weight, and response of the individual patient. Suitable dosing regimens can be readily selected by those skilled in the art with due consideration of such factors.

Doses

Toxicity and efficacy of the compounds utilized in the methods of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage of the compounds for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $EC_{50}$ (i.e., the concentration of the test compound that provokes a response halfway between the baseline and maximum response) as determined in cell culture; alternatively, the dose of the Formula I compound may be formulated in animal models to achieve a circulating plasma concentration range of the compound that corresponds to the concentration required to achieve a fixed magnitude of response. Such information can be used to more accurately determine useful doses in humans. Levels in plasma may be measured, for example, by high performance liquid chromatography.

The protocols and compositions utilized in the methods of the invention are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which cells that are responsive to the effects of the Formula I compounds are exposed to the ligand and the magnitude of response is measured by an appropriate technique. The assessment of the Formula I compound is then evaluated with respect to the Formula I compound potency, and the degree of conversion of the Formula I compound prodrug, in instances where the compound to be tested is a prodrug. Compounds for use in methods of the invention can be tested in suitable animal model systems prior to testing in humans, including but not limited to in rats, mice, chicken, cows, monkeys, chimpanzees, rabbits, hamsters, etc. The compounds can then be used in the appropriate clinical trials.

Suitable dosing regimens can be readily selected by those skilled in the art with due consideration of such factors. In one embodiment, the dose administered depends upon the specific compound to be used, and the weight and condition of the patient. Also, the dose may differ for various particular Formula I compounds; suitable doses can be predicted on the basis of the aforementioned in vitro measurements and on the basis of animal studies, such that smaller doses will be suitable for those Formula I compounds that show effectiveness at lower concentrations than other Formula I compounds when measured in the systems described or referenced herein. In general, the dose per day is in the range of from about 0.001 to 100 mg/kg, preferably about 1 to 25 mg/kg, more preferably about 5 to 15 mg/kg.

Additionally, the recommended daily dose can be administered in cycles as single agents or in combination with other therapeutic agents. In one embodiment, the daily dose is administered in a single dose or in equally divided doses. In a related embodiment, the recommended daily dose can be administered one time per week, two times per week, three times per week, four times per week or five times per week.

In one embodiment, the compounds utilized in the methods of the invention are administered to provide systemic distribution of the compound within the patient. In a related embodiment, the compounds of the invention are administered to produce a systemic effect in the body.

In another embodiment the compounds utilized in the methods of the invention are administered via oral, mucosal (including sublingual or buccal), parenteral (including subcutaneous, intramuscular, bolus injection, intraarterial, or intravenous), transdermal, or topical administration. In a specific embodiment the compounds of the invention are administered via mucosal (including sublingual or buccal), parenteral (including subcutaneous, intramuscular, bolus injection, intraarterial, or intravenous), transdermal, or topical administration. In a further specific embodiment, the compounds of the invention are administered via oral administration. In a further specific embodiment, the compounds of the invention are not administered via oral administration.

Combination Therapy

Specific methods of the invention further comprise the administration of an additional therapeutic agent (i.e., a therapeutic agent other than a compound of the invention). In certain embodiments of the present invention, the compounds of the invention can be used in combination with at least one other therapeutic agent. Therapeutic agents include, but are not limited to colchicines, anti-inflammatory agents, intraarticular glucocorticoids, IL-1b antagonists (e.g., rilonacept, canakumab), inhibitors of uric acid production like the xanthine oxidase inhibitors or prodrugs of such inhibitors like febuxostat, oxypurinol, allopurinol, agents that degrade uric acid like pegloticase and other uricases, and uricosuric agents like probenecid and sulfinpyrazone. The compounds of the invention and the other therapeutics agent can act additively or, more preferably, synergistically. In one embodiment, a composition comprising a compound of the invention is administered concurrently with the administration of another therapeutic agent, which can be part of the same composition or in a different composition from that comprising the compounds of the invention. In another embodiment, a compound of the invention is administered prior to or subsequent to administration of another therapeutic agent. In a separate embodiment, a compound of the invention is administered to a patient who has not previously undergone or is not currently undergoing treatment with another therapeutic agent.

In one embodiment, the methods of the invention comprise the administration of one or more compounds of the invention without an additional therapeutic agent.

Pharmaceutical Compositions and Dosage Forms

Pharmaceutical compositions and single unit dosage forms comprising a compound utilized in the methods of the invention, or a pharmaceutically acceptable salt, or hydrate thereof, are also encompassed by the invention. Individual dosage forms of the invention may be suitable for oral, mucosal (including sublingual or buccal), parenteral (including subcutaneous, intramuscular, bolus injection, intraarterial, or intravenous), transdermal, or topical administration. Pharmaceutical compositions and dosage forms of the invention typically also comprise one or more pharmaceutically acceptable excipients. Sterile dosage forms are also contemplated.

In an alternative embodiment, pharmaceutical composition encompassed by this embodiment includes a compound of the invention, or a pharmaceutically acceptable salt, or hydrate thereof, and at least one additional therapeutic agent. Examples of additional therapeutic agents include, but are not limited to, those listed above.

The composition, shape, and type of dosage forms of the invention will typically vary depending on their use. For example, a dosage form used in the acute treatment of a disease or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990). Examples of dosage forms include, but are not limited to: tablets; caplets; capsules, such as soft elastic gelatin capsules; cachets; troches; lozenges; dispersions; ointments; cataplasms (poultices); pastes; powders; dressings; creams; plasters; solutions; patches; gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise compounds of the invention, or a pharmaceutically acceptable salt or hydrate thereof comprise 0.1 mg to 1500 mg per unit to provide doses of about 0.01 to 200 mg/kg per day.

Oral Dosage Forms

Pharmaceutical compositions utilized in the methods of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients utilized in the methods of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry and/or lyophilized products ready to be dissolved or suspended in a pharmaceutically acceptable vehicle for injection (reconstitutable powders), suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal Dosage Forms

Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Topical Dosage Forms

Topical dosage forms of the invention include, but are not limited to, creams, lotions, ointments, gels, solutions, emulsions, suspensions, or other forms known to one of skill in the art. See, e.g., *Remington's Pharmaceutical Sciences*, 18th eds., Mack Publishing, Easton Pa. (1990); and *Introduction to Pharmaceutical Dosage Forms*, 4th ed., Lea & Febiger, Philadelphia (1985).

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

Mucosal Dosage Forms

Mucosal dosage forms of the invention include, but are not limited to, ophthalmic solutions and sprays, or other forms known to one of skill in the art. See, e.g., *Remington's Pharmaceutical Sciences*, 18th eds., Mack Publishing, Easton Pa. (1990); and *Introduction to Pharmaceutical Dosage Forms*, 4th ed., Lea & Febiger, Philadelphia (1985).

In addition to the formulations described previously, a compound utilized in the methods of the invention can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Alternatively, other pharmaceutical delivery systems can be employed. Liposomes, emulsions, self-emulsifying (SEDDS), and self micro-emulsifying systems (SMEDDS) are well known examples of delivery vehicles that can be used to deliver compositions of the invention. Such systems can also contain fatty acids, bile salts and mixtures of mono-, di- and triglycerides to ameliorate potential food effects. Other functional lipid excipients include esters of glycerol, PEG-esters, propylene glycol esters and polyglycerol esters. Certain organic solvents such as dimethylsulfoxide can also be employed, although usually at the cost of greater toxicity. A compound of the invention can also be delivered in a controlled release system. In one embodiment, a pump can be used (Sefton, *CRC Crit. Ref Biomed Eng.*, 1987, 14, 201; Buchwald et al., *Surgery*, 1980, 88, 507; Saudek et al., *N. Engl. J. Med.*, 1989, 321, 574). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, *J. Macromol. Sci. Rev. Macromol. Chem.*, 1983, 23, 61; see also Levy et al., *Science*, 1985, 228, 190; During et al., *Ann. Neurol.*, 1989, 25,351; Howard et al., *J. Neurosurg.*, 71, 105 (1989). In yet another embodiment, a controlled-release system can be placed in proximity of the target of the compounds of the invention thus requiring only a fraction of the systemic dose (see, e.g., Goodson, in *Medical Applications of Controlled Release*, supra, vol. 2, pp. 115 (1984)). Other controlled-release systems can be used (see, e.g., Langer, *Science*, 1990, 249, 1527).

Suitable excipients (e.g., carriers and diluents) and other materials that can be used to provide mucosal dosage forms encompassed by this invention are well known to those skilled in the pharmaceutical arts, and depend on the particular site or method which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g., Remington's Pharmaceutical Sciences, 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Kits

The invention provides a pharmaceutical pack or kit comprising one or more containers comprising a compound of the invention useful for lowering serum uric acid and the treatment or prevention of, e.g., gout or hyperuricemia. In other embodiments, the invention provides a pharmaceutical pack or kit comprising one or more containers comprising a compound of the invention useful for lowering serum uric acid and the treatment or prevention of gout or hyperuricemia and one or more containers comprising an additional therapeutic agent.

The invention also provides a pharmaceutical pack or kit comprising one or more containers comprising one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The inventive agents may be prepared using the reaction routes and synthetic schemes as described below, employing the general techniques known in the art using starting materials that are readily available. The synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or generally known in the art will be recognized as having applicability for preparing other compounds of the invention.

Preparation of Compounds

In the synthetic schemes described below, unless otherwise indicated all temperatures are set forth in degrees Celsius and all parts and percentages are by weight. Reagents were purchased from commercial suppliers such as Aldrich Chemical Company or Alfa Aesar. and were used without further purification unless otherwise indicated. All solvents were purchased from commercial suppliers such as Aldrich, EMD Chemicals or Fisher and used as received. The reactions set forth below were done generally under a positive pressure of argon or nitrogen at an ambient temperature (unless otherwise stated) in anhydrous solvents, and the reaction flasks were fitted with rubber septa for the introduction of substrates and reagents via syringe. Glassware was oven dried and/or heat dried.

The reactions were assayed by TLC and/or analyzed by LC-MS or HPLC and terminated as judged by the consumption of starting material. Analytical thin layer chromatography (TLC) was performed on glass-plates precoated with silica gel 60 $F_{254}$ 0.25 mm plates (EMD Chemicals), and visualized with UV light (254 nm) and/or iodine on silica gel and/or heating with TLC stains such as ethanolic phosphomolybdic acid, ninhydrin solution, potassium permanganate solution or ceric sulfate solution. Preparative thin layer chromatography (prepTLC) was performed on glass-plates precoated with silica gel 60 $F_{254}$ 0.5 mm plates (20×20 cm, from Thomson Instrument Company) and visualized with UV light (254 nm).

Work-ups were typically done by doubling the reaction volume with the reaction solvent or extraction solvent and then washing with the indicated aqueous solutions using 25% by volume of the extraction volume unless otherwise indicated. Product solutions were dried over anhydrous sodium sulfate and/or magnesium sulfate prior to filtration and evaporation of the solvents under reduced pressure on a rotary evaporator and noted as solvents removed in vacuo. Column chromatography was completed under positive pressure using Merck silica gel 60, 230-400 mesh or 50-200 mesh neutral alumina, Teledyne Isco flash-chromatography using prepacked RediSep silica gel columns, or Analogix flash column chromatography using prepacked SuperFlash silica gel columns Hydrogenolysis was done at the pressure indicated in the examples or at ambient pressure.

$^1$H-NMR spectra and $^{13}$C-NMR were recorded on a Varian Mercury-VX400 instrument operating at 400 MHz. NMR spectra were obtained as $CDCl_3$ solutions (reported in ppm), using chloroform as the reference standard (7.27 ppm for the proton and 77.00 ppm for carbon), $CD_3OD$ (3.4 and 4.8 ppm for the protons and 49.3 ppm for carbon), DMSO-$d_6$ (2.49 ppm for proton), or internally tetramethylsilane (0.00 ppm) when appropriate. Other NMR solvents were used as needed. When peak multiplicities are reported, the following abbreviations are used: s (singlet), d (doublet), t (triplet), q (quartet), m (multiplet), br (broadened), bs (broad singlet), dd (doublet of doublets), dt (doublet of triplets). Coupling constants, when given, are reported in Hertz (Hz).

Infrared (IR) spectra were recorded on an ATR FT-IR Spectrometer as neat oils or solids, and when given are reported in wavenumbers (cm$^{-1}$). Mass spectra reported are (+)-ES or APCI (+) LC/MS conducted by the Analytical Chemistry Department of Anadys Pharmaceuticals, Inc. Elemental analyses were conducted by the Atlantic Microlab, Inc. in Norcross, Ga. Melting points (mp) were determined on an open capillary apparatus, and are uncorrected.

Enantiomeric excess (ee) values were determined by HPLC-analysis using the Chiralpak (Chiral Technologies Inc.) columns AS-RH, 2.1×150 mm, 5 micron, λ=312 nm or AS-RH, 4.6×250 mm, 5 micron, λ=310 nm AS-RH, 2.1×150 mm, 5 micron: Binary gradient HPLC separation. Solvent A: 0.1% Formic Acid in Water, Solvent B: 0.1% Formic Acid in Acetonitrile. Injected 10 μL of sample dissolved in 50% methanol-50% water [0.1 mg/mL].

| Time (min) | % B | Flow (mL/min) |
|---|---|---|
| 0.0 | 55 | 0.3 |
| 5.0 | 95 | 0.3 |
| 5.5 | 95 | 0.3 |
| 6.0 | 55 | 0.3 |
| 12.0 | 55 | 0.3 |

AS-RH, 4.6×250 mm, 5 micron: Binary gradient HPLC separation. Solvent A: 0.05% TFA in Water, Solvent B: 0.05% TFA in Acetonitrile. Injected 3-5 μl of sample dissolved in acetonitrile [1 mg/mL].

| Time (min) | % B | Flow (mL/min) |
|---|---|---|
| 0.0 | 50 | 0.8 |
| 8.0 | 95 | 0.8 |
| 10.0 | 95 | 0.8 |
| 11.0 | 50 | 0.8 |
| 13.0 | 50 | 0.8 |

The described synthetic pathways and experimental procedures utilize many common chemical abbreviations, 2,2-DMP (2,2-dimethoxypropane), Ac (acetyl), ACN (acetonitrile), Bn (benzyl), BnOH (benzyl alcohol), Boc (tert-butoxycarbonyl), Boc$_2$O (di-tert-butyl dicarbonate), Bz (benzoyl), CSA (camphorsulfonic acid), CSI (chlorosulfonyl isocyanate), DBU (1,8-diazabicyclo[5,4,0]undec-7-ene), DCC(N,N'-dicyclohexylcarbodiimide), DCE (1,2-dichloroethane), DCM (dichloromethane), DEAD (diethylazodicarboxylate), DIBAL (diisobutylaluminum hydride), DIEA (diisopropylethylamine), DMA (N,N-dimethylacetamide), DMAP (4-(N,N-dimethylamino)pyridine), DMF (N,N-dimethylformamide), DMSO (dimethyl sulfoxide), EDC (1-(3-dimethylaminopropyl)-3-ethylcarbodiimide hydrochloride), Et (ethyl), EtOAc (ethyl acetate), EtOH (ethanol), HATU (O-(7-azabenzotriazol-1-yl)-1,1,3,3-tetramethyluronium hexafluorophosphate), HBTU (O-benzotriazol-1-yl-N,N,N', N'-tetramethyluronium hexafluorophosphate), HF (hydrogen fluoride), HOAc (acetic acid), HOBT (1-hydroxybenzotriazole hydrate), HPLC (high pressure liquid chromatography), IPA (isopropyl alcohol), KHMDS (potassium bis(trimethylsilyl)amide), KN(TMS)$_2$ (potassium bis(trimethylsilyl)amide), KO$^t$Bu (potassium tert-butoxide), LDA (lithium diisopropylamine), MCPBA (3-chloroperbenzoic acid), Me (methyl), MeCN (acetonitrile), MeOH (methanol), NaCNBH$_3$ (sodium cyanoborohydride), NaH (sodium hydride), NaN(TMS)$_2$ (sodium bis(trimethylsilyl)amide), NaOAc (sodium acetate), NaOEt (sodium ethoxide), NEt$_3$ (triethylamine), NMM (N-methylmorpholine), Phe (phenylalanine), PPTS (pyridinium p-toluenesulfonate), PS (polymer supported), Py (pyridine), pyBOP (benzotriazol-1-yloxy)tripyrrolidinophosphonium hexafluorophosphate), TEA (triethylamine), TFA (trifluoroacetic acid), TFAA (trifluoroacetic anhydride), THF (tetrahydrofuran), TLC (thin layer chromatography), Tol (toluoyl), Val (valine), and the like.

Scheme 1 provides a specific procedure that was used to prepare the compound of Example 1, an N-methylene methanesulfonamide [1,2,4]thiadiazine 1,1-dioxide derivative.

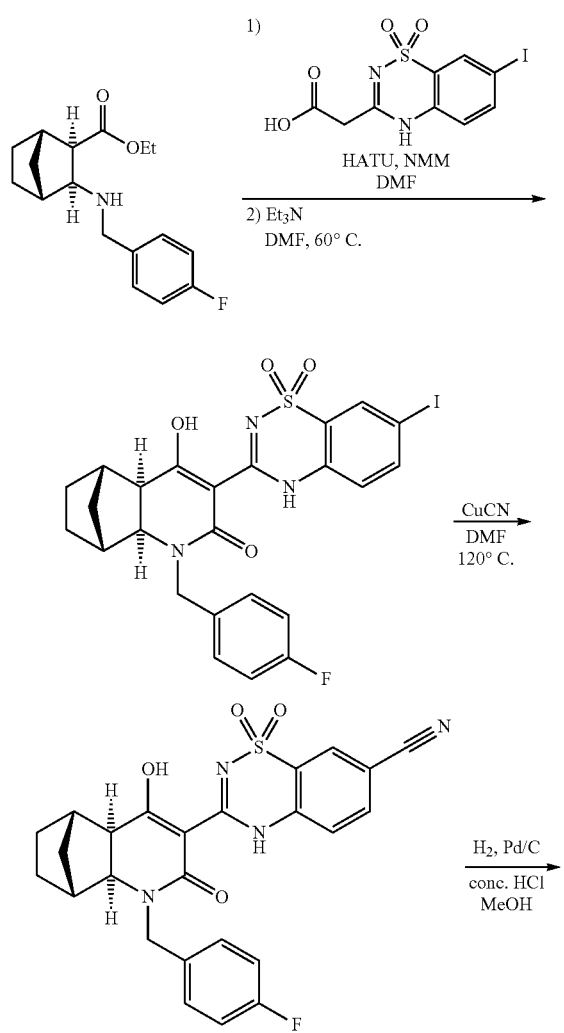

Scheme 1

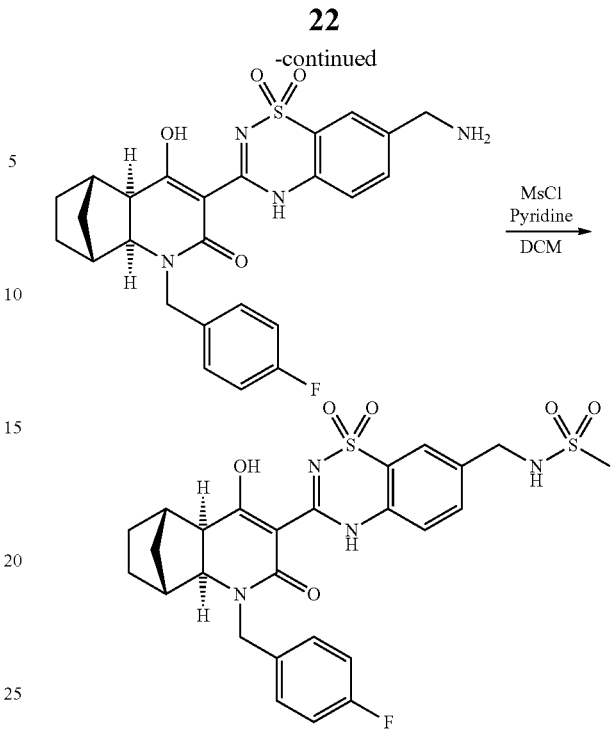

The N-substituted cyclic β-amino acid ester intermediate shown was coupled to (7-iodo-1,1-dioxo-1,4-dihydro-1λ$^6$-benzo[1,2,4]thiadiazin-3-yl)-acetic acid (prepared as described in WO2007150001A1) in the presence of O-(7-azabenzotriazol-1-yl)-1,1,3,3-tetramethyluronium hexafluorophosphate (HATU) and N-methylmorpholine to afford the amide intermediate which was cyclized in the presence of triethylamine to afford the desired cyclic intermediate. Displacement of the iodo moiety with copper (I) cyanide gave the desired nitrile intermediate. Reduction of the nitrile under standard hydrogenation conditions yielded the desired benzyl amine derivative which was then treated with methanesulfonyl chloride to afford the desired [1,2,4]thiadiazine 1,1-dioxide compound.

Example 1

N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-ylmethy}-methanesulfonamide

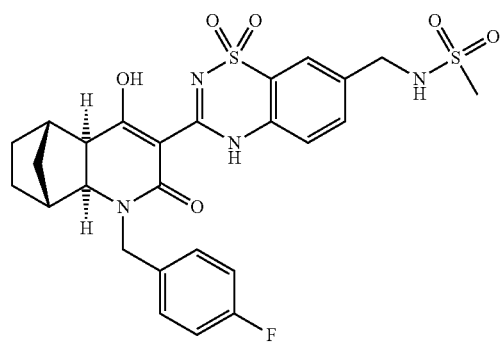

a) (1R,2S,7R,8S)-3-(4-Fluoro-benzyl)-6-hydroxy-5-(7-iodo-1,1-dioxo-1,4-dihydro-1λ⁶-benzo[1,2,4]thiadiazin-3-yl)-3-aza-tricyclo[6.2.1.0²,⁷]undec-5-en-4-one

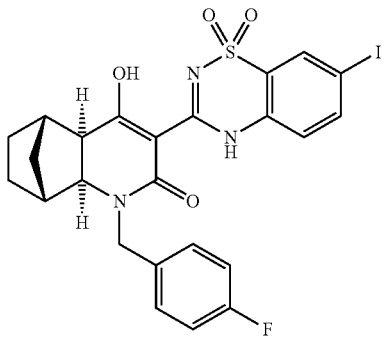

(7-Iodo-1,1-dioxo-1,4-dihydro-1λ⁶-benzo[1,2,4]thiadiazin-3-yl)-acetic acid (prepared as described in US patent application US 2008/0031852; 2.51 g, 6.86 mmol), (1S,2R,3S,4R)-3-(4-fluoro-benzylamino)-bicyclo[2.2.1]heptane-2-carboxylic acid ethyl ester (For the preparation of β-amino acid intermediates see Examples 2f-1 described below) (2 g, 6.86 mmol) and O-(7-azabenzotriazol-1-yl)-N,N,N',N'-tetramethyluronium hexafluorophosphate (2.74 g, 7.2 mmol) were combined and dissolved in anhydrous N,N-dimethylformamide (18 mL). N-Methylmorpholine (3 mL, 27.44 mmol) was added and the mixture was stirred at 25° C. for 2 h. Triethylamine (3.82 mL, 27.44 mmol) was added and the mixture stirred at 60° C. for 16 h. Upon cooling, the mixture was slowly added to a 1.0 M aqueous hydrochloric acid solution (200 mL) while stirring. The product precipitated immediately. Stirring was continued for 5 min. The solid was collected by vacuum filtration, rinsed with water (2×60 mL) and dried in vacuo for 16 h to afford the desired product, (1S,2R,3S,4R)-3-(4-fluoro-benzyl)-6-hydroxy-5-(7-iodo-1,1-dioxo-1,4-dihydro-1λ⁶-benzo[1,2,4]thiadiazin-3-yl)-3-aza-tricyclo[6.2.1.0²,⁷]undec-5-en-4-one (1.94 g, 3.27 mmol, 48%), as a white, brittle foam. ¹H NMR (400 MHz, DMSO-d₆) δ: 1.20-1.23 (1H, m), 1.38-1.61 (5H, m), 2.50-2.53 (1H, m), 2.62 (1H, d, J=3.2 Hz), 2.98 (1H, d, J=9.3 Hz), 3.52 (1H, d, J=9.4 Hz), 4.40 (1H, d, J=15.7 Hz), 4.95 (1H, d, J=14.9 Hz), 7.12-7.16 (2H, m), 7.30-7.34 (3H, m), 7.97 (1H, dd, J₁=8.6 Hz, J₂=1.4 Hz), 8.07 (1H, d, J=1.7 Hz).

b) (1R,2S,7R,8S)-3-[3-(4-Fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazine-7-carbonitrile

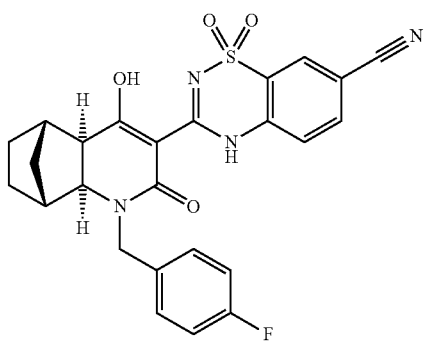

(1R,2S,7R,8S)-3-(4-Fluoro-benzyl)-6-hydroxy-5-(7-iodo-1,1-dioxo-1,4-dihydro-1λ⁶-benzo[1,2,4]thiadiazin-3-yl)-3-aza-tricyclo[6.2.1.0²,⁷]undec-5-en-4-one (0.5 g, 0.84 mmol) and copper(I) cyanide (0.151 g, 1.7 mmol) were suspended in anhydrous N,N-dimethylformamide (4 mL). The mixture was stirred at 120° C., under nitrogen for 24 h. Upon cooling, the mixture was diluted with ethyl acetate (20 mL) and washed with saturated aqueous ammonium chloride solution (3×15 mL). The organic phase was passed through a short plug of Celite followed by a short plug of silica gel (Merck silica gel 60, 40-63 μm), eluting with ethyl acetate. The filtrate was concentrated in vacuo to afford a yellow solid. Purification by flash column chromatography (Teledyne Isco RediSep column; 25-100% ethyl acetate in hexanes) followed by concentration in vacuo afforded the desired product, (1R,2S,7R,8S)-3-[3-(4-fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazine-7-carbonitrile (0.398 g, 0.808 mmol, 96%), as a white, brittle foam. ¹H NMR (400 MHz, DMSO-d₆) δ: 1.15-1.15 (1H, m), 1.34-1.61 (5H, m), 2.48-2.48 (1H, m), 2.60 (1H, d, J=3.3 Hz), 2.90 (1H, d, J=9.4 Hz), 3.48 (1H, d, J=9.4 Hz), 4.38 (1H, d, J=15.6 Hz), 4.96 (1H, d, J=15.4 Hz), 7.11-7.16 (2H, m), 7.31 (2H, dd, J₁=8.6 Hz, J₂=5.4 Hz), 7.60 (1H, d, J=8.6 Hz), 8.02 (1H, dd, J₁=8.6 Hz, J₂=2.5 Hz), 8.37 (1H, s). LC-MS (ESI) calculated for $C_{25}H_{21}FN_4O_4S$ 492.13. found 493.1 [M+H⁺].

c) (1R,2S,7R,8S)-5-(7-Aminomethyl-1,1-dioxo-1,4-dihydro-1λ⁶-benzo[1,2,4]thiadiazin-3-yl)-3-(4-fluoro-benzyl)-6-hydroxy-3-aza-tricyclo[6.2.1.0²,⁷]undec-5-en-4-one hydrochloride

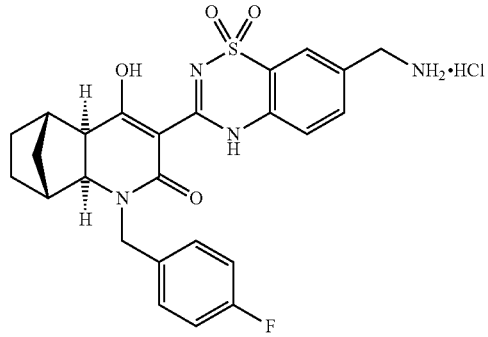

(1R,2S,7R,8S)-3-[3-(4-Fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazine-7-carbonitrile (0.38 g, 0.77 mmol) was dissolved in methanol (required gentle heating via heat gun). Concentrated aqueous hydrochloric acid solution (5 mL) was added followed by 10% palladium on carbon (~150 mg). The mixture was degassed and backfilled with hydrogen gas via balloon. The mixture stirred at 25° C. for 3 h. The mixture was passed through a plug of Celite, eluting with additional methanol (200 mL). The filtrate was concentrated in vacuo to afford the desired product, (1R,2S,7R,8S)-5-(7-aminomethyl-1,1-dioxo-1,4-dihydro-1λ⁶-benzo[1,2,4]thiadiazin-3-yl)-3-(4-fluoro-benzyl)-6-hydroxy-3-aza-tricyclo[6.2.1.0²,⁷]undec-5-en-4-one hydrochloride (~0.77 mmol), as a pale yellow solid. The solid was used directly in the next step without further purification or characterization. LC-MS (ESI) calculated for $C_{25}H_{25}FN_4O_4S$ 496.16. found 497.3 [M+H⁺].

d) N-{3-[(1R,2S,7R,8S)-3-(4-Fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-ylmethyl}-methanesulfonamide

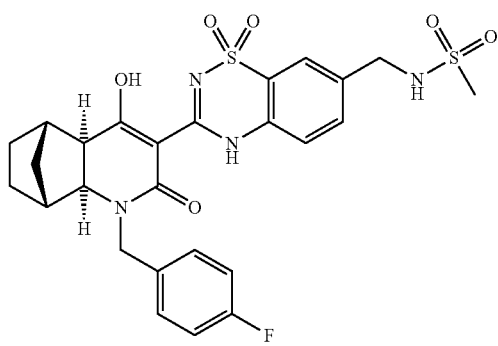

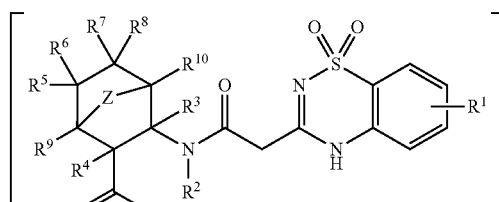

(1R,2S,7R,8S)-5-(7-Aminomethyl-1,1-dioxo-1,4-dihydro-1λ[6]-benzo[1,2,4]thiadiazin-3-yl)-3-(4-fluoro-benzyl)-6-hydroxy-3-aza-tricyclo[6.2.1.0[2,7]]undec-5-en-4-one hydrochloride (crude from previous step, ~0.77 mmol) was dissolved in methylene chloride (10 mL). Triethylamine (2 mL) and pyridine (2 mL) were added. Methane sulfonyl chloride (2 mL) was added and the mixture stirred at 25° C. for 20 min. Water (50 mL) was added and the mixture stirred for 5 min. The solution was diluted with ethyl acetate (200 mL) and washed with 1.0 M aqueous hydrochloric acid solution (3×300 mL), saturated aqueous ammonium chloride solution (2×200 mL) and saturated aqueous brine solution (200 mL). The organic phase was dried over magnesium sulfate, filtered and concentrated in vacuo to afford a clear oil. Purification by flash column chromatography (Teledyne Isco RediSep column; 25-100% ethyl acetate in hexanes) followed by concentration in vacuo afforded the desired product, N-{3-[(1R,2S,7R,8S)-3-(4-fluoro-benzyl)-6-hydroxy-4-oxo-3-aza-tricyclo[6.2.1.0[2,7]]undec-5-en-5-yl]-1,1-dioxo-1,4-dihydro-1λ[6]-benzo[1,2,4]thiadiazin-7-ylmethyl}-methanesulfonamide (0.139 g, 0.238 mmol, 31%) as a white, brittle foam. $^1$H NMR (400 MHz, DMSO-$d_6$) δ: 1.19-1.25 (1H, m), 1.40-1.64 (5H, m), 2.50-2.54 (1H, m), 2.64 (1H, d, J=2.5 Hz), 2.92 (3H, s), 3.04 (1H, d, J=8.8 Hz), 3.53 (1H, d, J=9.5 Hz), 4.25 (2H, d, J=6.2 Hz), 4.42 (1H, d, J=15.8 Hz), 4.97 (1H, d, J=14.7 Hz), 7.12-7.17 (2H, m), 7.33 (2H, dd, $J_1$=7.7 Hz, $J_2$=5.4 Hz), 7.52 (1H, d, J=8.7 Hz), 7.63-7.70 (2H, m), 7.81 (1H, s). LC-MS (ESI) calculated for $C_{26}H_{27}FN_4O_6S_2$ 574.14. found 575.3 [M+H$^+$].

Scheme 2 provides a general procedure that can be used to prepare saturated 5,6-dihydro-1H-pyridin-2-one compounds of Examples 2, 3, 5, 6, 7, 9, 10 and 11.

The saturated cyclic N-substituted-β-amino acid ester intermediates can be obtained as described by one of the methods in Schemes 2a-e which can be condensed with a carboxylic acid intermediate using standard peptide coupling conditions used for the formation of amide bonds, such as DCC, to yield the shown amide. This intermediate can be cyclized with or without isolation in the presence of a base (e.g., triethylamine) to give the desired saturated 5,6-dihydro-1H-pyridin-2-one compounds.

Scheme 2

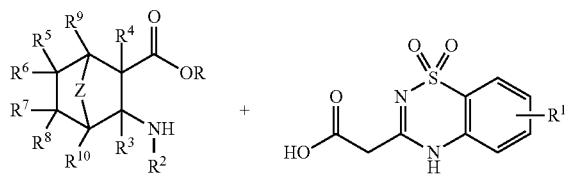

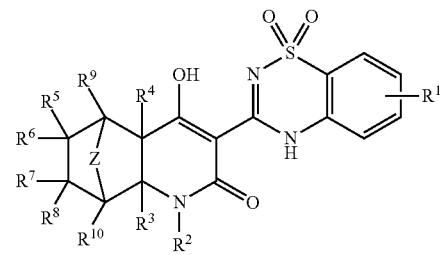

Scheme 2a

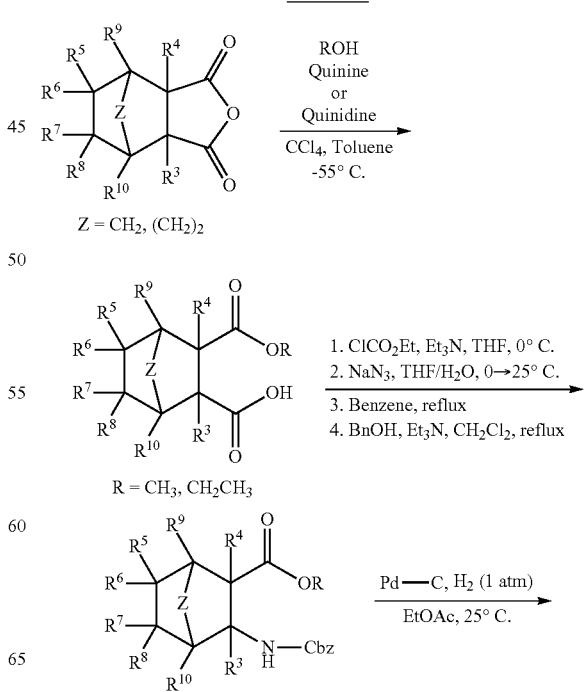

-continued

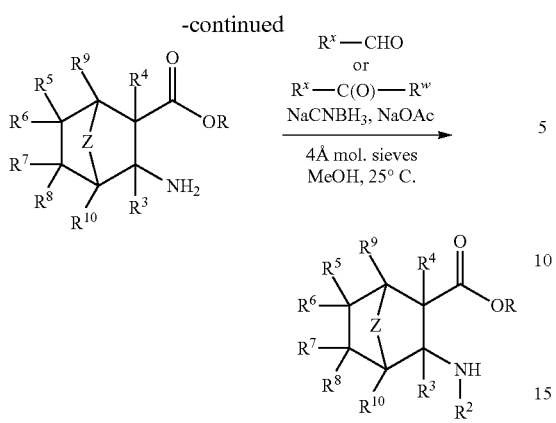

Commercially available saturated cyclic meso-anhydrides can be desymmetrized with the help of enzymes or chiral reagents, such as cinchona alkaloids (e.g., quinine or quinidine) as described in the literature to provide optically active saturated cyclic dicarboxylic acid monoesters. See *J. Org. Chem.*, 65, 6984-6991 (2000); *Synthesis*, 11, 1719-1730 (2001), and references cited therein. These intermediates can be further elaborated into protected optically active saturated cyclic β-amino acid esters (e.g., Cbz-protected) via a rearrangement reaction, such as the Curtius rearrangement (shown) or a Hofmann degradation. Hydrogenation of the protected saturated cyclic β-amino acid esters under standard conditions can be used to remove the protecting group and furnish the optically active saturated cyclic β-amino acid esters, which can be isolated (and used) as either the free bases or their corresponding salts. The optically active saturated cyclic β-amino acid esters (or their salts) can then be treated with aldehydes or ketones, where $R^x$ and $R^w$ are independently $C_1$-$C_5$ alkyl, $C_3$-$C_8$ cycloalkyl, —$C_1$-$C_5$ alkylene($C_3$-$C_8$ cycloalkyl), —$C_1$-$C_5$ alkylene(aryl), —$C_1$-$C_5$ alkylene(heterocyclyl), aryl, or heterocyclyl, or $R^w$ can combine with $R^x$ to form a 3- to 8-membered ring, in the presence of a reducing agent (such as sodium cyanoborohydride) to afford the desired optically active saturated cyclic N-substituted-β-amino acid ester intermediates. Alternatively, the reaction sequence described above can be performed without enzymes or chiral reagents leading to the corresponding achiral intermediates and products.

Scheme 2b provides a general procedure that can be used to prepare cyclic N-substituted-β-amino acid ester intermediates from unsaturated anhydrides.

Scheme 2b

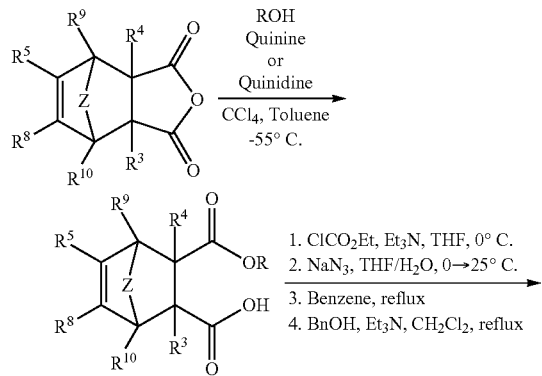

-continued

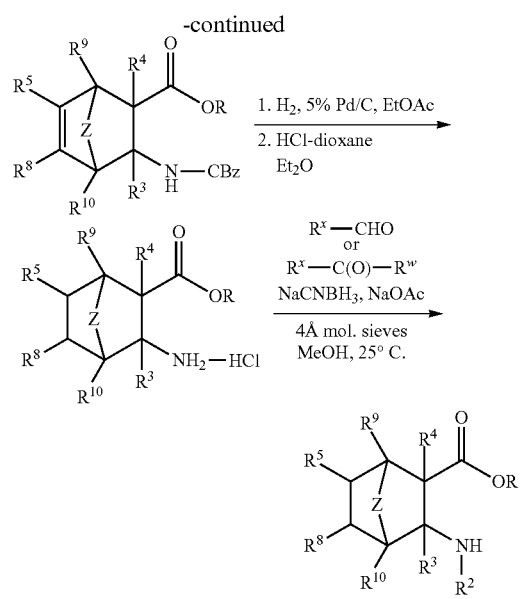

$Z = CH_2, (CH_2)_2$
$R = CH_3, CH_2CH_3$

Commercially available unsaturated cyclic meso-anhydrides can be desymmetrized as described above in Scheme 2b to provide optically active unsaturated cyclic dicarboxylic acid monoesters. These intermediates can be further elaborated into protected optically active unsaturated cyclic β-amino acid esters (e.g., CBz-protected) via a rearrangement reaction, such as the Curtius rearrangement (shown) or a Hofmann degradation. The CBz protecting group can then be removed and the olefin reduced via catalytic hydrogenation, thus leading to the optically active unsaturated cyclic β-amino acid ester intermediates, which can be isolated (and used) as either the salts or their corresponding free bases.

Scheme 2c provides an alternate general procedure that can be used to prepare saturated cyclic N-substituted-β-amino acid ester intermediates.

Scheme 2c

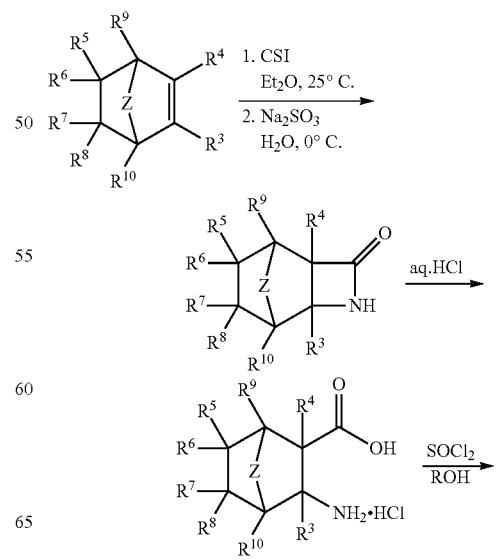

-continued

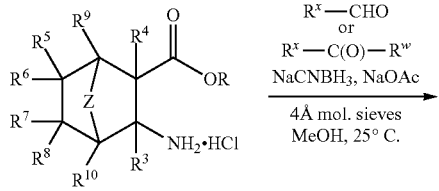

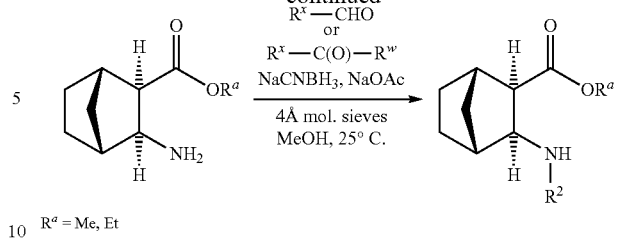

$R^a$ = Me, Et

The racemic di-exo-β-amino acid ester derivatives obtained from norbornene as described above, can be resolved by forming diastereomeric salts with an optically pure acid, such as (1S)-(+)-10-camphorsulfonic acid. The (1R,2R,3S,4S)-β-amino acid ester derivatives form a crystalline salt with (1S)-(+)-10-camphorsulfonic acid that can be selectively isolated by filtration from an appropriate solvent (e.g., ethyl acetate) and treated with a base, such as sodium carbonate, to afford the free enantiomerically pure cyclic (1R,2R,3S,4S)-β-amino acid esters. The optically pure cyclic (1R,2R,3S,4S)-β-amino acid esters (or their salts) can then be treated with aldehydes or ketones in the presence of a reducing agent, such as sodium cyanoborohydride, to afford the desired optically pure saturated cyclic N-substituted-(1R,2R, 3S,4S)-β-amino acid ester intermediates.

Scheme 2e provides an alternative procedure that can be used to prepare enantiomerically pure saturated cyclic N-substituted-β-amino acid ester intermediates.

$Z = CH_2, (CH_2)_2$

Bicyclic olefins, such as norbornene, can be reacted with chlorosulfonyl isocyanate to yield the β-lactams shown. These intermediates can be hydrolyzed in the presence of a strong acid (such as hydrochloric acid) to afford the saturated cyclic β-amino acids (or their salts), which can then be further elaborated into the corresponding esters using standard conditions. The saturated cyclic β-amino acid esters can then be treated with aldehydes or ketones in the presence of a reducing agent, such as sodium cyanoborohydride, to afford the desired saturated cyclic N-substituted-β-amino acid ester intermediates.

Scheme 2d provides a general scheme describing a method that can be used to resolve the di-exo enantiomers by diastereomeric crystallization.

Scheme 2d

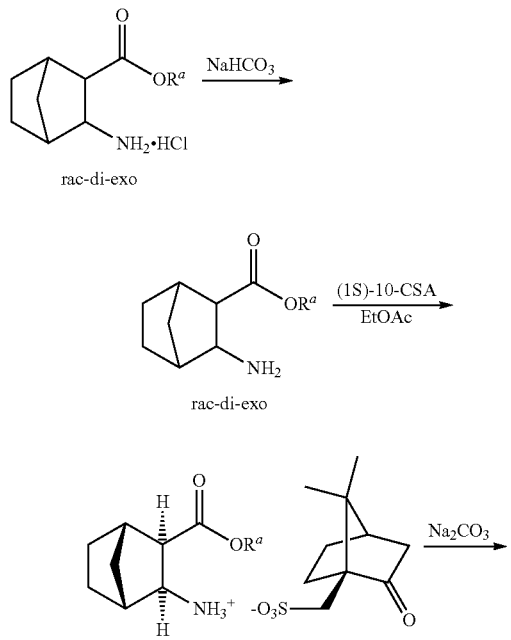

Scheme 2e

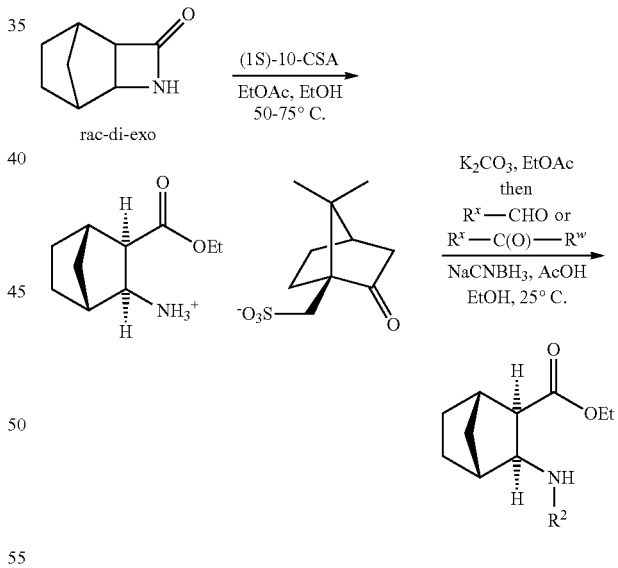

The β-lactam (prepared as described in Scheme 2c) can be opened and resolved by forming diastereomeric salts with an optically pure acid, such as (1S)-(+)-10-camphorsulfonic acid (as described in scheme 2d) in the presence of an alcohol (e.g., ethanol) to directly afford the diastereomerically pure (1R,2R,3S,4S)-β-amino acid ester as a salt with (1S)-(+)-10-camphorsulfonic acid. Treatment with a base, such as potassium carbonate, followed by reductive alkylation with aldehydes or ketones in the presence of a reducing agent, such as sodium cyanoborohydride, affords the desired enantiomerically pure saturated cyclic N-substituted-(1R,2R,3S,4S)-β-amino acid ester intermediates.

Example 2

N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

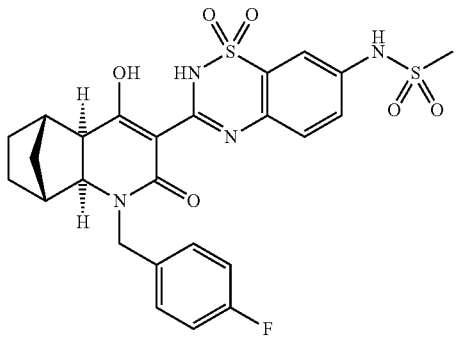

a) (1S,2S,3R,4R)-3-(Methoxycarbonyl)bicyclo[2.2.1]hept-5-ene-2-carboxylic acid

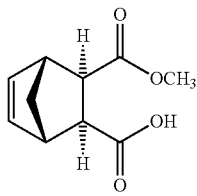

The title compound was prepared as described in *J. Org. Chem.* 2000, 65, 6984-6991. cis-5-Norbornene-endo-2,3-dicarboxylic anhydride (5 g, 30.45 mmol) was suspended in a 1:1 mixture of toluene and carbon tetrachloride (610 mL). The mixture was stirred for 10 min. Quinine (10.87 g, 33.5 mmol) was added and the flask was degassed and backfilled with nitrogen. The solution was cooled to –55° C. While stirring, methanol (3.7 mL, 91.35 mmol) was added. The mixture was stirred at –55° C. for 16 h. Upon warming to 25° C., the mixture was concentrated in vacuo to a foam. The foam was dissolved in a mixture of ethyl acetate (400 mL) and 1.0 M aqueous hydrochloric acid solution (400 mL). The layers were separated and the organic layer was further washed with 1.0 M aqueous hydrochloric acid solution (2×200 mL), aqueous saturated brine solution (100 mL) and dried over magnesium sulfate, filtered, and concentrated in vacuo to afford the desired product, (1S,2S,3R,4R)-3-(methoxycarbonyl)bicyclo[2.2.1]hept-5-ene-2-carboxylic acid (5.95 g, 30.3 mmol, 99% yield) as a clear oil. $^1$H NMR (400 MHz, DMSO-d$_6$) δ: 1.31 (1H, d, J=8.5 Hz), 1.98 (1H, d, J=8.6 Hz), 2.51 (2H, d, J=1.6 Hz), 2.95 (2H, bs), 3.52 (3H, s), 6.17-6.21 (2H, m), 12.16 (1H, s).

b) Methyl (1R,2R,3S,4S)-3-{[(benzyloxy)carbonyl]amino}bicyclo[2.2.1]hept-5-ene-2-carboxylate

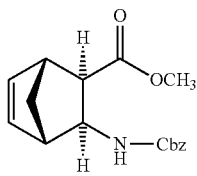

(1S,2S,3R,4R)-3-(Methoxycarbonyl)bicyclo[2.2.1]hept-5-ene-2-carboxylic acid (5.9 g, 30 mmol) was dissolved in anhydrous tetrahydrofuran (133 mL). The flask was degassed and backfilled with nitrogen and the mixture was cooled to 0° C. Triethylamine (12.64 mL, 90 mmol) was added followed by the dropwise addition of ethyl chloroformate (5.72 mL, 60 mmol) with vigorous stirring. Immediate precipitation was observed. The mixture was stirred at 0° C. for 1 h. Sodium azide (5.86 g, 90 mmol) was dissolved in water (40 mL) and added to the reaction mixture at 0° C. The mixture was stirred at 0° C. for 5 min. The ice bath was removed. The mixture was warmed to 25° C. and continued to stir for 2 h. The mixture was poured into water (300 mL) and the product extracted into ethyl acetate (300 mL). The organic layer was further washed with ½ saturated aqueous sodium bicarbonate solution (2×100 mL), aqueous saturated brine solution (100 mL), dried over magnesium sulfate, filtered, and concentrated in vacuo to afford a light brown oil. The oil was dissolved in anhydrous benzene (66 mL) and refluxed while stirring under nitrogen for 2 h. Upon cooling to 25° C. the solution was concentrated in vacuo to afford a light brown oil. The oil was dissolved in dichloromethane (40 mL) and benzyl alcohol (3.41 mL, 33 mmol) was added followed by triethylamine (8.44 mL, 60 mmol). The mixture was refluxed under nitrogen for 16 h. Upon cooling to 25° C. the solution was concentrated in vacuo to afford a thick oil. Purification by flash column chromatography (Merck silica gel 60, 40-63 μm, column 1: 3:1 hexanes/ethyl acetate; column 2: 2:4:1 dichloromethane/pentane/diethyl ether) afforded the desired product, methyl (1R,2R,3S,4S)-3-{[(benzyloxy)carbonyl]amino}bicyclo[2.2.1]hept-5-ene-2-carboxylate (6.95 g, 23.09 mmol, 77% yield) as a pale yellow oil. $^1$H NMR (400 MHz, CDCl$_3$) δ: 1.59 (1H, d, J=9.3 Hz), 1.96 (1H, d, J=9.3 Hz), 2.66 (1H, d, J=7.9 Hz), 2.75 (1H, s), 2.96 (1H, s), 3.59 (3H, s), 4.01 (1H, t, J=8.5 Hz), 5.09 (2H, q, J=10.4 Hz), 5.46 (1H, d, J=9.4 Hz), 6.17-6.22 (2H, m), 7.29-7.36 (5H, m). LC-MS (ESI) calcd for C$_{17}$H$_{19}$NO$_4$ 301.13. found 258.1 (100%), 302.2 [M+H$^+$] (70%), 603.5 [2M+H$^+$] (20%).

c) Methyl (1S,2R,3S,4R)-3-aminobicyclo[2.2.1]heptane-2-carboxylate hydrochloride

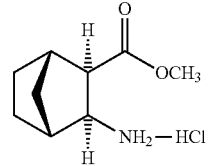

Methyl (1R,2R,3S,4S)-3-{[(benzyloxy)carbonyl]amino}bicyclo[2.2.1]hept-5-ene-2-carboxylate (1 g, 3.32 mmol) was dissolved in ethyl acetate (15 mL). 5% Palladium on carbon (120 mg) was added. The flask was degassed and backfilled with hydrogen gas via balloon. The mixture was stirred at 25° C. for 16 h. The mixture was passed through a plug of Celite and the filtrate was concentrated in vacuo to afford a thick clear oil. The oil was dissolved in diethyl ether (10 mL) and added dropwise, with vigorous stifling, to a mixture of 4.0 M hydrochloric acid solution in 1,4-dioxane (1.8 mL) in diethyl ether (18 mL). The desired product began to precipitate as a white solid. Additional diethyl ether (10 mL) was added and the mixture was stirred for 10 min. The precipitate was collected by vacuum filtration, washed with additional diethyl ether (2×8 mL). The solid was further dried in vacuo for 1 h. to afford the desired product, methyl (1S,2R,3S,4R)-3-aminobicyclo[2.2.1]heptane-2-carboxylate hydrochloride (0.64 g, 3.11 mmol, 94% yield) as a white powder. $^1$H NMR (400 MHz, DMSO-d$_6$) δ: 1.17-1.27 (3H, m), 1.40-1.61 (2H, m), 1.91 (1H, d, J=10.7 Hz), 2.36 (1H, d, J=4.1 Hz), 2.44 (1H, d, J=3.1 Hz), 2.75 (1H, d, J=7.8 Hz), 3.30-3.38 (1H, m), 3.61 (3H, s), 8.05 (3H, bs). LC-MS (ESI) calcd for $C_9H_{15}NO_2$ (free amine) 169.11. found 170.3 [M+H$^+$] (100%), 339.3 [2M+H$^+$] (50%).

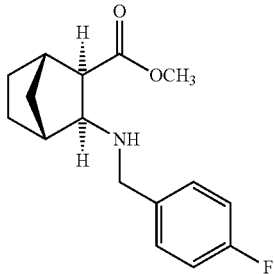

d) Methyl (1S,2R,3S,4R)-3-[(4-Fluorobenzyl)amino]bicyclo[2.2.1]heptane-2-carboxylate Methyl (1S,2R,3S,4R)-3-aminobicyclo[2.2.1]heptane-2-carboxylate hydrochloride (0.5 g, 2.43 mmol) was dissolved in methanol (12 mL). Sodium acetate (0.4 g, 4.86 mmol) was added followed by 4 Å powdered molecular sieves (0.5 g) and 4-fluoro-benzaldehyde (0.302 g, 2.43 mmol). Sodium cyanoborohydride (0.305 g, 4.86 mmol) was added and the mixture was stirred at 25° C. for 16 h. The mixture was poured into a mixture of aqueous saturated sodium bicarbonate solution (200 mL) and ethyl acetate (300 mL). After shaking, both layers were passed through a plug of Celite. The organic phase was further washed with aqueous saturated sodium bicarbonate solution (100 mL), aqueous saturated brine solution (100 mL), dried over magnesium sulfate, filtered, and concentrated in vacuo to afford the crude product, methyl (1S,2R,3S,4R)-3-[(4-fluorobenzyl)amino]bicyclo[2.2.1]heptane-2-carboxylate (0.663 g, 2.39 mmol, 98% yield) as a clear oil. LC-MS (ESI) calcd for $C_{16}H_{20}FNO_2$ 277.15. found 278.2 [M+H$^+$] (100%).

e) N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

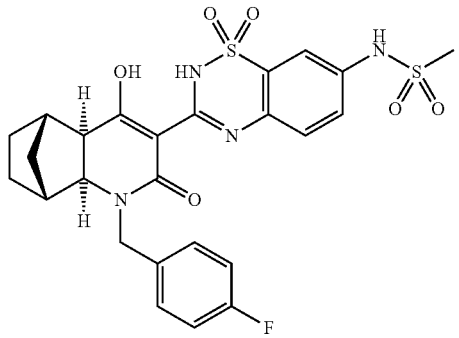

Methyl (1S,2R,3S,4R)-3-[(4-fluorobenzyl)amino]bicyclo[2.2.1]heptane-2-carboxylate (0.6 g, 2.16 mmol) was dissolved in anhydrous N,N-dimethylformamide (20 mL). (7-Methanesulfonylamino-1,1-dioxo-1,4-dihydro-1λ$^6$-benzo[1,2,4]thiadiazin-3-yl)-acetic acid (U.S. Pat. No. 7,939, 524 B2) (0.72 g, 2.16 mmol) was added followed by N-methylmorpholine (0.5 mL, 4.54 mmol). The mixture was stirred until everything dissolved, approximately 5 min. 1-(3-Dimethylaminopropyl)-3-ethylcarbodiimide hydrochloride (0.435 g, 2.27 mmol) was added and the mixture was stirred at 25° C. for 45 min Triethylamine (0.91 mL, 6.48 mmol) was added and the mixture was stirred at 50° C. for 16 h.

Upon cooling to 25° C., the solution was diluted with ethyl acetate (300 mL) and washed with 1.0 M aqueous hydrochloric acid solution (3×300 mL), aqueous saturated brine solution (100 mL), dried over magnesium sulfate, filtered, and concentrated in vacuo to afford a golden oil. Purification by flash column chromatography (Merck silica gel 60, 40-63 μm, 0 to 0.75% methanol in dichloromethane) afforded the product as white foam. The foam was dissolved in methanol (10 mL) and the product was precipitated by the addition of 1.0 M aqueous hydrochloric acid solution (20 mL) while stifling. The solid was collected by vacuum filtration and further dried in vacuo to afford the desired product, N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (0.573 g, 1.02 mmol, 47% yield) as a white powder. $^1$H NMR (400 MHz, DMSO-d$_6$) δ: 1.16-1.22 (2H, m), 1.37-1.65 (4H, m), 2.49-2.53 (1H, m), 2.63 (1H, d, J=2.3 Hz), 3.02 (1H, d, J=8.5 Hz), 3.05 (3H, s), 3.52 (1H, d, J=9.4 Hz), 4.41 (1H, d, J=15.6 Hz), 4.95 (1H, d, J=15.6 Hz), 7.14 (2H, t, J=9.0 Hz), 7.32 (2H, dd, J$_1$=8.1 Hz, J$_2$=5.7 Hz), 7.50 (1H, dd, J$_1$=9.5 Hz, J$_2$=2.3 Hz), 7.55-7.57 (2H, m), 10.17 (1H, s). LC-MS (ESI) calcd for $C_{25}H_{25}FN_4O_6S_2$ 560.12. found 561.3 [M+H$^+$] (100%). ee=90% [HPLC-analysis: Chiralpak AS-RH 2.1×150 mm, 5 micron at r.t., Solvent A-Solvent B (see table for gradient), 0.3 mL/min, 312 nm, t1=4.3 min (major), t2=6.0 min]

Alternatively, N-{3-[(1S,2S,7R,8R)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide can be prepared as follows:

f) (rac-di-exo)-3-Aza-tricyclo[4.2.1.0$^{2,5}$]nonan-4-one

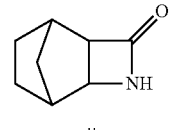

rac-di-exo

To a solution of bicyclo[2.2.1]hept-2-ene (21.29 g, 223.8 mmol) in diethyl ether (100 mL) at 0° C. was added a solution of chlorosulfonyl isocyanate (20.0 mL, 225.7 mmol) in diethyl ether (40 mL) dropwise over 10 min. The mixture was allowed to slowly warm to 25° C. for 12 h. The reaction mixture was cooled to 0° C. and a solution of sodium sulfite (39.16 g, 301.4 mmol) in water (300 mL) was added dropwise with stifling. The mixture was allowed to warm to 25° C. To this mixture was added 10% aqueous potassium hydroxide solution until the pH reached 7-8. The organic layer was separated and the aqueous layer was extracted with diethyl ether (2×100 mL). The combined organic layers were washed with aqueous saturated brine solution (100 mL), dried over anhydrous magnesium sulfate, concentrated in vacuo, and dried under high vacuum to afford the crude (rac-di-exo)-3-aza-tricyclo[4.2.1.0$^{2,5}$]nonan-4-one (23.37 g, 170.4 mmol, 76% yield) as a white solid. $^1$H NMR (400 MHz, CDCl$_3$) δ: 1.02-1.11 (2H, m), 1.24 (1H, dt, J$_1$=10.9 Hz, J$_2$=1.6 Hz), 1.51-1.72 (3H, m), 2.37-2.37 (1H, m), 2.43-2.44 (1H, m), 2.99-3.00 (1H, m), 3.40 (1H, d, J=3.4 Hz), 5.73 (1H, bs).

g) (rac-di-exo)-3-Amino-bicyclo[2.2.1]heptane-2-carboxylic acid hydrochloride

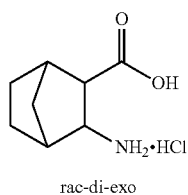

rac-di-exo

To (rac-di-exo)-3-aza-tricyclo[4.2.1.0²,⁵]nonan-4-one (23.37 g, 170.4 mmol) was added 12.0 M aqueous hydrochloric acid solution (150 mL). The mixture was stifled at 25° C. for 12 h. The solvent was evaporated in vacuo and the crude compound was dried under high vacuum for 0.5 h. The crude compound was triturated with acetone and filtered to afford (rac-di-exo)-3-amino-bicyclo[2.2.1]heptane-2-carboxylic acid hydrochloride (28.43 g, 148.3 mmol, 87% yield) as a white solid. $^1$H NMR (400 MHz, DMSO-$d_6$) δ: 1.15-1.26 (3H, m), 1.42-1.59 (2H, m), 1.87 (1H, d, J=10.3 Hz), 2.33 (1H, d, J=3.4 Hz), 2.45 (1H, d, J=2.3 Hz), 2.67 (1H, d, J=7.6 Hz), 3.23-3.26 (1H, m), 7.93 (3H, bs), 12.73 (1H, bs).

h) (rac-di-exo)-3-Amino-bicyclo[2.2.1]heptane-2-carboxylic acid ethyl ester hydrochloride

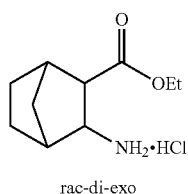

rac-di-exo

To absolute ethanol (75 mL) at −10° C. was added thionyl chloride (4.1 mL, 54.5 mmol) dropwise followed by (rac-di-exo)-3-amino-bicyclo[2.2.1]heptane-2-carboxylic acid hydrochloride (9.60 g, 50.1 mmol). The mixture was stirred at 0° C. for 1 h, at 25° C. for 4 h, and heated at reflux for 0.5 h. The solution was concentrated in vacuo and dried under high vacuum to afford the crude (rac-di-exo)-3-amino-bicyclo[2.2.1]heptane-2-carboxylic acid ethyl ester hydrochloride (11.01 g, 50.1 mmol, 100% yield) as an off-white solid. $^1$H NMR (400 MHz, DMSO-$d_6$) δ: 1.17-1.27 (3H, m), 1.21 (3H, t, J=7.0 Hz), 1.43-1.57 (2H, m), 1.91 (1H, d, J=10.0 Hz), 2.36 (1H, d, J=3.9 Hz), 2.42 (1H, d, J=3.0 Hz), 2.72 (1H, d, J=7.6 Hz), 3.28 (1H, d, J=8.3 Hz), 4.00-4.13 (2H, m), 8.06 (3H, bs).

i) (rac-di-exo)-3-Amino-bicyclo[2.2.1]heptane-2-carboxylic acid ethyl ester

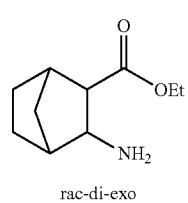 [SMILES: CCOC(=O)C1C2CCC(C2)C1N]

rac-di-exo

To (rac-di-exo)-3-amino-bicyclo[2.2.1]heptane-2-carboxylic acid ethyl ester hydrochloride (11.01 g, 50.1 mmol) was added saturated aqueous sodium bicarbonate solution (50 mL) and the mixture was stirred at 25° C. for 0.5 h. The crude product was extracted with ethyl acetate (3×100 mL). The solution was dried over anhydrous magnesium sulfate, filtered, concentrated in vacuo and dried under high vacuum for 2 h to afford the crude (rac-di-exo)-3-amino-bicyclo[2.2.1]heptane-2-carboxylic acid ethyl ester (8.17 g, 44.6 mmol, 89% yield) as a brown oil. $^1$H NMR (400 MHz, CDCl$_3$) δ: 1.10-1.26 (3H, m), 1.29 (3H, t, J=7.0 Hz), 1.45-1.62 (2H, m), 1.86 (2H, bs), 1.95 (1H, dt, J$_1$=10.3 Hz, J$_2$=1.9 Hz), 2.09 (1H, d, J=4.5 Hz), 2.49 (1H, d, J=4.2 Hz), 2.56 (1H, d, J=9.0 Hz), 3.24 (1H, d, J=7.7 Hz), 4.09-4.21 (2H, m).

j) (1R,2S,3R,4S)-3-Ethoxycarbonyl-bicyclo[2.2.1]hept-2-yl-ammonium (1'S)-(+)-10-camphorsulfonate

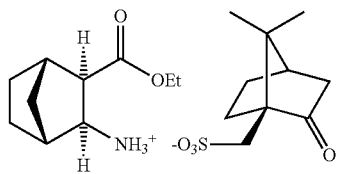

To a solution of (rac-di-exo)-3-amino-bicyclo[2.2.1]heptane-2-carboxylic acid ethyl ester (4.00 g, 21.8 mmol) in ethyl acetate (120 mL) was added (1S)-(+)-10-camphorsulfonic acid (2.57 g, 11.0 mmol). The mixture was stirred at 25° C. vigorously for 0.5 h. The solid (3.23 g, 7.77 mmol) was filtered and recrystallized in ethyl acetate (360 mL) to afford (1R,2S,3R,4S)-3-ethoxycarbonyl-bicyclo[2.2.1]hept-2-yl-ammonium (1'S)-(+)-10-camphorsulfonate (2.76 g, 6.64 mmol, 30% yield) as a white solid. $^1$H NMR (400 MHz, CDCl$_3$) δ: 0.84 (3H, s), 1.08 (3H, s), 1.30 (3H, t, J=6.9 Hz), 1.32-1.43 (4H, m), 1.58-1.75 (3H, m), 1.89 (1H, d, J=17.7 Hz), 1.95-2.07 (3H, m), 2.33 (1H, dt, J$_1$=18.4 Hz, J$_2$=3.9 Hz), 2.53 (1H, s), 2.58-2.65 (1H, m), 2.69 (1H, d, J=2.9 Hz), 2.76-2.79 (2H, m), 3.26 (1H, d, J=14.1 Hz), 3.60 (1H, d, J=7.4 Hz), 4.14-4.27 (2H, m), 7.80 (3H, bs).

k) (1S,2R,3S,4R)-3-Amino-bicyclo[2.2.1]heptane-2-carboxylic acid ethyl ester

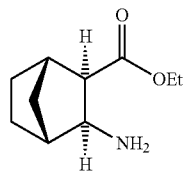

To (1R,2S,3R,4S)-3-Ethoxycarbonyl-bicyclo[2.2.1]hept-2-yl-ammonium (1'S)-(+)-10-camphorsulfonate (2.76 g, 6.64 mmol) was added ethyl acetate (28 mL) and saturated aqueous sodium carbonate solution (28 mL) and the mixture was stirred at 25° C. for 0.5 h. The organic layer was separated and the aqueous layer was extracted with ethyl acetate (2×50 mL). The solution was dried over anhydrous magnesium sulfate, concentrated in vacuo and dried under high vacuum for 1 h to afford (1S,2R,3S,4R)-3-amino-bicyclo[2.2.1]heptane-2-carboxylic acid ethyl ester (1.15 g, 6.28 mmol, 95% yield) as a colorless oil. $^1$H NMR (400 MHz, CDCl$_3$) δ: 1.10-1.26 (3H, m), 1.29 (3H, t, J=7.0 Hz), 1.45-1.62 (2H, m), 1.86 (2H, bs), 1.95 (1H, dt, J$_1$=10.3 Hz, J$_2$=1.9 Hz), 2.09 (1H, d, J=4.5 Hz), 2.49 (1H, d, J=4.2 Hz), 2.56 (1H, d, J=9.0 Hz), 3.24 (1H, d, J=7.7 Hz), 4.09-4.21 (2H, m).

In order to determine enantiomeric excess, (1S,2R,3S,4R)-3-amino-bicyclo[2.2.1]heptane-2-carboxylic acid ethyl ester was derivatized to the (S)-mandelate salt as follow: To a solution of (1S,2R,3S,4R)-3-amino-bicyclo[2.2.1]heptane-2-carboxylic acid ethyl ester (34.2 mg, 0.187 mmol) in ethyl acetate (1 mL) was added (S)-α-hydroxyphenylacetic acid (28.7 mg, 0.187 mmol) and the mixture was stirred at 25° C. for 0.5 h. The solid was filtered and dried under high vacuum to afford (1R,2S,3R,4S)-3-ethoxycarbonyl-bicyclo[2.2.1]hept-2-yl-ammonium (S)-α-hydroxyphenylacetate (11.4 mg, 0.034 mmol, 18% yield, 97% de) as a white solid. $^1$H NMR (400 MHz, CDCl$_3$) δ: 1.08-1.20 (3H, m), 1.28 (3H, t, J=7.1 Hz), 1.50-1.59 (2H, m), 1.79 (1H, d, J=10.9 Hz), 2.23 (1H, s), 2.46-2.48 (2H, m), 3.04 (1H, d, J=7.8 Hz), 4.05-4.18 (2H, m), 4.89 (1H, s), 5.49 (3H, bs), 7.22-7.31 (3H, m), 7.43 (2H, d, J=6.9 Hz).

l) (1S,2R,3S,4R)-3-(4-Fluorobenzylamino)-bicyclo[2.2.1]heptane-2-carboxylic acid ethyl ester

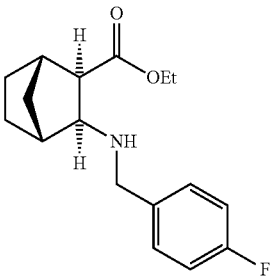

To a solution of (1S,2R,3S,4R)-3-amino-bicyclo[2.2.1]heptane-2-carboxylic acid ethyl ester (1.15 g, 6.28 mmol) in ethanol (30 mL) was added 4-fluorobenzaldehyde (0.68 mL, 6.31 mmol), glacial acetic acid (0.4 mL, 6.99 mmol), and sodium cyanoborohydride (1.04 g, 15.7 mmol) at 25° C. After stirring for 3 h, the mixture was diluted with ethyl acetate (50 mL) and quenched with saturated aqueous sodium bicarbonate (50 mL) for 0.5 h. The mixture was filtered through Celite. The organic layer was separated and the aqueous layer was extracted with ethyl acetate (50 mL×2). When all solvent was removed, a solid was formed. The solid was filtered, washed with water, and dried under vacuum to afford (1S,2R,3S,4R)-3-(4-fluorobenzylamino)-bicyclo[2.2.1]heptane-2-carboxylic acid ethyl ester (1.74 g, 5.97 mmol, 95% yield) as a white solid. $^1$H NMR (400 MHz, CDCl$_3$) δ: 1.05-1.16 (2H, m), 1.21 (1H, dt, J$_1$=8.0 Hz, J$_2$=1.6 Hz), 1.27 (3H, t, J=7.4 Hz), 1.45-1.61 (2H, m), 1.94 (1H, dt, J$_1$=10.1 Hz, J$_2$=1.9 Hz), 2.28 (1H, d, J=3.9 Hz), 2.43 (1H, d, J=3.3 Hz), 2.60 (1H, dd, J$_1$=8.8 Hz, J$_2$=1.5 Hz), 2.94 (1H, d, J=7.8 Hz), 3.66 (1H, d, J=13.2 Hz), 3.80 (1H, d, J=13.5 Hz), 4.13 (2H, q, J=7.0 Hz), 6.97 (2H, t, J=8.5 Hz), 7.26 (2H, t, J=7.1 Hz).

m) (1S,2R,3S,4R)-3-{(4-Fluorobenzyl)-[2-(7-methanesulfonylamino-1,1-dioxo-1,4-dihydro-1λ$^6$-benzo[1,2,4]thiadiazin-3-yl)-acetyl]-amino}-bicyclo[2.2.1]heptane-2-carboxylic acid ethyl ester

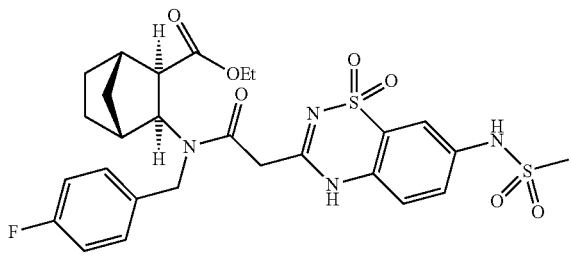

To a solution of (1S,2R,3S,4R)-3-(4-fluorobenzylamino)-bicyclo[2.2.1]heptane-2-carboxylic acid ethyl ester (100.6 mg, 0.345 mmol) in N,N-dimethylformamide (3.0 mL) was added (7-methanesulfonylamino-1,1-dioxo-1,4-dihydro-1λ$^6$-benzo[1,2,4]thiadiazin-3-yl)-acetic acid (U.S. Pat. No. 7,939,524 B2) (120.8 mg, 0.362 mmol), 4-dimethylaminopyridine (10.6 mg, 0.086 mmol), and 1-[3-(dimethylamino)propyl]-3-ethylcarbodiimide hydrochloride (70.9 mg, 0.362 mmol). After stirring at 25° C. for 12 h, the mixture was diluted with ethyl acetate and acidified with 1.0 M aqueous hydrochloric acid solution to pH 1. The organic layer was separated and the aqueous layer was extracted with ethyl acetate (2×20 mL). The combined organic layer was dried over anhydrous magnesium sulfate, filtered, concentrated in vacuo, and dried under high vacuum to afford the crude (1S,2R,3S,4R)-3-{(4-fluorobenzyl)-[2-(7-methanesulfonylamino-1,1-dioxo-1,4-dihydro-1λ$^6$-benzo[1,2,4]thiadiazin-3-yl)-acetyl]-amino}-bicyclo[2.2.1]heptane-2-carboxylic acid ethyl ester as a faintly yellow oil. The crude product was used in the next step without further purification. LC-MS (ESI) calcd for C$_{27}$H$_{31}$FN$_4$O$_7$S$_2$ (M+H$^+$) 607.17. found 607.2.

n) N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

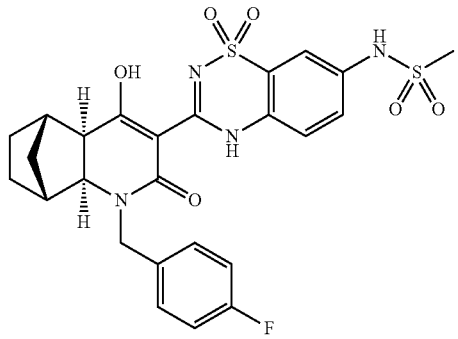 [SMILES: CS(=O)(=O)Nc1ccc2c(c1)S(=O)(=O)N=C(C1=C(O)[C@@H]3[C@H]4CC[C@H](C4)[C@@H]3N(Cc3ccc(F)cc3)C1=O)N2]

To a solution of (1S,2R,3S,4R)-3-{(4-fluorobenzyl)-[2-(7-methanesulfonylamino-1,1-dioxo-1,4-dihydro-1λ$^6$-benzo[1,2,4]thiadiazin-3-yl)-acetyl]-amino}-bicyclo[2.2.1]heptane-2-carboxylic acid ethyl ester (209.3 mg, 0.345 mmol) in absolute ethanol (3 mL) was added a 21 wt. % solution of sodium ethoxide in ethanol (0.51 mL, 1.37 mmol). After stirring at 60° C. for 2 h, the mixture was diluted with ethyl acetate and acidified with 1.0 M aqueous hydrochloric acid solution to pH 1. The organic layer was separated and the aqueous layer was extracted with ethyl acetate (2×20 mL). The combined organic layer was dried over anhydrous magnesium sulfate, filtered, and concentrated in vacuo. The crude mixture was purified by flash column chromatography (Teledyne ISCO RediSep column, 0 to 100% ethyl acetate in hexanes) to afford N-{3-[(1R,2S,7R,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (131.5 mg, 0.235 mmol, 68% yield) as an off-white solid. $^1$H NMR (400 MHz, MeOH-d$_4$) δ: 1.28 (2H, d, J=11.0 Hz), 1.47 (1H, t, J=10.8 Hz), 1.57-1.74 (3H, m), 2.56 (1H, d, J=3.2 Hz), 2.75 (1H, d, J=2.3 Hz), 2.96 (1H, d, J=9.2 Hz), 3.02 (3H, s), 3.58 (1H, d, J=9.2 Hz), 4.42 (1H, d, J=15.5 Hz), 5.03 (1H, d, J=15.7 Hz), 7.04 (2H, t, J=8.5 Hz), 7.31 (1H, dd, J$_1$=7.9 Hz, J$_2$=5.5 Hz), 7.37 (1H, d, J=8.8 Hz), 7.54 (1H, dd, J$_1$=8.3 Hz, J$_2$=2.3 Hz), 7.69 (1H, d, J=2.3 Hz). LC-MS (ESI) calcd for C$_{25}$H$_{25}$FN$_4$O$_6$S$_2$ (M+H$^+$) 561.13. found 561.4. ee=98.5% [HPLC-analysis: Chiralpak AS-RH 2.1×150 mm, 5 micron at r.t., Solvent A-Solvent B (see table above for gradient), 0.3 mL/min, 312 nm, t1=7.58 min (major), t2=8.95 min]

Example 3

(1R,2S,7R,8S)-5-(1,1-Dioxo-1,4-dihydro-1λ⁶-benzo[1,2,4]thiadiazin-3-yl)-3-(4-fluoro-benzyl)-6-hydroxy-3-aza-tricyclo[6.2.1.0$^{2,7}$]undec-5-en-4-one

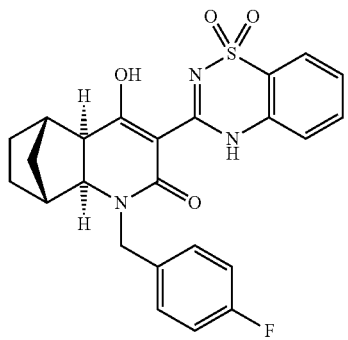

a) N-(2-Sulfamoyl-phenyl)-malonamic acid ethyl ester

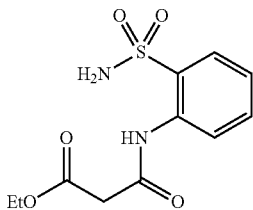 [SMILES: CCOC(=O)CC(=O)Nc1ccccc1S(N)(=O)=O]

2-Amino-benzenesulfonamide (5 g, 29 mmol) was dissolved in N,N-dimethylacetamide (25 mL) and diethyl ether (25 mL). Ethyl-3-chloro-3-oxo-propionate (4.6 g, 30.45 mmol) was added into the above reaction solution. The reaction mixture was stirred at 25° C. for 3 h. The product started to precipitate and was collected by vacuum filtration. The solid was dissolved in ethyl acetate (200 mL) and extracted with water (200 mL). The aqueous layer was back-extracted with ethyl acetate (200 mL). The combined organic layers were dried over sodium sulfate, filtered, and concentrated in vacuo to afford the crude product, N-(2-sulfamoyl-phenyl)-malonamic acid ethyl ester, as a white solid, which was used in the next step without further purification. $^1$H NMR (400 MHz, DMSO-d$_6$) δ: 1.23 (3H, t, J=7.0 Hz), 3.61 (2H, s), 4.14 (2H, quartet, J=7.0 Hz), 7.29-7.33 (1H, m), 7.53 (2H, bs), 7.56-7.60 (1H, m), 7.84-7.86 (1H, m), 7.97-7.99 (1H, m), 9.54 (1H, bs). LC-MS (ESI) calcd for C$_{11}$H$_{14}$N$_2$O$_5$S 286.06. found 287.1 [M+H$^+$].

b) (1,1-Dioxo-1,4-dihydro-1λ⁶-benzo[1,2,4]thiadiazin-3-yl)-acetic acid

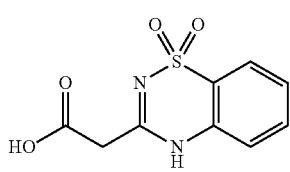 [SMILES: O=C(O)CC1=NS(=O)(=O)c2ccccc2N1]

Solid sodium hydroxide (3.48 g, 87 mmol) was dissolved in water to make a saturated solution. The crude N-(2-sulfamoyl-phenyl)-malonamic acid ethyl ester was added into the sodium hydroxide solution. The reaction mixture was heated at 110° C. for 2.5 h, and then was cooled down to 25° C. The reaction mixture was acidified by slowly adding a 12.0 M aqueous hydrochloric acid solution (9.67 g, 116 mmol) while cooling in an ice-water bath. The product precipitated and was collected by vacuum filtration. The solid was washed with cold water and dried under high vacuum to afford the crude product, (1,1-dioxo-1,4-dihydro-1λ⁶-benzo[1,2,4]thiadiazin-3-yl)-acetic acid (5 g, 20.8 mmol, 71.7% over two steps), as a white solid. $^1$H NMR (400 MHz, DMSO-d$_6$) δ: 3.58 (2H, s), 7.31 (1H, d, J=8.0 Hz), 7.44 (1H, dd, J$_1$=7.8 Hz, J$_2$=7.8 Hz), 7.67 (1H, dd, J$_1$=7.8 Hz, J$_2$=7.8 Hz), 7.79 (1H, d, J=7.9 Hz), 12.18 (1H, bs), 13.03 (1H, bs). LC-MS (ESI) calcd for C$_9$H$_8$N$_2$O$_4$S 240.02. found 241.1 [M+H$^+$].

c) (1S,2R,3S,4R)-3-[[2-(1,1-Dioxo-1,4-dihydro-1λ⁶-benzo[1,2,4]thiadiazin-3-yl)-acetyl]-(4-fluoro-benzyl)-amino]-bicyclo[2.2.1]heptane-2-carboxylic acid ethyl ester

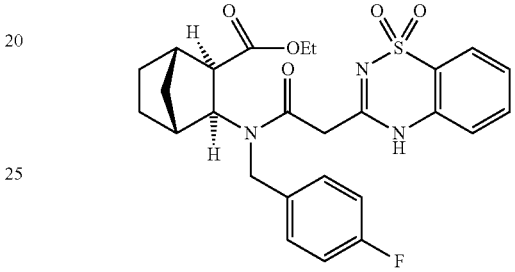

(1,1-Dioxo-1,4-dihydro-1λ⁶-benzo[1,2,4]thiadiazin-3-yl)-acetic acid (0.2 g, 0.833 mmol) was dissolved in anhydrous N,N-dimethylformamide (8 mL). (1S,2R,3S,4R)-3-(4-Fluoro-benzylamino)-bicyclo[2.2.1]heptane-2-carboxylic acid ethyl ester (prepared as described in Example 21, 0.244 g, 0.833 mmol) was added followed by 1-(3-dimethylaminopropyl)-3-ethylcarbodiimide hydrochloride (0.168 g, 0.875 mmol). Then N-methylmorpholine (0.177 g, 1.75 mmol) was added into the above reaction mixture. The mixture was stirred at 25° C. for 16 h. The solution was poured into 1.0 M aqueous hydrochloric acid solution (100 mL). The aqueous layer was extracted with ethyl acetate (2×100 mL). The organic layer was dried over sodium sulfate, filtered, and concentrated in vacuo to afford the crude product, (1S,2R,3S,4R)-3-[[2-(1,1-dioxo-1,4-dihydro-1λ⁶-benzo[1,2,4]thiadiazin-3-yl)-acetyl]-(4-fluoro-benzyl)-amino]-bicyclo[2.2.1]heptane-2-carboxylic acid ethyl ester, as an orange oil, which was used in the next step without any further purification. LC-MS (ESI) calcd for C$_{26}$H$_{28}$FN$_3$O$_5$S 513.58. found 514.4 [M+H+].

d) (1R,2S,7R,8S)-5-(1,1-Dioxo-1,2-dihydro-1λ⁶-benzo[1,2,4]thiadiazin-3-yl)-3-(4-fluoro-benzyl)-6-hydroxy-3-aza-tricyclo[6.2.1.0$^{2,7}$]undec-5-en-4-one

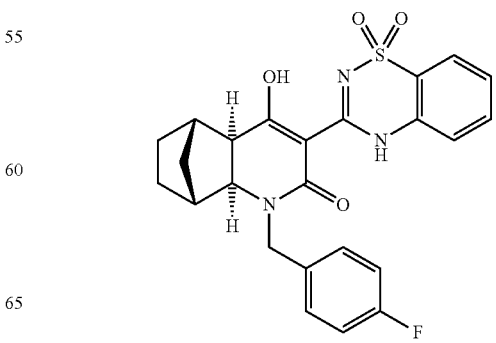

The crude (1S,2R,3S,4R)-3-[[2-(1,1-dioxo-1,4-dihydro-1λ⁶-benzo[1,2,4]thiadiazin-3-yl)-acetyl]-(4-fluoro-benzyl)-amino]-bicyclo[2.2.1]heptane-2-carboxylic acid ethyl ester was dissolved in ethanol (8 mL), and a 21 wt. % solution of sodium ethoxide in ethanol (1.6 mL, 4.2 mmol) was added into the above solution. The mixture was stirred at 60° C. for 4 h and allowed to cool down to 25° C. The mixture was poured into 0.5 M aqueous hydrochloric acid solution (100 mL). The product started to precipitate and was collected by vacuum filtration. The precipitate was purified by flash column chromatography (Teledyne Isco RediSep column; 100% ethyl acetate) to afford the desired product, (1R,2S,7R,8S)-5-(1,1-dioxo-1,2-dihydro-1λ⁶-benzo[1,2,4]thiadiazin-3-yl)-3-(4-fluoro-benzyl)-6-hydroxy-3-aza-tricyclo[6.2.1.0²,⁷]undec-5-en-4-one (0.242 g, 0.517 mmol, 62.1% over two steps), as a white solid. ¹H NMR (400 MHz, DMSO-d₆) δ: 1.16-1.22 (2H, m), 1.40-1.60 (4H, m), 2.51 (1H, bs), 2.64 (1H, d, J=2.1 Hz), 3.03 (1H, d, J=8.0 Hz), 3.54 (1H, d, J=9.3 Hz), 4.42 (1H, d, J=15.6 Hz), 4.97 (1H, d, J=15.7 Hz), 7.15 (2H, t, J=8.8 Hz), 7.33 (2H, dd, J₁=8.0 Hz, J₂=5.9 Hz), 7.45-7.53 (2H, m), 7.67-7.71 (1H, m), 7.85 (1H, d, J=7.9 Hz). LC-MS (ESI) calcd for C₂₄H₂₂FN₃O₄S 467.13. found 468.2 [M+H⁺]. Anal. calcd for C₂₄H₂₂FN₃O₄S: C, 61.66; H, 4.74; N, 8.99; found C, 61.96; H, 4.88; N, 8.99.

Scheme 3 provides a specific procedure that was used to prepare the 5,6-dihydro-1H-pyridin-2-one compound of Example 4.

Scheme 3

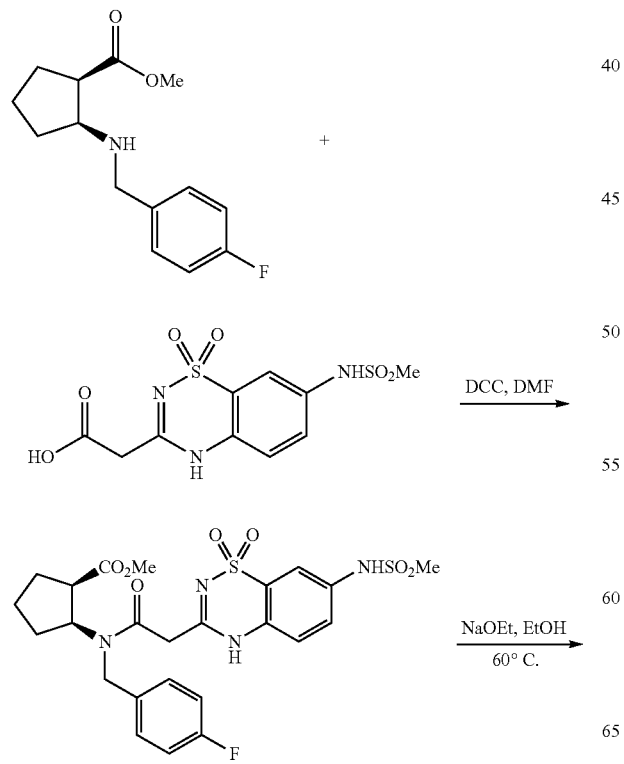

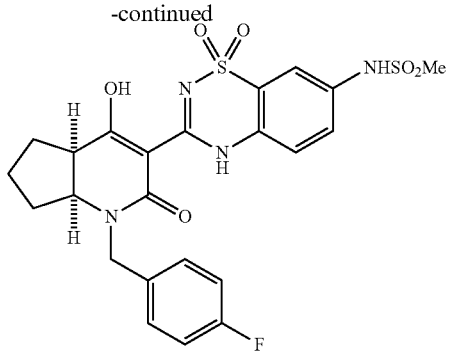

Example 4

(4aR,7aS)—N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide

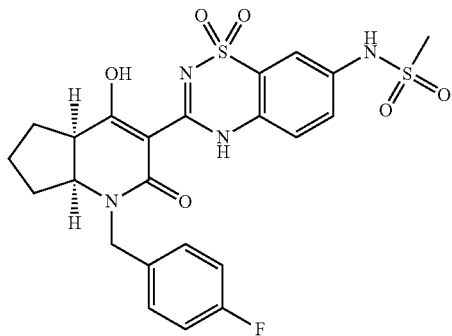 [SMILES: CS(=O)(=O)Nc1ccc2c(c1)S(=O)(=O)N=C(C1=C(O)[C@@H]3CCC[C@@H]3N(Cc3ccc(F)cc3)C1=O)N2]

a) (1R,2S)-2-Amino-cyclopentanecarboxylic acid methyl ester hydrochloride

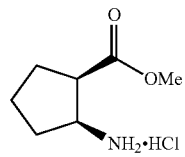

(1R,2S)-2-Amino-cyclopentanecarboxylic acid hydrochloride (96 mg, 0.58 mmol) was dissolved in a 1:1 mixture of benzene and methanol (6 mL). The mixture was cooled to 0° C. A 2.0 M solution of (trimethylsilyl)diazomethane in hexanes (0.44 mL, 0.87 mmol) was added and the reaction was stirred at 25° C. for 30 min. The mixture was concentrated and dried in vacuo. The crude product was directly used in the next step.

b) (1R,2S)-2-(4-Fluoro-benzylamino)-cyclopentanecarboxylic acid methyl ester

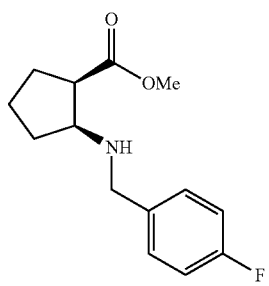 [SMILES: COC(=O)[C@@H]1CCC[C@@H]1NCc1ccc(F)cc1]

To a solution of (1R,2S)-2-amino-cyclopentanecarboxylic acid methyl ester hydrochloride (104 mg, 0.58 mmol) in tetrahydrofuran (6 mL) at 25° C. was added magnesium sulfate (200 mg), triethylamine (0.085 mL, 0.61 mmol), and 4-fluorobenzaldehyde (0.13 mL, 1.19 mmol) sequentially. The reaction was stirred at 25° C. for 16 h. The mixture was passed through a short pad of Celite and the filtrate was concentrated and dried in vacuo. The residue was re-dissolved in methanol (10 mL) at 25° C. To this solution was added slowly sodium borohydride (45 mg, 1.19 mmol). The mixture was stirred at 25° C. for 1 h. It was then poured into a saturated sodium bicarbonate aqueous solution (10 mL) and the mixture was extracted into ethyl acetate (20 mL). The organic layer was dried over magnesium sulfate, filtered, and concentrated in vacuo to afford a clear oil. Purification by flash column chromatography (Merck silica gel 60, 40-63 μm; 0-15% ethyl acetate in hexanes) afforded the desired product, (1R,2S)-2-(4-fluoro-benzylamino)-cyclopentanecarboxylic acid methyl ester (116 mg, 0.46 mmol, 79%), as a clear oil. $^1$H NMR (400 MHz, CDCl$_3$) δ: 1.55-1.73 (2H, m), 1.83-1.93 (3H, m), 1.99-2.08 (1H, m), 2.97 (1H, dd, $J_1$=14.4 Hz, $J_2$=8.0 Hz), 3.31 (1H, dd, $J_1$=14.4 Hz, $J_2$=7.2 Hz), 3.70 (3H, s), 3.77 (2H, dd, $J_1$=19.6 Hz, $J_2$=12.0 Hz), 4.67 (1H, s), 6.96-7.06 (2H, m), 7.26-7.35 (2H, m). LC-MS (ESI) calcd for $C_{14}H_{18}FNO_2$ 251.30. found 252.1 [M+H$^+$].

c) (1R,2S)-2-{(4-Fluoro-benzyl)-[2-(7-methanesulfonylamino-1,1-dioxo-1,4-dihydro-1λ$^6$-benzo[1,2,4]thiadiazin-3-yl)-acetyl]-amino}-cyclopentanecarboxylic acid methyl ester

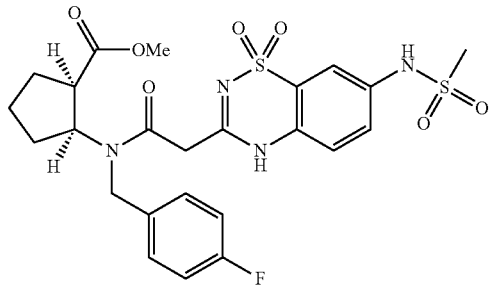 [SMILES: COC(=O)[C@@H]1CCC[C@@H]1N(Cc1ccc(F)cc1)C(=O)CC1=NS(=O)(=O)c2cc(NS(C)(=O)=O)ccc2N1]

(1R,2S)-2-(4-Fluoro-benzylamino)-cyclopentanecarboxylic acid methyl ester (106 mg, 0.42 mmol) and (7-methanesulfonylamino-1,1-dioxo-1,4-dihydro-1λ$^6$-benzo[1,2,4]thiadiazin-3-yl)-acetic acid (prepared as described in U.S. Pat. No. 7,939,524 B2, 140 mg, 0.42 mmol) were dissolved in a 1:1 mixture of dichloromethane and N,N'-dimethylformamide (6 mL). A 1.0 M solution of N,N'-dicyclohexylcarbodiimide in dichloromethane (0.46 mL, 0.46 mmol) was added. The reaction was stirred at 25° C. for 16 h. The mixture was concentrated in vacuo and purified by flash column chromatography (Merck silica gel 60, 40-63 μm; 0-85% ethyl acetate in hexanes) to afford the desired product, (1R,2S)-2-{(4-fluoro-benzyl)-[2-(7-methanesulfonylamino-1,1-dioxo-1,4-dihydro-1λ$^6$-benzo[1,2,4]thiadiazin-3-yl)-acetyl]-amino}-cyclopentanecarboxylic acid methyl ester (127 mg, 0.22 mmol, 52%), as a white solid. $^1$H NMR (400 MHz, CDCl$_3$) δ: 1.80-2.22 (6H, m), 3.07 (3H, s), 3.24 (1H, dd, $J_1$=18.8 Hz, $J_2$=8.0 Hz), 3.32 (1H, dd, $J_1$=15.6 Hz, $J_2$=8.0 Hz), 3.69 (1H, s), 4.63 (2H, d, J=4.8 Hz), 4.67-4.74 (1H, m), 4.82-4.89 (1H, m), 6.99-7.14 (5H, m), 7.51-7.64 (2H, m). LC-MS (ESI) calcd for $C_{24}H_{27}FN_4O_7S_2$ 566.62. found 567.1 [M+H$^+$].

d) (4aR,7aS)—N-{3-[1-(4-Fluoro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide

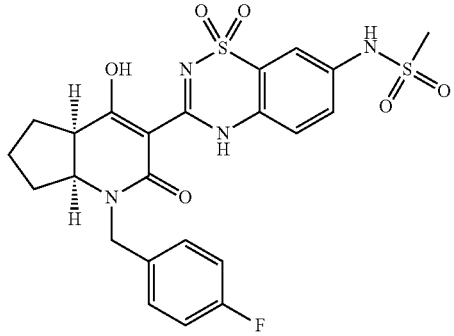 [SMILES: CS(=O)(=O)Nc1ccc2c(c1)S(=O)(=O)N=C(C1=C(O)[C@@H]3CCC[C@@H]3N(Cc3ccc(F)cc3)C1=O)N2]

(1R,2S)-2-{(4-Fluoro-benzyl)-[2-(7-methanesulfonylamino-1,1-dioxo-1,4-dihydro-1λ$^6$-benzo[1,2,4]thiadiazin-3-yl)-acetyl]-amino}-cyclopentanecarboxylic acid methyl ester (117 mg, 0.21 mmol) was dissolved in ethanol (10 mL). A 21% w/w solution of sodium ethoxide in ethanol (0.17 mL, 0.46 mmol) was added and the mixture was stirred at 60° C. for 4 h. The reaction was allowed to cool to 25° C. and quenched with 1.0 M aqueous hydrochloric acid solution (10 mL). The mixture was extracted with ethyl acetate (3×20 mL). The organic layers were combined, dried over magnesium sulfate, filtered, and concentrated in vacuo. The crude material was purified by flash column chromatography (Merck silica gel 60, 40-63 μm; 0-5% methanol in dichloromethane) to afford the desired product, (4aR,7aS)—N-{3-[1-(4-fluoro-benzyl)-4-hydroxy-2-oxo-2,4a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide (80 mg, 0.15 mmol, 71%), as a white solid. $^1$H NMR (400 MHz, DMSO-d$_6$) δ: 1.46-1.61 (4H, m), 1.95-2.12 (2H, m), 3.07 (3H, s), 3.85 (1H, bs), 4.48 (1H, bs), 4.91 (1H, d, J=14.8 Hz), 7.16 (2H, t, J=8.4 Hz), 7.40 (2H, bs), 7.50-7.61 (3H, m), 10.18 (1H, s). LC-MS (ESI) calcd for $C_{23}H_{23}FN_4O_6S_2$ 534.58. found 535.1 [M+H$^+$]. e.e.=98% [HPLC-analysis: Chiralpak AS-RH 4.6×250 mm, 5 micron at 25° C., 0.7 mL/min, 310 nm, t1=14.89 min, t2=22.20 min (major)]. α$_D$=−40.76 (c=0.92, dichloromethane/methanol 1:1). Anal. calcd for $C_{23}H_{23}FN_4O_6S_2$.0.3 $H_2O$.0.3 EtOAc.0.2 $Et_2O$: C, 51.66; H, 4.86; N, 9.64. found C, 51.64; H, 4.90; N, 9.56.

Example 5

N-[3-(1R,2S,7R,8S)-3-Cyclopentyl-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl]-methanesulfonamide

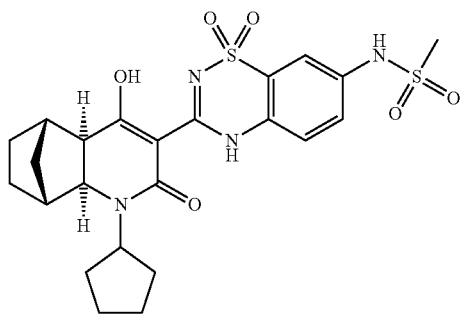

a) (1S,2R,3S,4R)-3-Cyclopentylamino-bicyclo[2.2.1]heptane-2-carboxylic acid ethyl ester

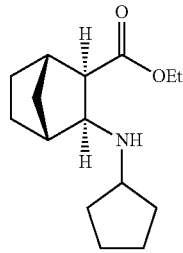 [SMILES: CCOC(=O)[C@@H]1[C@H]2CC[C@H](C2)[C@@H]1NC1CCCC1]

Cyclopentanone (0.12 mL, 1.38 mmol) was added to a solution of (1S,2R,3S,4R)-3-amino-bicyclo[2.2.1]heptane-2-carboxylic acid ethyl ester (prepared as described in Example 2k, 230 mg, 1.26 mmol) in anhydrous methanol (10 mL) at 25° C. under a nitrogen atmosphere. After stirring for 10 min, glacial acetic acid (0.5 mL) and sodium cyanoborohydride (260 mg, 3.15 mmol) were added sequentially, and the resulting mixture was stirred at 50° C. for 30 min. The reaction mixture was poured into saturated aqueous sodium bicarbonate solution and extracted with ethyl acetate. The combined organic layers were washed with saturated aqueous brine solution, dried over sodium sulfate and filtered. The filtrate was concentrated in vacuo to afford the desired product, (1S,2R,3S,4R)-3-cyclopentylamino-bicyclo[2.2.1]heptane-2-carboxylic acid ethyl ester (237 mg, 0.94 mmol, 75%), as a yellow oil. LC-MS (ESI) calcd for $C_{15}H_{25}NO_2$ 251.19. found 252.0 [M+H$^+$].

b) N-[3-(1R,2S,7R,8S)-3-Cyclopentyl-6-hydroxy-4-oxo-3-aza-tricyclo[6.2.1.0$^{2,7}$]undec-5-en-5-yl)-1,1-dioxo-1,4-dihydro-1λ$^6$-benzo[1,2,4]thiadiazin-7-yl]-methanesulfonamide

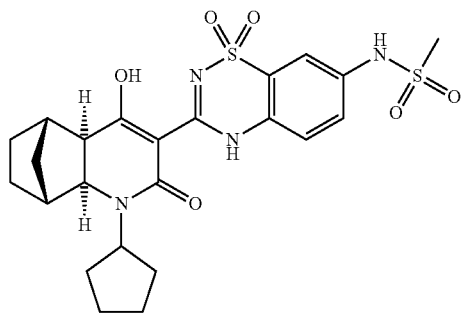

To a stirred solution of (1S,2R,3S,4R)-3-cyclopentylamino-bicyclo[2.2.1]heptane-2-carboxylic acid ethyl ester (150 mg, 0.60 mmol) and (7-methanesulfonylamino-1,1-dioxo-1,4-dihydro-1λ$^6$-benzo[1,2,4]thiadiazin-3-yl)-acetic acid (prepared as described in U.S. Pat. No. 7,939,524 B2, 181 mg, 0.54 mmol) in anhydrous N,N-dimethylformamide (5 mL) under a nitrogen atmosphere, N-methylmorpholine (0.12 mL, 1.08 mmol) and 1-(3-dimethylaminopropyl)-3-ethylcarbodiimide hydrochloride (104 mg, 0.54 mmol) were added sequentially. The mixture was stirred at 25° C. for 45 min, triethylamine (0.25 mL, 1.76 mmol) was added and the resulting mixture was stirred at 50° C. for 60 h. The reaction mixture was allowed to cool to 25° C., diluted with ethyl acetate, washed with 1.0 M aqueous hydrochloric acid solution and saturated aqueous brine solution, dried over magnesium sulfate and filtered. The filtrate was concentrated in vacuo and the residue was purified by prep-HPLC [Column Luna 5µ C18 (2) 100 Å AXIA 150×21.2 mm, 5 micron, 30%-95% in 7 min @ 30 mL/min flow rate, 0.05% trifluoroacetic acid in acetonitrile/0.05% trifluoroacetic acid in water] to afford the desired product, N-[3-(1R,2S,7R,8S)-3-cyclopentyl-6-hydroxy-4-oxo-3-aza-tricyclo[6.2.1.0$^{2,7}$]undec-5-en-5-yl)-1,1-dioxo-1,4-dihydro-1λ$^6$-benzo[1,2,4]thiadiazin-7-yl]-methanesulfonamide (80 mg, 0.15 mmol, 26%), as a yellow solid. $^1$H NMR (400 MHz, DMSO-d$_6$) δ: 1.20-1.65 (8H, m), 1.75-1.95 (6H, m), 2.42 (1H, s), 2.60 (1H, s), 2.99 (1H, d, J=9.2 Hz), 3.05 (3H, s), 3.60 (1H, d, J=9.2 Hz), 3.93 (1H, m), 7.48-7.58 (3H, m), 10.17 (1H, s). LC-MS (ESI) calcd for $C_{23}H_{28}N_4O_6S_2$ 520.15. found 521.4 [M+H$^+$].

Example 6

(1R,2S,7R,8S)-5-(7-Amino-1,1-dioxo-1,4-dihydro-1λ$^6$-benzo[1,2,4]thiadiazin-3-yl)-3-(4-fluoro-benzyl)-6-hydroxy-3-aza-tricyclo[6.2.1.0$^{2,7}$]undec-5-en-4-one

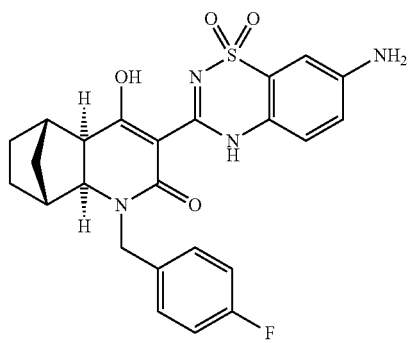

a) (1R,2S,7R,8S)-5-(7-Azido-1,1-dioxo-1,4-dihydro-1λ$^6$-benzo[1,2,4]thiadiazin-3-yl)-3-(4-fluoro-benzyl)-6-hydroxy-3-aza-tricyclo[6.2.1.0$^{2,7}$]undec-5-en-4-one

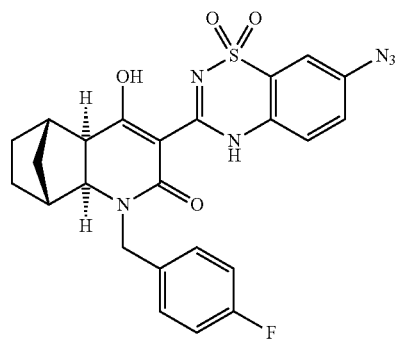

(1R,2S,7R,8S)-3-(4-Fluoro-benzyl)-6-hydroxy-5-(7-iodo-1,1-dioxo-1,4-dihydro-1λ$^6$-benzo[1,2,4]thiadiazin-3-yl)-3-aza-tricyclo[6.2.1.0$^{2,7}$]undec-5-en-4-one (prepared as described in Example 1a, 0.513 g, 0.864 mmol), sodium azide (1.12 g, 17.2 mmol), sodium ascorbate (0.086 g, 0.43 mmol), copper (I) iodide (0.16 g, 0.84 mmol), and trans-N,N'-dimethylcyclohexane-1,2-diamine (0.20 mL, 1.27 mmol) were dissolved in a 5:1 mixture of dimethyl sulfoxide and water (10 mL) at 25° C. The reaction flask was degassed and backfilled with nitrogen (5×). After stirring at 25° C. for 14 h, the reaction mixture was partitioned between water (150 mL) and ethyl acetate (2×150 mL). The organic layer was dried over sodium sulfate, filtered and concentrated in vacuo. The residue was purified by flash column chromatography (Teledyne Isco RediSep column; 0 to 60% ethyl acetate in hexanes) to afford the desired product, (1R,2S,7R,8S)-5-(7-azido-1,1-dioxo-1,4-dihydro-1λ⁶-benzo[1,2,4]thiadiazin-3-yl)-3-(4-fluoro-benzyl)-6-hydroxy-3-aza-tricyclo[6.2.1.0²,⁷]undec-5-en-4-one (0.348 g, 0.684 mmol, 79%), as a dark brown foam, which was used in the next step without any further purification.

b) (1R,2S,7R,8S)-5-(7-Amino-1,1-dioxo-1,4-dihydro-1λ⁶-benzo[1,2,4]thiadiazin-3-yl)-3-(4-fluoro-benzyl)-6-hydroxy-3-aza-tricyclo[6.2.1.0²,⁷]undec-5-en-4-one

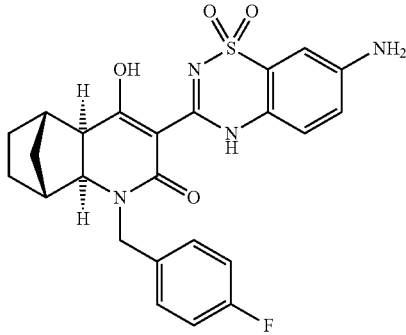

(1R,2S,7R,8S)-5-(7-Azido-1,1-dioxo-1,4-dihydro-1λ⁶-benzo[1,2,4]thiadiazin-3-yl)-3-(4-fluoro-benzyl)-6-hydroxy-3-aza-tricyclo[6.2.1.0²,⁷]undec-5-en-4-one (0.348 g, 0.684 mmol) was dissolved in a 1:1 mixture of methanol and ethyl acetate (15 mL) at 25° C. Palladium on carbon (0.40 g, 5%, "wet") was added, resulting in a black suspension. The reaction was maintained under a hydrogen atmosphere (balloon) at 25° C. for 6 h, and then was filtered through Celite. The Celite was washed with ethyl acetate (2×30 mL) and the filtrate was concentrated in vacuo. The residue was purified by flash column chromatography (Teledyne Isco RediSep column; 50 to 100% ethyl acetate in hexanes) to afford the desired product, (1R,2S,7R,8S)-5-(7-amino-1,1-dioxo-1,4-dihydro-1λ⁶-benzo[1,2,4]thiadiazin-3-yl)-3-(4-fluoro-benzyl)-6-hydroxy-3-aza-tricyclo[6.2.1.0²,⁷]undec-5-en-4-one (0.159 g, 0.330 mmol, 48%), as a pale yellow solid. $^1$H NMR (400 MHz, CDCl$_3$) δ: 1.08-1.19 (3H, m), 1.40-1.57 (3H, m), 2.99 (1H, d, J=7.2 Hz), 3.31 (3H, s), 3.36-3.37 (1H, m), 3.50 (1H, d, J=7.8 Hz), 4.39 (1H, d, J=14.6 Hz), 4.93 (1H, d, J=14.5 Hz), 6.86-6.91 (3H, m), 7.13-7.15 (2H, m), 7.21 (1H, d, J=8.8 Hz), 7.30 (2H, bs), 13.79 (1H, s). LC-MS (ESI) calcd for C$_{24}$H$_{23}$FN$_4$O$_4$S 482.14. found 483.4 [M+H$^+$].

Example 7

N-{3-[(1S,2R,7S,8R)-3-(4-Fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-yl}-methanesulfonamide

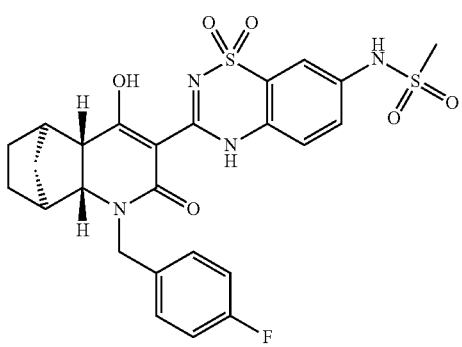

a) (1R,2R,3S,4S)-3-(Methoxycarbonyl)bicyclo[2.2.1]hept-5-ene-2-carboxylic acid

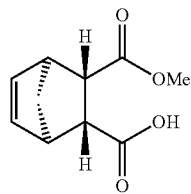

This compound was prepared as described in *J. Org. Chem.* 2000, 65, 6984-6991. cis-5-Norbornene-exo-2,3-dicarboxylic anhydride (5 g, 30.45 mmol) was suspended in a 1:1 mixture of toluene and carbon tetrachloride (150 mL). The mixture was stirred for 10 min. Quinidine (10.9 g, 33.5 mmol) was added and the flask was degassed and backfilled with nitrogen. The solution was cooled to −55° C. While stirring, methanol (3.7 mL, 91.35 mmol) was added. The mixture was stirred at −55° C. for 16 h. Upon warming to 25° C., the mixture was concentrated in vacuo to a foam. The foam was dissolved in a mixture of ethyl acetate (400 mL) and 1.0 M aqueous hydrochloric acid solution (400 mL). The layers were separated and the organic layer was further washed with 1.0 M aqueous hydrochloric acid solution (2×100 mL), saturated aqueous brine solution (100 mL) and dried over magnesium sulfate, filtered, and concentrated in vacuo to afford the desired product, (1R,2R,3S,4S)-3-(methoxycarbonyl)bicyclo[2.2.1]hept-5-ene-2-carboxylic acid (5.92 g, 30.2 mmol, 99%), as a clear oil. $^1$H NMR (400 MHz, DMSO-d$_6$) δ: 1.29 (1H, d, J=10.2 Hz), 1.96 (1H, d, J=8.6 Hz), 2.47-2.49 (2H, m), 2.93-2.94 (2H, m), 3.51 (3H, s), 6.15-6.20 (2H, m), 12.15 (1H, s).

b) Methyl (1S,2S,3R,4R)-3-{[(benzyloxy)carbonyl]amino}bicyclo[2.2.1]hept-5-ene-2-carboxylate

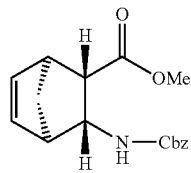

This intermediate was prepared as described in *Synthesis* 2001, 11, 1719-1730. (1R,2R,3S,4S)-3-(Methoxycarbonyl)bicyclo[2.2.1]hept-5-ene-2-carboxylic acid (5.9 g, 30 mmol) was dissolved in anhydrous tetrahydrofuran (133 mL). The flask was degassed and backfilled with nitrogen and the mixture was cooled to 0° C. Triethylamine (12.64 mL, 90 mmol) was added followed by the dropwise addition of ethyl chloroformate (5.72 mL, 60 mmol) with vigorous stifling. Immediate precipitation was observed. The mixture was stirred at 0° C. for 1 h. Sodium azide (5.86 g, 90 mmol) was dissolved in water (40 mL) and added to the reaction mixture at 0° C. The mixture was stirred at 0° C. for 5 min. The ice bath was removed. The mixture was warmed to 25° C. and continued to stir for 2 h. The mixture was poured into water (300 mL) and the product extracted into ethyl acetate (350 mL). The organic layer was further washed with half-saturated aqueous sodium bicarbonate solution (2×100 mL), saturated aqueous brine solution (100 mL), dried over magnesium sulfate, filtered, and concentrated in vacuo to afford a light brown oil.

The oil was dissolved in anhydrous benzene (66 mL) and refluxed while stirring under nitrogen for 2 h. Upon cooling to 25° C. the solution was concentrated in vacuo to afford a light yellow oil. The oil was dissolved in dichloromethane (40 mL) and benzyl alcohol (3.41 mL, 33 mmol) was added followed by triethylamine (8.44 mL, 60 mmol). The mixture was refluxed under nitrogen for 16 h. Upon cooling to 25° C. the solution was concentrated in vacuo to afford a thick oil. Purification by flash column chromatography (Merck silica gel 60, 40-63 μm; $1^{st}$ column: 3:1 hexanes/ethyl acetate; $2^{nd}$ column: 2:4:1 dichloromethane/pentane/diethyl ether) afforded the desired product, methyl (1S,2S,3R,4R)-3-{[(benzyloxy)carbonyl]amino}bicyclo[2.2.1]hept-5-ene-2-carboxylate (6.195 g, 20.58 mmol, 69%), as a faintly yellow oil. $^1$H NMR (400 MHz, CDCl$_3$) δ: 1.60 (1H, d, J=9.4 Hz), 1.97 (1H, d, J=9.3 Hz), 2.66 (1H, d, J=7.5 Hz), 2.75 (1H, s), 2.96 (1H, s), 3.60 (3H, s), 4.02 (1H, t, J=8.9 Hz), 5.09 (2H, q, J=10.5 Hz), 5.47 (1H, d, J=8.8 Hz), 6.18-6.23 (2H, m), 7.29-7.37 (5H, m). LC-MS (ESI) calcd for $C_{17}H_{19}NO_4$ 301.13. found 258.1 (100%), 302.2 [M+H$^+$] (70%), 603.4 [2M+H$^+$] (20%).

c) Methyl (1R,2S,3R,4S)-3-aminobicyclo[2.2.1]heptane-2-carboxylate hydrochloride

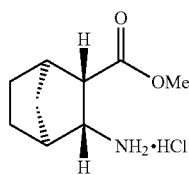

Methyl (1S,2S,3R,4R)-3-{[(benzyloxy)carbonyl]amino}bicyclo[2.2.1]hept-5-ene-2-carboxylate (1 g, 3.32 mmol) was dissolved in ethyl acetate (15 mL). 5% Palladium on carbon (120 mg) was added. The flask was degassed and backfilled with hydrogen gas via balloon. The mixture was stirred at 25° C. for 16 h. The mixture was passed through a plug of Celite and the filtrate was concentrated in vacuo to afford a thick clear oil. The oil was dissolved in diethyl ether (10 mL) and added dropwise, with vigorous stirring, to a mixture of 4.0 M hydrochloric acid solution in 1,4-dioxane (1.8 mL, 7.2 mmol) in diethyl ether (18 mL). The desired product began to precipitate as a white solid. Additional diethyl ether (10 mL) was added and the mixture was stirred for 10 min The precipitate was collected by vacuum filtration and washed with additional diethyl ether (2×8 mL). The solid was further dried in vacuo for 1 h to afford the desired product, methyl (1R,2S,3R,4S)-3-aminobicyclo[2.2.1]heptane-2-carboxylate hydrochloride (0.554 g, 2.7 mmol, 81%), as a white powder. $^1$H NMR (400 MHz, DMSO-d$_6$) δ: 1.18-1.27 (3H, m), 1.37-1.61 (2H, m), 1.90 (1H, d, J=11.0 Hz), 2.35 (1H, d, J=3.8 Hz), 2.44 (1H, d, J=3.1 Hz), 2.75 (1H, d, J=8.7 Hz), 3.29-3.34 (1H, m), 3.61 (3H, s), 8.03 (3H, bs). LC-MS (ESI) calcd for $C_9H_{15}NO_2$ (free amine) 169.11. found 170.3 [M+H$^+$] (100%), 339.3 [2M+H$^+$] (50%).

d) Methyl (1R,2S,3R,4S)-3-[(4-fluorobenzyl)amino]bicyclo[2.2.1]heptane-2-carboxylate

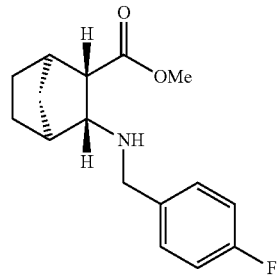

Methyl (1R,2S,3R,4S)-3-aminobicyclo[2.2.1]heptane-2-carboxylate hydrochloride (0.5 g, 2.43 mmol) was dissolved in methanol (12 mL). Sodium acetate (0.4 g, 4.86 mmol) was added followed by 4 Å powdered molecular sieves (0.5 g) and 4-fluoro-benzaldehyde (0.302 g, 2.43 mmol). Sodium cyanoborohydride (0.305 g, 4.86 mmol) was added and the mixture was stirred at 25° C. for 3 h. The mixture was poured into ethyl acetate (300 mL) and shaken with saturated aqueous sodium bicarbonate solution (200 mL). Both layers were passed through a plug of Celite. The organic layer was further washed with saturated aqueous sodium bicarbonate solution (100 mL), saturated aqueous brine solution (100 mL), dried over magnesium sulfate, filtered, and concentrated in vacuo to afford the crude product, methyl (1R,2S,3R,4S)-3-[(4-fluorobenzyl)amino]bicyclo[2.2.1]heptane-2-carboxylate (0.675 g, 2.43 mmol, 99%), as a clear oil. LC-MS (ESI) calcd for $C_{16}H_{20}FNO_2$ 277.15. found 278.2 [M+H$^+$].

e) N-{3-[(1S,2R,7S,8R)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

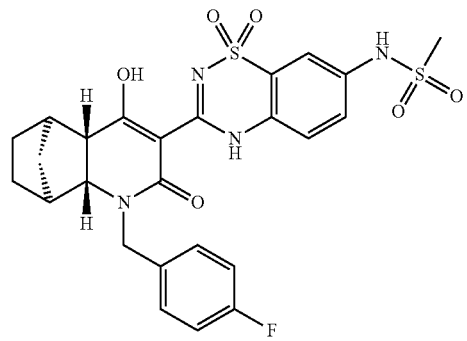

Methyl (1R,2S,3R,4S)-3-[(4-fluorobenzyl)amino]bicyclo[2.2.1]heptane-2-carboxylate (0.6 g, 2.16 mmol) was dissolved in anhydrous N,N-dimethylformamide (20 mL). (7-Methanesulfonylamino-1,1-dioxo-1,4-dihydro-1λ$^6$-benzo[1,2,4]thiadiazin-3-yl)-acetic acid (prepared as described in U.S. Pat. No. 7,939,524 B2, 0.72 g, 2.16 mmol) was added followed by N-methylmorpholine (0.5 mL, 4.54 mmol). The mixture was stirred until everything dissolved, approximately 5 min 1-(3-Dimethylaminopropyl)-3-ethylcarbodiimide hydrochloride (0.435 g, 2.27 mmol) was added and the mixture was stirred at 25° C. for 45 min Triethylamine (0.91 mL, 6.48 mmol) was added and the mixture was stirred at 50° C. for 16 h. Upon cooling to 25° C., the solution was diluted with ethyl acetate (300 mL) and washed with 1.0 M aqueous hydrochloric acid solution (3×300 mL), saturated aqueous brine solution (100 mL), dried over magnesium sulfate, filtered, and concentrated in vacuo to afford a golden oil.

Purification by flash column chromatography (Merck silica gel 60, 40-63 μm, 0 to 0.75% methanol in dichloromethane) afforded the product as white foam. The foam was dissolved in methanol (10 mL) and the product was precipitated by the addition of 1.0 M aqueous hydrochloric acid solution (20 mL) while stirring. The solid was collected by vacuum filtration and further dried in vacuo to afford the desired product, N-{3-[(1S,2R,7S,8R)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (0.592 g, 1.06 mmol, 49%), as a white powder. $^1$H NMR (400 MHz, DMSO-d$_6$) δ: 1.15-1.22 (2H, m), 1.39-1.61 (4H, m), 2.49-2.55 (1H, m), 2.62-2.63 (1H, m), 3.02 (1H, d, J=9.8 Hz), 3.05 (3H, s), 3.52 (1H, d, J=9.3 Hz), 4.41 (1H, d, J=15.5 Hz), 4.95 (1H, d, J=15.5 Hz), 7.14 (2H, t, J=8.7 Hz), 7.32 (2H, dd, J$_1$=8.2 Hz, J$_2$=5.7 Hz), 7.50 (1H, dd, J$_1$=8.4 Hz, J$_2$=2.4 Hz), 7.55-7.57 (2H, m), 10.17 (1H, s). LC-MS (ESI) calcd for C$_{25}$H$_{25}$FN$_4$O$_6$S$_2$ 560.12. found 561.3 [M+H$^+$]. ee=96% [HPLC-analysis: Chiralpak AS-RH 2.1×150 mm, 5 micron at r.t., Solvent A-Solvent B (see table above for gradient), 0.3 mL/min, 312 nm, t1=4.3 min, t2=6.0 min (major)].

Scheme 4a provides a specific procedure that was used to prepare the 2-amino-4-(methanesulfonylamino-methyl)-thiophene-3-sulfonic acid amide intermediate.

Scheme 4a

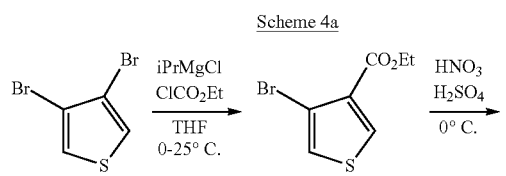
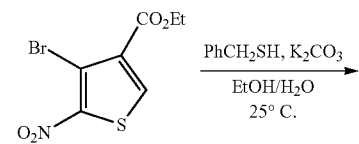
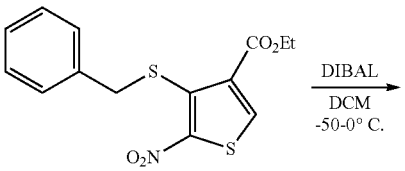
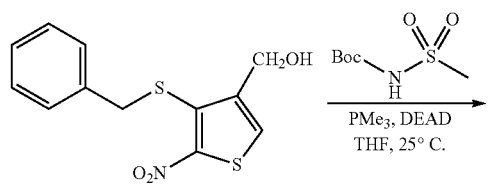
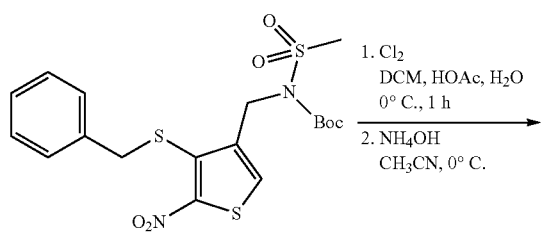

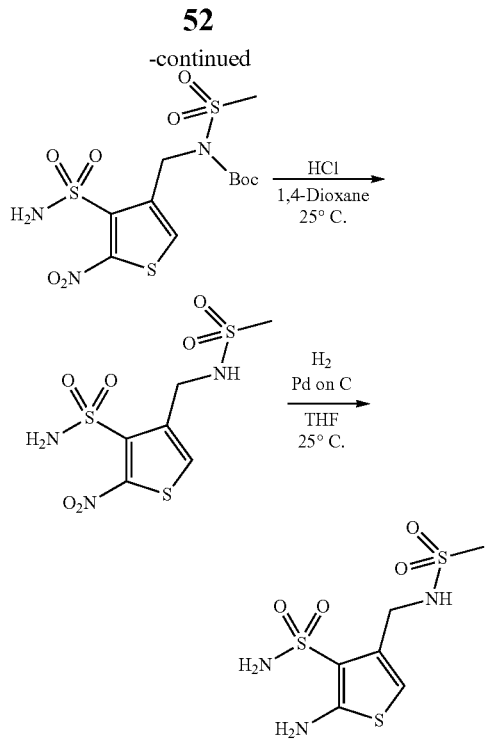

Scheme 4b provides a specific procedure that was used to prepare the 5,6-dihydro-1H-pyridin-2-one compound of Example 8.

Scheme 4b

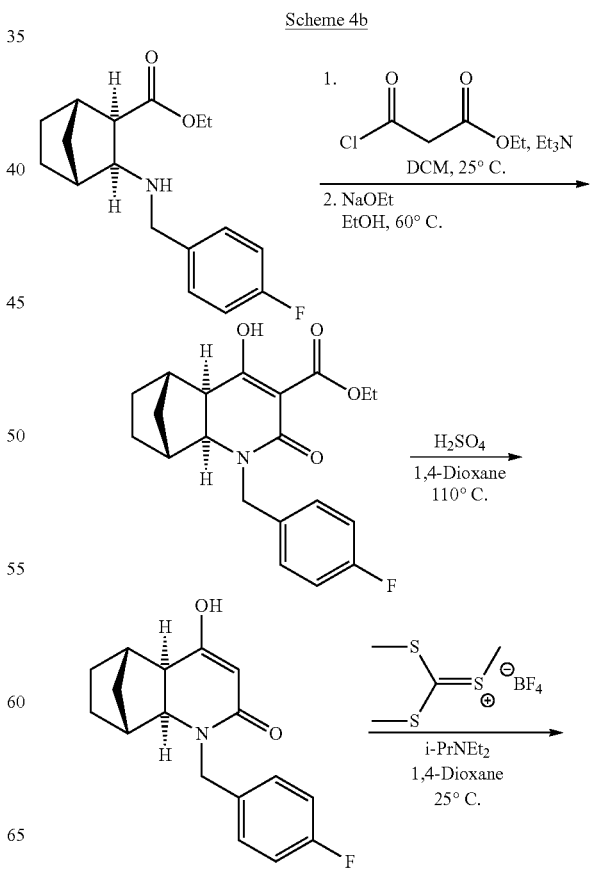

53

-continued

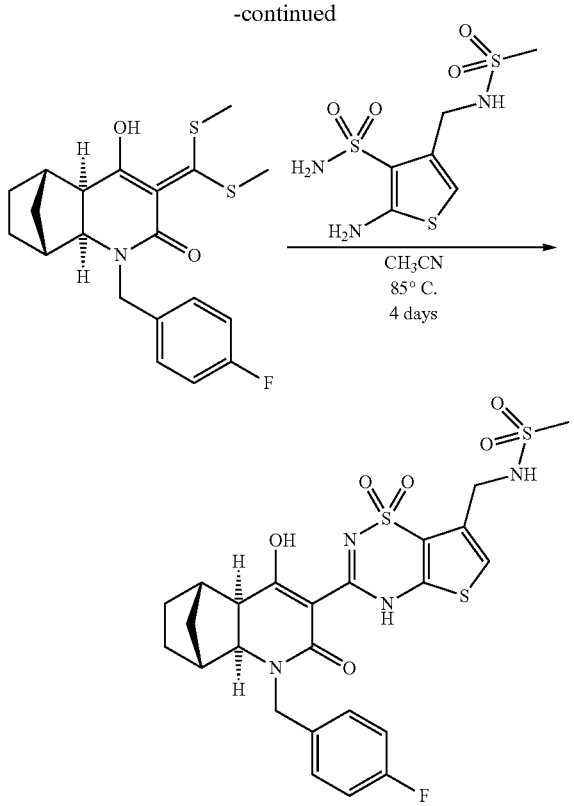

Example 8

(1R,2S,7R,8S)—N-{3-[3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-thieno[2,3-e][1,2,4]thiadiazin-7-ylmethyl}-methanesulfonamide

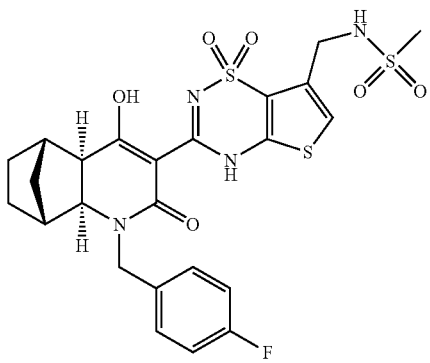 [SMILES: CS(=O)(=O)NCc1csc2c1S(=O)(=O)N=C(C1=C(O)[C@@H]3[C@H]4CC[C@H](C4)[C@@H]3N(Cc3ccc(F)cc3)C1=O)N2]

a) 4-Bromo-thiophene-3-carboxylic acid ethyl ester

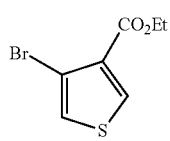 [SMILES: CCOC(=O)c1cscc1Br]

54

Isopropylmagnesium chloride (263 mL of a 2.0 M solution in tetrahydrofuran, 0.527 mol) was added via cannula over 35 min to a solution of 3,4-dibromo-thiophene (102 g, 0.421 mol) in tetrahydrofuran (600 mL) at 0° C. The mixture was allowed to warm to 25° C. and was stirred at that temperature for 18 h. Water (25 mL) was added, and the mixture was stirred at 25° C. for 15 min, and then was concentrated in vacuo to ~200 mL volume. The concentrate was partitioned between 1.0 M aqueous hydrochloric acid solution (400 mL) and ethyl acetate (2×350 mL). The combined organic layers were dried over sodium sulfate, filtered and were concentrated in vacuo to afford the crude product, 4-bromo-thiophene-3-carboxylic acid ethyl ester (91.9 g, 0.391 mol, 93%), as a yellow/brown oil. $^1$H NMR (400 MHz, CDCl$_3$) δ: 1.40 (3H, t, J=7.5 Hz), 4.36 (2H, q, J=7.3 Hz), 7.31 (1H, d, J=3.9 Hz), 8.10 (1H, d, J=3.0 Hz).

b) 4-Bromo-5-nitro-thiophene-3-carboxylic acid ethyl ester

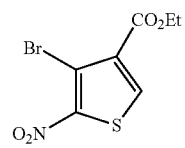 [SMILES: CCOC(=O)c1csc([N+](=O)[O-])c1Br]

4-Bromo-thiophene-3-carboxylic acid ethyl ester (97.6 g, 0.415 mol) was added over 10 min via pipette to 18.0 M sulfuric acid (660 mL) at 0° C. After stirring 5 min at 0° C., fuming nitric acid (18 mL) dissolved in 18.0 M sulfuric acid (130 mL) was added via addition funnel over 30 min. After the addition was completed, the reaction mixture was stirred for 5 min at 0° C., and then was poured onto ice (3.5 kg). The resulting precipitate was collected by filtration and was washed sequentially with water (300 mL), 10% aqueous sodium bicarbonate solution (400 mL) and water (300 mL). The brown/yellow solid thus obtained was dried in a vacuum oven overnight at 40° C. to afford the crude product, 4-bromo-5-nitro-thiophene-3-carboxylic acid ethyl ester (97.9 g, 0.350 mol, 84%). This material was further purified by flash column chromatography (Merck silica gel 60, 40-63 µm; 25% hexanes in dichloromethane) in 20 g portions prior to use in the next step (recovery=80-90%). $^1$H NMR (400 MHz, DMSO-d$_6$) δ: 1.31 (3H, t, J=7.0 Hz), 4.30 (4H, q, J=7.0 Hz), 8.68 (1H, s).

c) 4-Benzylsulfanyl-5-nitro-thiophene-3-carboxylic acid ethyl ester

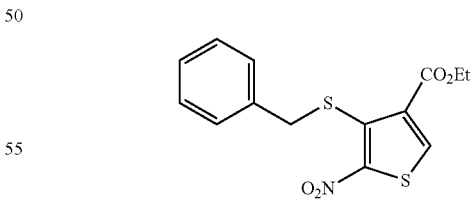

An aqueous solution of potassium carbonate (9.90 g, 71.6 mmol, dissolved in 40 mL water) was added to a suspension of 4-bromo-5-nitro-thiophene-3-carboxylic acid ethyl ester (20.06 g, 71.6 mmol) in ethanol at 25° C. Benzyl mercaptan (8.41 mL, 71.6 mmol) was added via pipette, and the dark red reaction mixture was stirred at 25° C. for 4 h and then concentrated in vacuo to near-dryness. The remaining orange-brown solid was triturated with water (200 mL) and was collected by filtration. After washing with water (200 mL), the resulting solid was air-dried overnight to afford the desired product, 4-benzylsulfanyl-5-nitro-thiophene-3-carboxylic acid ethyl ester (22.63 g, 70.0 mmol, 98%), as a yellow/brown solid. $^1$H NMR (400 MHz, CDCl$_3$) δ: 1.41 (3H, t, J=7.1 Hz), 4.25 (2H, s), 4.39 (2H, q, J=7.0 Hz), 7.18-7.23 (5H, m), 8.07 (1H, s).

d) (4-Benzylsulfanyl-5-nitro-thiophen-3-yl)-methanol

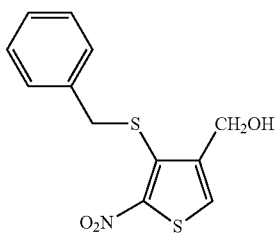 [SMILES: O=[N+]([O-])c1scc(CO)c1SCc1ccccc1]

Diisobutylaluminum hydride (154 mL of a 1.0 M solution in dichloromethane, 154 mmol) was added via cannula over 25 min to a solution of 4-benzylsulfanyl-5-nitro-thiophene-3-carboxylic acid ethyl ester (22.63 g, 70.0 mmol) at −50° C. The reaction mixture was stirred at −50° C. for 2 h, then was warmed to 0° C. and was maintained at that temperature for 35 min Water (200 mL) was added via addition funnel over 15 min and the resulting suspension was warmed to 25° C. whereupon additional water (200 mL) and D/L-tartaric acid (20 g) were added. After stirring vigorously at 25° C. for 30 min, the reaction mixture was partitioned between 1.0 M aqueous hydrochloric acid solution (300 mL) and dichloromethane (2×400 mL). The combined organic layers were dried over sodium sulfate, filtered and were concentrated in vacuo. Purification of the residue by flash column chromatography (Merck silica gel 60, 40-63 μm; 10-50% ethyl acetate in hexanes) afforded the desired product, (4-benzylsulfanyl-5-nitro-thiophen-3-yl)-methanol (10.52 g, 37.4 mmol, 53%), as a dark brown oil. $^1$H NMR (400 MHz, CDCl$_3$) δ: 4.21 (2H, s), 4.40 (2H, s), 7.09-7.12 (1H, m), 7.21-7.24 (4H, m), 7.39 (1H, s).

e) Boc-N-(4-Benzylsulfanyl-5-nitro-thiophen-3-ylmethyl)-methanesulfonamide

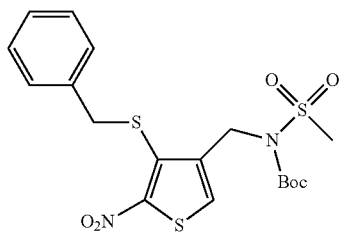 [SMILES: CC(C)(C)OC(=O)N(Cc1csc([N+](=O)[O-])c1SCc1ccccc1)S(C)(=O)=O]

Triethylamine (22.0 mL, 158 mmol), di-tert-butyl dicarbonate (27.5 g, 126 mmol), and 4-(N,N-dimethylamino)pyridine (1.28 g, 10.5 mmol) were added sequentially to a solution of methanesulfonamide (10.0 g, 105 mmol) in dichloromethane (300 mL) at 25° C. The mixture was stirred at 25° C. for 2 h, and then was concentrated in vacuo to ~40 mL volume. Ethyl acetate (350 mL) was added and the mixture was washed with 1.0 M aqueous hydrochloric acid solution (300 mL). The aqueous layer was extracted with ethyl acetate (250 mL) and the combined organic layers were dried over sodium sulfate, filtered and were concentrated in vacuo to afford Boc-N-methanesulfonamide (17.1 g, 87.6 mmol, 83%) as a white solid. $^1$H NMR (400 MHz, CDCl$_3$) δ: 1.53 (9H, s), 3.27 (3H, s).

Boc-N-methanesulfonamide (11.0 g, 56.3 mmol), trimethylphosphine (56.1 mL of a 1.0 M solution in tetrahydrofuran, 56.1 mmol), and a 40 wt. % solution of diethyl azodicarboxylate in toluene (25.6 mL, 56.0 mmol) were added sequentially to a solution of (4-benzylsulfanyl-5-nitro-thiophen-3-yl)-methanol (10.52 g, 37.4 mmol) in tetrahydrofuran (300 mL) at 25° C. The mixture was stirred for 3.5 h at 25° C., and then was concentrated in vacuo. Purification of the residue by flash column chromatography (Merck silica gel 60, 40-63 μm; 20% ethyl acetate in hexanes) afforded the desired product, Boc-N-(4-benzylsulfanyl-5-nitro-thiophen-3-ylmethyl)-methanesulfonamide (9.79 g, 21.3 mmol, 57%), as a dark brown oil. $^1$H NMR (400 MHz, CDCl$_3$) δ: 1.50 (9H, s), 3.29 (3H, s), 4.19 (2H, s), 4.68 (2H, s), 7.15-7.18 (2H, m), 7.22-7.25 (3H, m), 7.40 (1H, s).

f) Boc-4-(Methanesulfonylamino-methyl)-2-nitro-thiophene-3-sulfonic acid amide

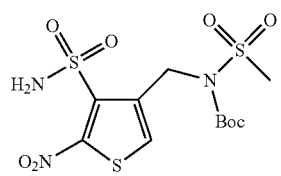

Boc-N-(4-Benzylsulfanyl-5-nitro-thiophen-3-ylmethyl)-methanesulfonamide (4.90 g, 10.7 mmol) was dissolved in dichloromethane (65 mL) and the dark brown solution was cooled to 0° C. A mixture of glacial acetic acid (15 mL) and water (20 mL) was then added slowly, producing a biphasic mixture. Chlorine gas was bubbled through this mixture at 0° C. for 5 min using a pipette. The resulting yellow biphasic mixture was stirred at 0° C. for an additional 35 min, then was poured into a separatory funnel and the layers separated. The aqueous layer was extracted with dichloromethane (1×50 mL) and the combined organic layers were washed with water (1×50 mL), dried over sodium sulfate, filtered and concentrated in vacuo to ~25 mL volume. Heptane (80 mL) was then added to this solution via addition funnel over 30 min. The resulting orange precipitate was collected by filtration, washed with heptane (2×20 mL), and air-dried to afford Boc-4-(methanesulfonylamino-methyl)-2-nitro-thiophene-3-sulfonyl chloride (2.45 g, 5.63 mmol, 53%).

Concentrated aqueous ammonium hydroxide solution (3 mL) was added to a solution of Boc-4-(methanesulfonylamino-methyl)-2-nitro-thiophene-3-sulfonyl chloride (3.30 g, 7.59 mmol) in acetonitrile (90 mL) at 0° C. The mixture was stirred at 0° C. for 45 min, and then was partitioned between half-saturated aqueous sodium bicarbonate solution (150 mL) and ethyl acetate (2×150 mL). The combined organic layers were dried over sodium sulfate, filtered and were concentrated in vacuo. Purification of the residue by flash column chromatography (Teledyne Isco RediSep column; 20-90% ethyl acetate in hexanes) afforded the desired product, Boc-4-(methanesulfonylamino-methyl)-2-nitro-thiophene-3-sulfonic acid amide (2.64 g, 6.35 mmol, 84%), as a yellow solid. $^1$H NMR (400 MHz, CDCl$_3$) δ: 1.54 (9H, s), 3.35 (3H, s), 5.12 (2H, s), 5.81 (2H, bs), 7.61 (1H, s).

g) 4-(Methanesulfonylamino-methyl)-2-nitro-thiophene-3-sulfonic acid amide

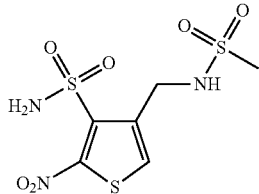 [SMILES: CS(=O)(=O)NCc1csc([N+](=O)[O-])c1S(N)(=O)=O]

Hydrogen chloride (20 mL of a 4.0 M solution in 1,4-dioxane) was added to a solution of Boc-4-(methanesulfonylamino-methyl)-2-nitro-thiophene-3-sulfonic acid amide (0.600 g, 1.44 mmol) in 1,4-dioxane (10 mL) at 25° C. The mixture was stirred at 25° C. for 18 h, and then was partitioned between half-saturated aqueous sodium bicarbonate solution (150 mL) and ethyl acetate (2×150 mL). The combined organic layers were dried over sodium sulfate, filtered and were concentrated in vacuo. Purification of the residue by flash column chromatography (Teledyne Isco RediSep column; 60-100% ethyl acetate in hexanes) provided a yellow oil. This material was triturated with dichloromethane to afford a yellow solid that was collected by filtration to afford the desired product, 4-(methanesulfonylamino-methyl)-2-nitro-thiophene-3-sulfonic acid amide (0.400 g, 1.27 mmol, 88%). $^1$H NMR (400 MHz, DMSO-$d_6$) δ: 2.96 (3H, s), 3.31 (2H, s), 4.35 (1H, d, J=5.4 Hz), 7.61 (1H, t, J=6.2 Hz), 7.85 (1H, s), 7.87 (2H, bs).

h) 2-Amino-4-(methanesulfonylamino-methyl)-thiophene-3-sulfonic acid amide

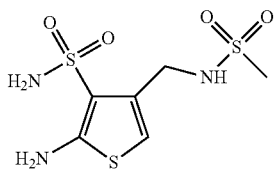

Palladium on carbon (10%, 0.150 g, dry) was added to a solution of 4-(methanesulfonylamino-methyl)-2-nitro-thiophene-3-sulfonic acid amide (0.156 g, 0.495 mmol) in tetrahydrofuran (12 mL) at 25° C. The flask was degassed and backfilled with hydrogen gas via balloon and the mixture was stirred under a positive pressure of hydrogen (2 balloons) for 17 h. The mixture was then filtered through Celite and the Celite was washed with tetrahydrofuran (3×20 mL). The combined filtrate and washings were concentrated in vacuo to afford the crude product, 2-amino-4-(methanesulfonylamino-methyl)-thiophene-3-sulfonic acid amide, as a yellow oil. This material was used in subsequent synthetic transformations without additional purification.

i) (1R,2S,7R,8S)-3-(4-Fluoro-benzyl)-6-hydroxy-4-oxo-3-aza-tricyclo[6.2.1.0$^{2,7}$]undec-5-ene-5-carboxylic acid ethyl ester

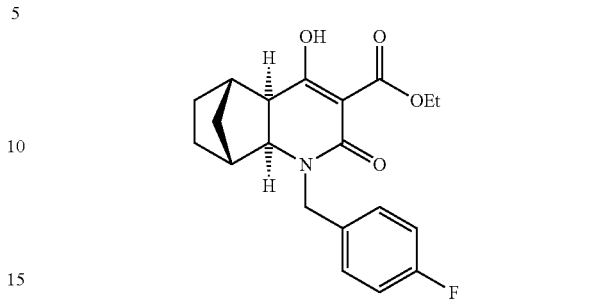

Triethylamine (4.22 mL, 30.3 mmol) and ethyl malonyl chloride (1.91 mL, 15.2 mmol) were added sequentially to a solution of (1S,2R,3S,4R)-3-(4-fluorobenzylamino)-bicyclo[2.2.1]heptane-2-carboxylic acid ethyl ester (prepared as described in Example 21, 4.21 g, 14.4 mmol) in dichloromethane at 25° C. The mixture was stirred at 25° C. for 1 h, and then was partitioned between 1.0 M aqueous hydrochloric acid solution (150 mL) and ethyl acetate (2×150 mL). The combined organic layers were dried over sodium sulfate, filtered and were concentrated in vacuo to afford a yellow/orange oil.

This material was dissolved in absolute ethanol (80 mL) at 25° C. and a 21 wt. % solution of sodium ethoxide in ethanol (14.0 mL, 43.2 mmol) was added. The mixture was heated to 60° C. for 45 min, and then was allowed to cool to 25° C. The mixture was then concentrated in vacuo and the resulting orange/brown solid was partitioned between 1.0 M aqueous hydrochloric acid solution (150 mL) and ethyl acetate (2×150 mL). The combined organic layers were dried over sodium sulfate, filtered and were concentrated in vacuo. Purification of the residue by flash column chromatography (Teledyne Isco RediSep column; 10-80% ethyl acetate in hexanes) afforded the desired product, (1R,2S,7R,8S)-3-(4-fluoro-benzyl)-6-hydroxy-4-oxo-3-aza-tricyclo[6.2.1.0$^{2,7}$]undec-5-ene-5-carboxylic acid ethyl ester, as a pale yellow oil. This material was used directly in the next synthetic step.

q) (1R,2S,7R,8S)-3-(4-Fluoro-benzyl)-6-hydroxy-3-aza-tricyclo[6.2.1.0$^{2,7}$]undec-5-en-4-one

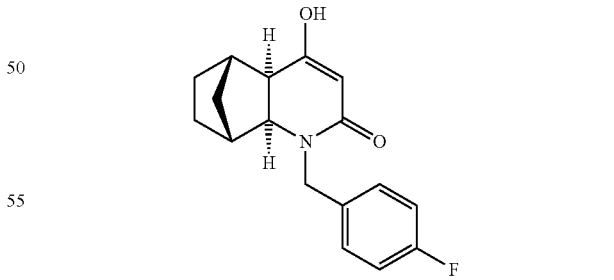

(1R,2S,7R,8S)-3-(4-Fluoro-benzyl)-6-hydroxy-4-oxo-3-aza-tricyclo[6.2.1.0$^{2,7}$]undec-5-ene-5-carboxylic acid ethyl ester was suspended in a 1/1 mixture of 1,4-dioxane and 1.0 M aqueous sulfuric acid solution (200 mL). The mixture was heated to 110° C. for 40 min, and then was allowed to cool to 25° C. The cooled mixture was poured into a separatory funnel and was extracted with ethyl acetate (2×150 mL). The combined organic layers were dried over sodium sulfate, filtered and were concentrated in vacuo to afford a white solid. This material was triturated with hexanes and was collected by filtration, washed with hexanes (2×15 mL) and air-dried to afford the desired product, (1R,2S,7R,8S)-3-(4-fluoro-benzyl)-6-hydroxy-3-aza-tricyclo[6.2.1.0$^{2,7}$]undec-5-en-4-one (2.24 g, 7.80 mmol, 54% over three steps), as a white solid. $^1$H NMR (major tautomer, 400 MHz, CDCl$_3$) δ: 1.11-1.16 (1H, m), 1.20-1.39 (3H, m), 1.57-1.69 (2H, m), 2.53 (1H, d, J=8.4 Hz), 2.63 (1H, bs), 2.73 (1H, bs), 3.39 (1H, d, J=4.1 Hz), 3.51 (1H, d, J=9.5 Hz), 4.29 (1H, d, J=14.9 Hz), 5.20 (1H, d, J=14.9 Hz), 6.98-7.04 (2H, m), 7.19-7.24 (2H, m).

r) (1R,2S,7R,8S)—N-{3-[3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-yl-methyl}-methanesulfonamide

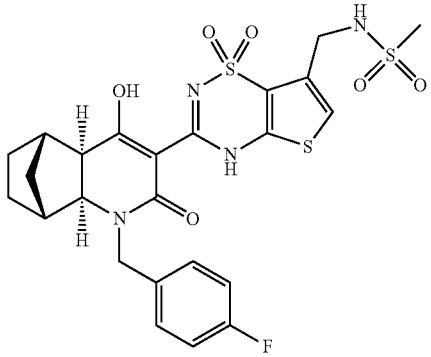 [SMILES: CS(=O)(=O)NCc1csc2c1S(=O)(=O)N=C(C1=C(O)[C@@H]3[C@H]4CC[C@H](C4)[C@@H]3N(Cc3ccc(F)cc3)C1=O)N2]

N,N-Diisopropylethylamine (0.974 mL, 5.59 mL) and (bis-methylsulfanyl-methylene)-methyl-sulfonium tetrafluoro borate salt (prepared as described in WO 2008/011337, 0.466 g, 1.94 mmol) were added sequentially to a solution of (1R,2S,7R,8S)-3-(4-fluoro-benzyl)-6-hydroxy-3-aza-tricyclo[6.2.1.0$^{2,7}$]undec-5-en-4-one (0.197 g, 0.686 mmol) in 1,4-dioxane (50 mL) at 25° C. The orange mixture was stirred at 25° C. for 2 h, and then was partitioned between water (100 mL) and ethyl acetate (2×100 mL). The combined organic layers were dried over sodium sulfate, filtered and were concentrated in vacuo to afford an orange oil.

This material was dissolved in acetonitrile (8 mL) and was added to a solution of crude 2-amino-4-(methanesulfonylamino-methyl)-thiophene-3-sulfonic acid amide (described above; Example 8 h, 0.495 mmol) in acetonitrile (4 mL) at 85° C. The mixture was maintained at 85° C. for 4 days, then was allowed to cool to 25° C. and was concentrated in vacuo. The residue was purified by prep-HPLC [Column Thomson ODS-A 100 Å 5μ, 150×21.2 mm, 30%-100% in 11.5 min @ 22 mL/min flow rate, 0.05% trifluoroacetic acid in acetonitrile/0.05% trifluoroacetic acid in water] to afford the crude product. Purification of this material by flash column chromatography (Teledyne Isco RediSep column; 50-100% ethyl acetate in hexanes) afforded the desired product, (1R,2S,7R,8S)—N-{3-[3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-thieno[2,3-e][1,2,4]thiadiazin-7-ylmethyl}-methanesulfonamide (0.060 g, 0.103 mmol, 21%), as an off-white solid. $^1$H NMR (400 MHz, DMSO-d$_6$) δ: 0.84-0.90 (1H, m), 1.08-1.60 (5H, m), 1.99 (1H, s), 2.61 (1H, bs), 2.96 (3H, s), 3.50 (1H, d, J=9.4 Hz), 3.96-3.99 (1H, m), 4.24 (1H, d, J=5.7 Hz), 4.38 (1H, d, J=14.8 Hz), 4.93 (1H, d, J=15.7 Hz), 7.11-7.16 (2H, m), 7.27 (1H, s), 7.29-7.33 (2H, m), 7.65 (1H, t, J=5.9 Hz). LC-MS (ESI) calculated for C$_{24}$H$_{25}$FN$_4$O$_6$S$_3$ 580.09. found 581.1 [M+H$^+$].

Example 9

N-{3-[(2S,7R)-3-(4-Fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide

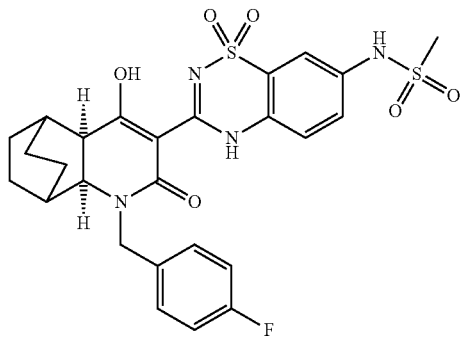

a) 4-Oxa-tricyclo[5.2.2.0$^{2,6}$]undecane-3,5-dione

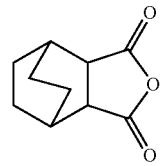 [SMILES: O=C1OC(=O)C2C3CCC(CC3)C12]

4-Oxa-tricyclo[5.2.2.0$^{2,6}$]undec-8-ene-3,5-dione (4.00 g, 22.45 mmol) was dissolved in ethyl acetate (100 mL). 10% Palladium on carbon (400 mg) was added. The flask was degassed and backfilled with hydrogen gas via balloon. The mixture was stirred at 25° C. for 16 h. The mixture was passed through a plug of Celite and the filtrate was concentrated in vacuo to afford a thick clear oil. Purification by flash column chromatography (Teledyne Isco RediSep column; 0 to 30% ethyl acetate in hexanes) afforded the desired product, 4-oxa-tricyclo[5.2.2.0$^{2,6}$]undecane-3,5-dione (2.92 g, 16.20 mmol, 72%), as a white powder. $^1$H NMR (400 MHz, DMSO-d$_6$) δ: 1.55-1.64 (6H, m), 1.76 (2H, d, J=9.2 Hz), 2.25 (2H, s), 3.11 (2H, s). LC-MS (ESI) calcd for C$_{10}$H$_{12}$O$_3$ 180.20. found 181.0 [M+H$^+$].

b) (2S,3R)-Bicyclo[2.2.2]octane-2,3-dicarboxylic acid monomethyl ester

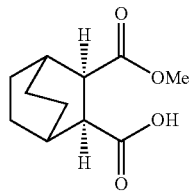 [SMILES: COC(=O)[C@@H]1C2CCC(CC2)[C@@H]1C(=O)O]

4-Oxa-tricyclo[5.2.2.0$^{2,6}$]undec-3,5-dione (0.90 g, 4.99 mmol) was dissolved in toluene (50 mL) and carbon tetrachloride (50 mL). Quinine (1.78 g, 5.49 mmol) was added and the mixture was cooled to −55° C. Methanol (0.61 mL, 14.97 mmol) was added dropwise to the above mixture. The reaction was stirred at −55° C. for 18 h. The reaction was warmed to 25° C. and concentrated in vacuo. The crude material was dissolved in ethyl acetate (50 mL) and washed with 1.0 M aqueous hydrochloric acid solution (2×40 mL). The organic layer was further washed with saturated aqueous brine solution (20 mL), dried over magnesium sulfate, filtered, and concentrated in vacuo to afford a clear oil. Purification by flash column chromatography (Teledyne Isco RediSep column; 0 to 50% ethyl acetate in hexanes) afforded the desired product, (2S,3R)-bicyclo[2.2.2]octane-2,3-dicarboxylic acid monomethyl ester (1.10 g, 5.18 mmol, 92%), as a clear oil. $^1$H NMR (400 MHz, DMSO-$d_6$) δ: 1.31 (2H, dd, $J_1$=20.0 Hz, $J_2$=12.4 Hz), 1.52-1.54 (4H, m), 1.63 (1H, t, J=10.4 Hz), 1.75 (1H, t, J=9.6 Hz), 1.87 (2H, bs), 2.84 (2H, dd, $J_1$=29.6 Hz, $J_2$=10.8 Hz), 3.52 (3H, s), 12.01 (1H, s). LC-MS (ESI) calcd for $C_{11}H_{16}O_4$ 212.24. found 213.1 [M+H$^+$].

c) (2R,3S)-3-Benzyloxycarbonylamino-bicyclo[2.2.2]octane-2-carboxylic acid methyl ester

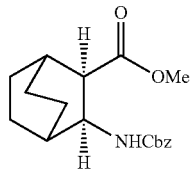 [SMILES: COC(=O)[C@@H]1C2CCC(CC2)[C@@H]1NC(=O)OCc1ccccc1]

(2S,3R)-Bicyclo[2.2.2]octane-2,3-dicarboxylic acid monomethyl ester (1.01 g, 4.76 mmol) was dissolved in anhydrous tetrahydrofuran (20 mL). The flask was degassed and backfilled with nitrogen and the mixture was cooled to 0° C. Triethylamine (1.99 mL, 14.28 mmol) was added followed by the dropwise addition of ethyl chloroformate (0.91 mL, 9.52 mmol) with vigorous stiffing. The mixture was stirred at 0° C. for 1 h. Sodium azide (0.93 g, 14.28 mmol) was dissolved in water (5 mL) and added to the reaction mixture at 0° C. The mixture was stirred at 0° C. for 5 min. The ice bath was removed. The mixture was warmed to 25° C. and was stirred for 2 h. The mixture was poured into water (50 mL) and the product extracted into ethyl acetate (50 mL). The organic layer was further washed with half-saturated aqueous sodium bicarbonate solution (2×20 mL), saturated aqueous brine solution (20 mL), dried over magnesium sulfate, filtered, and concentrated in vacuo to afford a clear oil. The oil was dissolved in anhydrous benzene (10 mL) and refluxed while stirring under nitrogen for 2 h. Upon cooling to 25° C. the solution was concentrated in vacuo to afford a slightly yellow oil. The oil was dissolved in dichloromethane (10 mL) and benzyl alcohol (0.54 mL, 5.24 mmol) was added followed by triethylamine (1.33 mL, 9.52 mmol). The mixture was refluxed under nitrogen for 16 h. Upon cooling to 25° C. the solution was concentrated in vacuo to afford a golden oil. Purification by flash column chromatography (Teledyne Isco RediSep column; 0 to 20% ethyl acetate in hexanes) afforded the desired product, (2R,3S)-3-benzyloxycarbonylamino-bicyclo[2.2.2]octane-2-carboxylic acid methyl ester (0.58 g, 1.83 mmol, 38%), as a clear oil. $^1$H NMR (400 MHz, CDCl$_3$) δ: 1.18-1.28 (2H, m), 1.42-1.50 (5H, m), 1.73-1.96 (3H, m), 2.88 (1H, d, $J_1$=5.6 Hz), 3.27 (1H, s), 3.42 (3H, s), 4.00-4.04 (1H, m), 4.97 (2H, dd, $J_1$=46.4 Hz, $J_2$=12.8 Hz), 7.06 (1H, d, J=9.6 Hz), 7.24-7.34 (4H, m). LC-MS (ESI) calcd for $C_{18}H_{23}NO_4$ 317.38. found 317.9 [M+H$^+$].

d) (2R,3S)-3-Amino-bicyclo[2.2.2]octane-2-carboxylic acid methyl ester hydrochloride

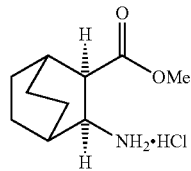

(2R,3S)-3-Benzyloxycarbonylamino-bicyclo[2.2.2]octane-2-carboxylic acid methyl ester (0.57 g, 1.79 mmol) was dissolved in ethyl acetate (20 mL). 10% Palladium on carbon (60 mg) was added. The flask was degassed and backfilled with hydrogen gas via balloon. The mixture was stirred at 25° C. for 16 h. The mixture was passed through a plug of Celite and the filtrate was concentrated in vacuo to afford a thick clear oil. The oil was dissolved in diethyl ether (6 mL) and added dropwise with vigorous stirring to a mixture of 4.0 M solution of hydrochloric acid in 1,4-dioxane (1.02 mL) and diethyl ether (10 mL). The desired product began to precipitate as a white solid. The mixture was stirred for 20 min. The precipitate was collected by vacuum filtration and washed with additional diethyl ether (5 mL). The solid was further dried in vacuo for 1 h to afford the desired product, (2R,3S)-3-amino-bicyclo[2,2,2]octane-2-carboxylic acid methyl ester hydrochloride (0.33 g, 1.50 mmol, 84%), as a white powder. $^1$H NMR (400 MHz, DMSO-$d_6$) δ: 1.38 (2H, dd, $J_1$=21.2 Hz, $J_2$=13.6 Hz), 1.55-1.63 (5H, m), 1.76-1.89 (3H, m), 3.02 (1H, dd, $J_1$=10.0 Hz, $J_2$=2.4 Hz), 3.47 (1H, bs), 3.65 (3H, s), 7.97 (3H, s). LC-MS (ESI) calcd for $C_{10}H_{17}NO_2$ (free amine) 183.25. found 184.2 [M+H$^+$].

e) (2R,3S)-3-(4-Fluoro-benzylamino)-bicyclo[2.2.2]octane-2-carboxylic acid methyl ester

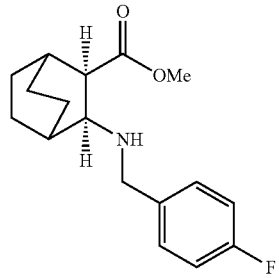 [SMILES: COC(=O)[C@@H]1C2CCC(CC2)[C@@H]1NCc1ccc(F)cc1]

(2R,3S)-3-Amino-bicyclo[2,2,2]octane-2-carboxylic acid methyl ester hydrochloride (0.34 g, 1.54 mmol) was dissolved in methanol (10 mL). Sodium acetate (0.25 g, 3.08 mmol) was added followed by 4 Å powdered molecular sieves (0.34 g) and 4-fluoro-benzaldehyde (0.16 mL, 1.54 mmol). Sodium cyanoborohydride (0.19 g, 3.08 mmol) was added and the mixture was stirred at 25° C. for 16 h. The mixture was poured into a mixture of saturated aqueous sodium bicarbonate solution (20 mL) and ethyl acetate (30 mL). After shaking, both layers were passed through a plug of Celite. The organic layer was further washed with saturated aqueous sodium bicarbonate solution (10 mL), saturated aqueous brine solution (10 mL), dried over magnesium sulfate, filtered, and concentrated in vacuo to afford the crude product, (2R,3S)-3-(4-fluoro-benzylamino)-bicyclo[2,2,2]octane-2-carboxylic acid methyl ester (0.32 g, 1.11 mmol, 72%), as a clear oil. LC-MS (ESI) calcd for $C_{17}H_{22}FNO_2$ 291.36. found 292.2 [M+H$^+$].

f) N-{3-[(2S,7R)-3-(4-Fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide

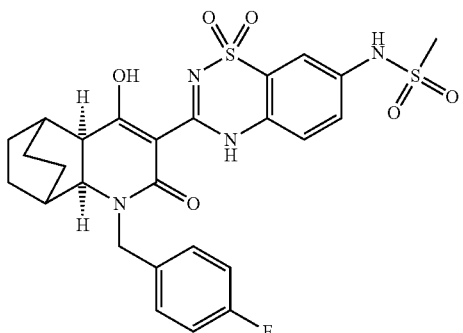

(2R,3S)-3-(4-Fluoro-benzylamino)-bicyclo[2,2,2]octane-2-carboxylic acid methyl ester (93 mg, 0.32 mmol) was dissolved in anhydrous N,N-dimethylformamide (4 mL). (7-Methanesulfonylamino-1,1-dioxo-1,4-dihydro-1λ$^6$-benzo[1,2,4]thiadiazin-3-yl)-acetic acid (prepared as described in U.S. Pat. No. 7,939,524 B2, 107 mg, 0.32 mmol) was added followed by N-methylmorpholine (74 mL, 0.67 mmol). The mixture was stirred until everything dissolved, approximately 5 min 1-(3-Dimethylaminopropyl)-3-ethylcarbodiimide hydrochloride (65 mg, 0.34 mmol) was added and the mixture was stirred at 25° C. for 16 h. The reaction was quenched via addition of saturated aqueous sodium bicarbonate solution (20 mL). The mixture was extracted with ethyl acetate (3×30 mL). The combined organic layers were washed with saturated aqueous brine solution (20 mL), dried over magnesium sulfate, filtered, and concentrated in vacuo to afford a golden oil. The oil was dissolved in ethanol (5 mL). A 21 wt. % solution of sodium ethoxide in ethanol (0.36 mL, 0.96 mmol) was added. The reaction was refluxed for 16 h. The reaction was quenched via the addition of 1.0 M aqueous hydrochloric acid solution (10 mL). The mixture was extracted with ethyl acetate (3×20 mL). The organic layer was further washed with saturated sodium bicarbonate solution (2×20 mL), saturated aqueous brine solution (20 mL), dried over magnesium sulfate, filtered, and concentrated in vacuo to afford a clear oil. Purification by flash column chromatography (Teledyne Isco RediSep column; 0 to 20% ethyl acetate in dichloromethane) afforded the desired product, N-{3-[(2S,7R)-3-(4-fluoro-benzyl)-6-hydroxy-4-oxo-3-aza-tricyclo[6.2.2.0$^{2,7}$]dodec-5-en-5-yl]-1,1-dioxo-1,4-dihydro-1λ$^6$-benzo[1,2,4]thiadiazin-7-yl}-methanesulfonamide (0.11 g, 0.19 mmol, 59%), as a white powder. $^1$H NMR (400 MHz, DMSO-d$_6$) δ: 1.39 (2H, d, J=8.0 Hz), 1.54-1.59 (8H, m), 1.91 (1H, s), 2.14 (1H, s), 3.06 (3H, s), 3.75 (1H, d, J=11.6 Hz), 4.28 (1H, d, J=15.2 Hz), 5.03 (1H, d, J=15.6 Hz), 7.13-7.17 (2H, m), 7.34-7.37 (2H, m), 7.50-7.60 (3H, m), 10.18 (1H, s). LC-MS (ESI) calcd for C$_{26}$H$_{27}$FN$_4$O$_6$S$_2$ 574.64. found 575.1 [M+H$^+$]. m.p.: 203.8-205.7° C. ee=94.4% [HPLC-analysis: Chiralpak AS-RH 4.6×250 mm, 5 micron, 0.8 mL/min, 310 nm].

Example 10

N-{3-[(1S,2S,7R,8R)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

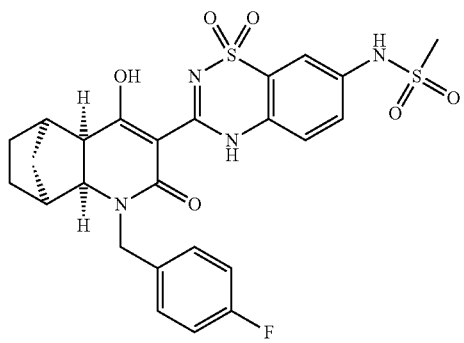

a) (1R,2S,3R,4S)-3-(Methoxycarbonyl)bicyclo[2.2.1]hept-5-ene-2-carboxylic acid

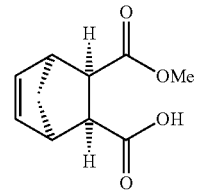

The starting material (a) was prepared as described in J. Org. Chem. 2000, 65, 6984-6991. cis-5-Norbornene-endo-2,3-dicarboxylic anhydride (4.104 g, 25 mmol) was suspended in a 1:1 mixture of toluene and carbon tetrachloride (500 mL). The mixture was stirred for 20 min Quinine (8.92 g, 27.5 mmol) was added and the flask was degassed and backfilled with nitrogen. The solution was cooled to −55° C. While stirring, methanol (3.04 mL, 75 mmol) was added. The mixture was stirred at −55° C. for 20 h. Upon warming to 25° C., the mixture was concentrated in vacuo to a thick oil. The oil was dissolved in ethyl acetate (400 mL), washed with 1.0 M aqueous hydrochloric acid solution (2×400 mL), saturated aqueous brine solution (100 mL), dried over magnesium sulfate, filtered, and concentrated in vacuo to afford the desired product, (1R,2S,3R,4S)-3-(methoxycarbonyl)bicyclo[2.2.1]hept-5-ene-2-carboxylic acid (4.8 g, 24.5 mmol, 98%), as a clear waxy solid. $^1$H NMR (400 MHz, DMSO-d$_6$) δ: 1.26 (1H, d, J=8.5 Hz), 1.33 (1H, d, J=8.8 Hz), 3.00 (1H, s), 3.03 (1H, s), 3.21-3.30 (2H, m), 3.45 (3H, s), 6.02-6.04 (1H, m), 6.14-6.16 (1H, m), 11.86 (1H, s).

b) Methyl (1S,2R,3S,4R)-3-{[(benzyloxy)carbonyl]amino}bicyclo[2.2.1]hept-5-ene-2-carboxylate

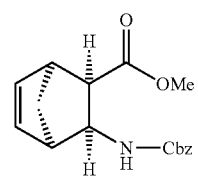

(1R,2S,3R,4S)-3-(Methoxycarbonyl)bicyclo[2.2.1]hept-5-ene-2-carboxylic acid (4.61 g, 23.5 mmol) was dissolved in anhydrous tetrahydrofuran (40 mL). The flask was degassed and backfilled with nitrogen and the mixture was cooled to 0° C. Triethylamine (9.9 mL, 70.5 mmol) was added followed by the dropwise addition of ethyl chloroformate (4.48 mL, 47 mmol) with vigorous stirring. Immediate precipitation was observed. Additional tetrahydrofuran (60 mL) was added. The mixture was stirred at 0° C. for 1 h. Sodium azide (4.58 g, 70.5 mmol) was dissolved in water (30 mL) and added to the reaction mixture at 0° C. The mixture was stirred at 0° C. for 5 min. The ice bath was removed. The mixture was warmed to 25° C. and was stirred for 2 h. The mixture was poured into water (300 mL) and the product extracted into ethyl acetate (300 mL). The organic layer was further washed with half-saturated aqueous sodium bicarbonate solution (2×100 mL), saturated aqueous brine solution (100 mL), dried over magnesium sulfate, filtered, and concentrated in vacuo to afford a clear oil. The oil was dissolved in anhydrous benzene (50 mL) and refluxed while stirring under nitrogen for 2 h. Upon cooling to 25° C. the solution was concentrated in vacuo to afford a slightly yellow oil. The oil was dissolved in dichloromethane (30 mL) and benzyl alcohol (2.68 mL, 25.9 mmol) was added followed by triethylamine (6.61 mL, 47 mmol). The mixture was refluxed under nitrogen for 16 h. Upon cooling to 25° C. the solution was concentrated in vacuo to afford a golden oil. Purification by flash column chromatography (Merck silica gel 60, 40-63 μm, 15% ethyl acetate in hexanes) afforded the desired product, methyl (1S,2R,3S,4R)-3-{[(benzyloxy)carbonyl]amino}bicyclo[2.2.1]hept-5-ene-2-carboxylate (5.51 g, 18.31 mmol, 78%), as a clear oil. $^1$H NMR (400 MHz, CDCl$_3$) δ: 1.38 (1H, d, J=9.1 Hz), 1.50 (1H, d, J=9.4 Hz), 3.10 (2H, s), 3.21 (1H, dd, J$_1$=9.2 Hz, J$_2$=2.3 Hz), 3.53 (3H, s), 4.62 (1H, dt, J$_1$=9.4 Hz, J$_2$=2.9 Hz), 5.07 (2H, q, J=13.0 Hz), 5.29 (1H, d, J=8.6 Hz), 6.15-6.17 (1H, m), 6.37-6.38 (1H, m), 7.29-7.35 (5H, m). LC-MS (ESI) calcd for C$_{17}$H$_{19}$NO$_4$ 301.13. found 258.1 (100%), 302.2 [M+H$^+$] (70%), 603.5 [2M+H$^+$] (20%).

c) Methyl (1R,2R,3S,4S)-3-aminobicyclo[2.2.1]heptane-2-carboxylate hydrochloride

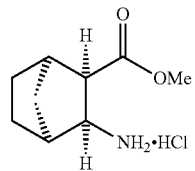

Methyl (1S,2R,3S,4R)-3-{[(benzyloxy)carbonyl]amino}bicyclo[2.2.1]hept-5-ene-2-carboxylate (5.5 g, 18.27 mmol) was dissolved in ethyl acetate (75 mL). 5% Palladium on carbon (650 mg) was added. The flask was degassed and backfilled with hydrogen gas via balloon. The mixture was stirred at 25° C. for 16 h. The mixture was passed through a plug of Celite and the filtrate was concentrated in vacuo to afford a thick clear oil. The oil was dissolved in ethyl acetate (15 mL) and added dropwise, with vigorous stirring, to a mixture of a 4.0 M solution of hydrochloric acid in 1,4-dioxane (10 mL, 40 mmol) in diethyl ether (90 mL). The desired product began to precipitate as a white solid. The mixture was stirred for 20 min. The precipitate was collected by vacuum filtration, and was washed with additional diethyl ether (15 mL). The solid was further dried in vacuo for 1 h to afford the desired product, methyl (1R,2R,3S,4S)-3-aminobicyclo[2.2.1]heptane-2-carboxylate hydrochloride (2.61 g, 12.69 mmol, 69%), as a white powder. $^1$H NMR (400 MHz, DMSO-d$_6$) δ: 1.34-1.43 (4H, m), 1.54 (1H, d, J=9.5 Hz), 1.68 (1H, d, J=11.4 Hz), 2.47-2.48 (2H, m), 3.03 (1H, dd, J$_1$=11.0 Hz, J$_2$=4.0 Hz), 3.49-3.53 (1H, m), 3.62 (3H, s), 8.07 (3H, bs). LC-MS (ESI) calcd for C$_9$H$_{15}$NO$_2$ (free amine) 169.11. found 170.1 [M+H$^+$] (100%), 339.2 [2M+H$^+$] (50%).

d) Methyl (1R,2R,3S,4S)-3-[(4-fluorobenzyl)amino]bicyclo[2.2.1]heptane-2-carboxylate

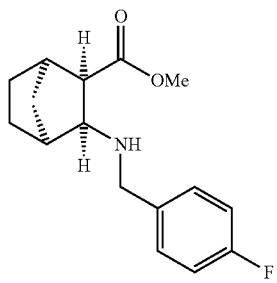

Methyl (1R,2R,3S,4S)-3-aminobicyclo[2.2.1]heptane-2-carboxylate hydrochloride (1 g, 4.86 mmol) was dissolved in methanol (23 mL). Sodium acetate (0.755 g, 9.2 mmol) was added followed by 4 Å powdered molecular sieves (1 g) and 4-fluoro-benzaldehyde (0.571 g, 4.6 mmol). Sodium cyanoborohydride (0.578 g, 9.2 mmol) was added and the mixture was stirred at 25° C. for 16 h. The mixture was poured into a mixture of saturated aqueous sodium bicarbonate solution (200 mL) and ethyl acetate (300 mL). After shaking, both layers were passed through a plug of Celite. The organic layer was further washed with saturated aqueous sodium bicarbonate solution (100 mL), saturated aqueous brine solution (100 mL), dried over magnesium sulfate, filtered, and concentrated in vacuo to afford the crude product, methyl (1R,2R,3S,4S)-3-[(4-fluorobenzyl)amino]bicyclo[2.2.1]heptane-2-carboxylate (1.172 g, 4.23 mmol, 92%), as a clear oil. LC-MS (ESI) calcd for C$_{16}$H$_{20}$FNO$_2$ 277.15. found 278.2 [M+H$^+$].

e) N-{3-[(1S,2S,7R,8R)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

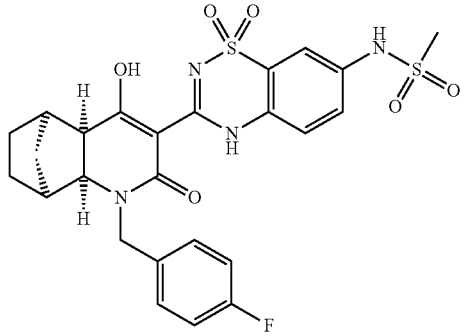

Methyl (1R,2R,3S,4S)-3-[(4-fluorobenzyl)amino]bicyclo[2.2.1]heptane-2-carboxylate (0.087 g, 0.3 mmol) was dissolved in anhydrous N,N-dimethylformamide (2.8 mL). (7-Methanesulfonylamino-1,1-dioxo-1,4-dihydro-1λ$^6$-benzo[1,2,4]thiadiazin-3-yl)-acetic acid (prepared as described in U.S. Pat. No. 7,939,524 B2, 0.1 g, 0.3 mmol) was added followed by N-methylmorpholine (0.07 mL, 0.63 mmol). The mixture was stirred until everything dissolved, approximately 5 min 1-(3-Dimethylaminopropyl)-3-ethyl-carbodiimide hydrochloride (0.061 g, 0.315 mmol) was added and the mixture was stirred at 25° C. for 4 h. Triethylamine (0.126 mL, 0.9 mmol) was added and the mixture was stirred at 50° C. for 16 h. Upon cooling to 25° C., the solution was diluted with ethyl acetate (25 mL) and washed with 1.0 M aqueous hydrochloric acid solution (2×25 mL), saturated aqueous brine solution (10 mL), dried over magnesium sulfate, filtered, and concentrated in vacuo to afford a golden oil. The oil was dissolved in methanol (4 mL) and the product was precipitated by the addition of 1.0 M aqueous hydrochloric acid solution (4 mL) while stirring. The solid was collected by vacuum filtration and further dried in vacuo to afford the desired product, N-{3-[(1S,2S,7R,8R)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide (0.0805 g, 0.144 mmol, 48%), as a white powder. $^1$H NMR (400 MHz, DMSO-d$_6$) δ: 1.23-1.48 (6H, m), 2.67-2.68 (2H, m), 3.06 (3H, s), 3.24 (1H, d, J=15.0 Hz), 3.72 (1H, d, J=11.9 Hz), 4.07 (1H, d, J=15.6 Hz), 5.12 (1H, d, J=15.7 Hz), 7.14 (2H, t, J=8.4 Hz), 7.39 (2H, dd, J$_1$=8.2 Hz, J$_2$=5.8 Hz), 7.51 (1H, dd, J$_1$=8.4 Hz, J$_2$=2.3 Hz), 7.57-7.60 (2H, m), 10.18 (1H, s). LC-MS (ESI) calcd for C$_{25}$H$_{25}$FN$_4$O$_6$S$_2$ 560.12. found 561.3 [M+H$^+$]. ee=99% [HPLC-analysis: Chiralpak AS-RH 4.6×250 mm, 5 micron at r.t., Solvent A-Solvent B (see table for gradient), 0.8 mL/min, 310 nm, t1=7.58 min (major), t2=10.08 min]

Example 11

N-{3-[(1R,2R,7S,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1$\lambda^6$-benzo[1,2,4]thiadiazin-7-yl}-methanesulfonamide

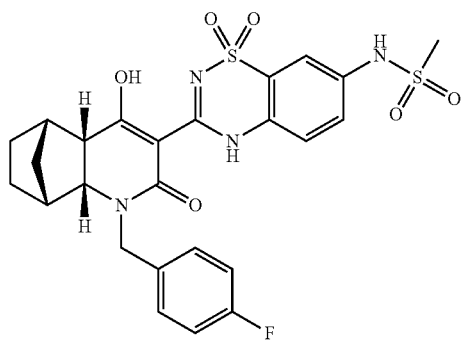 [SMILES: CS(=O)(=O)Nc1ccc2c(c1)S(=O)(=O)N=C(C1=C(O)[C@H]3[C@H]4CC[C@H](C4)[C@H]3N(Cc3ccc(F)cc3)C1=O)N2]

a) (1S,2R,3S,4R)-3-(Methoxycarbonyl)bicyclo[2.2.1]hept-5-ene-2-carboxylic acid

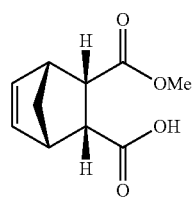 [SMILES: COC(=O)[C@@H]1[C@H](C(=O)O)[C@@H]2C=C[C@H]1C2]

The starting material (a) was prepared as described in *J. Org. Chem.* 2000, 65, 6984-6991. cis-5-Norbornene-endo-2,3-dicarboxylic anhydride (8.21 g, 50 mmol) was suspended in a 1:1 mixture of toluene and carbon tetrachloride (250 mL). The mixture was stirred for 10 min. Quinidine (17.84 g, 55 mmol) was added and the flask was degassed and backfilled with nitrogen. The solution was cooled to −55° C. While stifling, methanol (6.08 mL, 150 mmol) was added. The mixture was stirred at −55° C. for 18 h. Upon warming to 25° C., the mixture was concentrated in vacuo to a thick oil. The oil was dissolved in a mixture of ethyl acetate (400 mL) and 1.0 M aqueous hydrochloric acid solution (300 mL). After shaking, the layers were separated and the organic layer was further washed with 1.0 M aqueous hydrochloric acid solution (2×100 mL), saturated aqueous brine solution (100 mL), dried over magnesium sulfate, filtered, and concentrated in vacuo to afford the desired product, (1S,2R,3S,4R)-3-(methoxycarbonyl)bicyclo[2.2.1]hept-5-ene-2-carboxylic acid (9.15 g, 46.6 mmol, 94%), as a clear oil. $^1$H NMR (400 MHz, DMSO-d$_6$) δ: 1.26 (1H, d, J=8.4 Hz), 1.33 (1H, d, J=8.4 Hz), 3.00 (1H, s), 3.03 (1H, s), 3.21-3.29 (2H, m), 3.45 (3H, s), 6.02-6.04 (1H, m), 6.14-6.16 (1H, m), 11.86 (1H, s).

b) Methyl (1R,2S,3R,4S)-3-{[(benzyloxy)carbonyl]amino}bicyclo[2.2.1]hept-5-ene-2-carboxylate

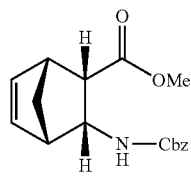 [SMILES: COC(=O)[C@@H]1[C@H](NC(=O)OCc2ccccc2)[C@@H]2C=C[C@H]1C2]

This intermediate was prepared as described in *Synthesis* 2001, 11, 1719-1730. (1S,2R,3S,4R)-3-(Methoxycarbonyl)bicyclo[2.2.1]hept-5-ene-2-carboxylic acid (8.94 g, 45.57 mmol) was dissolved in anhydrous tetrahydrofuran (200 mL). The flask was degassed and backfilled with nitrogen and the mixture was cooled to 0° C. Triethylamine (19.2 mL, 136.7 mmol) was added followed by the dropwise addition of ethyl chloroformate (8.69 mL, 91.1 mmol) with vigorous stirring. Immediate precipitation was observed. The mixture was stirred at 0° C. for 1 h. Sodium azide (8.89 g, 136.7 mmol) was dissolved in water (60 mL) and added to the reaction mixture at 0° C. The mixture was stirred at 0° C. for 1 h. The ice bath was removed. The mixture was warmed to 25° C. and continued to stir for 2 h. The mixture was poured into water (400 mL) and the product extracted into ethyl acetate (400 mL). The organic layer was further washed with half-saturated aqueous sodium bicarbonate solution (2×200 mL), saturated aqueous brine solution (2×200 mL), dried over magnesium sulfate, filtered, and concentrated in vacuo to afford a slightly brown oil. The oil was dissolved in anhydrous benzene (100 mL) and refluxed while stifling under nitrogen for 2 h. Upon cooling to 25° C. the solution was concentrated in vacuo to afford a slightly brown oil. The oil was dissolved in dichloromethane (60 mL) and benzyl alcohol (5.19 mL, 50.13 mmol) was added followed by triethylamine (12.81 mL, 91.14 mmol). The mixture was refluxed under nitrogen for 16 h. Upon cooling to 25° C. the solution was concentrated in vacuo to afford a golden oil. Purification by flash column chromatography (Merck silica gel 60, 40-63 μm, 10% ethyl acetate in hexanes) afforded the desired product, methyl (1R,2S,3R,4S)-3-{[(benzyloxy)carbonyl]amino}bicyclo[2.2.1]hept-5-ene-2-carboxylate (10.1 g, 33.55 mmol, 74%), as a clear oil. $^1$H NMR (400 MHz, CDCl$_3$) δ: 1.38 (1H, d, J=8.7 Hz), 1.50 (1H, d, J=8.4 Hz), 3.10 (2H, s), 3.21 (1H, d, J=8.8 Hz), 3.53 (3H, s), 4.59-4.64 (1H, m), 5.07 (2H, q, J=13.0 Hz), 5.29 (1H, d, J=8.3 Hz), 6.15-6.17 (1H, m), 6.37-6.38 (1H, m), 7.27-7.36 (5H, m). LC-MS (ESI) calcd for $C_{17}H_{19}NO_4$ 301.13, found 258.1 (100%), 302.2 [M+H$^+$] (70%), 603.5 [2M+H$^+$] (20%).

c) Methyl (1S,2S,3R,4R)-3-aminobicyclo[2.2.1]heptane-2-carboxylate hydrochloride

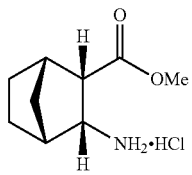

Methyl (1R,2S,3R,4S)-3-{[(benzyloxy)carbonyl]amino}bicyclo[2.2.1]hept-5-ene-2-carboxylate (10 g, 33.22 mmol) was dissolved in ethyl acetate (150 mL). 5% Palladium on carbon (1.5 mg) was added. The flask was degassed and backfilled with hydrogen gas via balloon. The mixture was stifled at 25° C. for 2 h. The mixture was passed through a plug of Celite and the filtrate was concentrated in vacuo to a volume of 50 mL. The solution was added dropwise, with vigorous stirring, to a mixture of 4.0 M hydrochloric acid solution in 1,4-dioxane (20 mL) in diethyl ether (200 mL). The desired product began to precipitate as a white solid. The mixture was stirred for 10 min. The precipitate was collected by vacuum filtration, washed with additional diethyl ether (15 mL). The solid was further dried in vacuo for 1 h to afford the desired product, methyl (1S,2S,3R,4R)-3-aminobicyclo[2.2.1]heptane-2-carboxylate hydrochloride (5.21 g, 25.33 mmol, 76.3%), as a white powder. $^1$H NMR (400 MHz, DMSO-d$_6$) δ: 1.33-1.42 (4H, m), 1.54 (1H, d, J=10.3 Hz), 1.69 (1H, d, J=11.5 Hz), 2.46-2.48 (2H, m), 3.03 (1H, dd, J$_1$=10.8 Hz, J$_2$=4.1 Hz), 3.46-3.55 (1H, m), 3.62 (3H, s), 8.09 (3H, bs). LC-MS (ESI) calcd for $C_9H_{15}NO_2$ (free amine) 169.11. found 170.1 [M+H$^+$] (100%), 339.2 [2M+H$^+$] (50%).

d) Methyl (1S,2S,3R,4R)-3-[(4-fluorobenzyl)amino]bicyclo[2.2.1]heptane-2-carboxylate

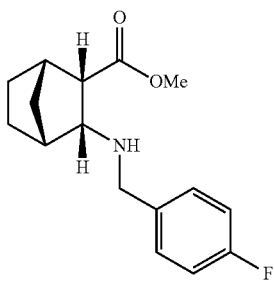 [SMILES: COC(=O)[C@H]1[C@H]2CC[C@H](C2)[C@H]1NCc1ccc(F)cc1]

Methyl (1S,2S,3R,4R)-3-aminobicyclo[2.2.1]heptane-2-carboxylate hydrochloride (1 g, 4.86 mmol) was dissolved in methanol (23 mL). Sodium acetate (0.755 g, 9.2 mmol) was added followed by 4 Å powdered molecular sieves (1 g) and 4-fluoro-benzaldehyde (0.571 g, 4.6 mmol). Sodium cyanoborohydride (0.578 g, 9.2 mmol) was added and the mixture was stirred at 25° C. for 16 h. The mixture was poured into a mixture of saturated aqueous sodium bicarbonate solution (200 mL) and ethyl acetate (300 mL). After shaking, both layers were passed through a plug of Celite. The organic layer was further washed with saturated aqueous sodium bicarbonate solution (100 mL), saturated aqueous brine solution (100 mL), dried over magnesium sulfate, filtered, and concentrated in vacuo to afford the crude product, methyl (1S,2S,3R,4R)-3-[(4-fluorobenzyl)amino]bicyclo[2.2.1]heptane-2-carboxylate (1.11 g, 4.0 mmol, 87%), as a clear oil. LC-MS (ESI) calcd for $C_{16}H_{20}FNO_2$ 277.15, found 278.2 [M+H$^+$].

e) N-{3-[(1R,2R,7S,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide

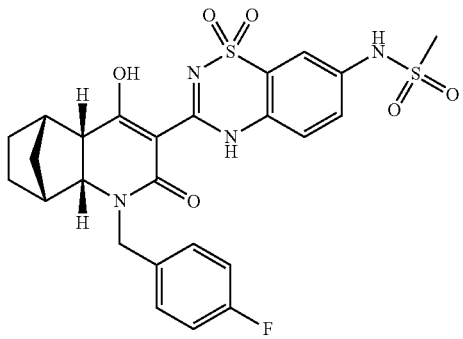 [SMILES: CS(=O)(=O)Nc1ccc2c(c1)S(=O)(=O)N=C(C1=C(O)[C@H]3[C@H]4CC[C@H](C4)[C@H]3N(Cc3ccc(F)cc3)C1=O)N2]

Methyl (1S,2S,3R,4R)-3-[(4-fluorobenzyl)amino]bicyclo[2.2.1]heptane-2-carboxylate (0.087 g, 0.3 mmol) was dissolved in anhydrous N,N-dimethylformamide (2.8 mL). (7-Methanesulfonylamino-1,1-dioxo-1,4-dihydro-1λ$^6$-benzo[1,2,4]thiadiazin-3-yl)-acetic acid (prepared as described in U.S. Pat. No. 7,939,524 B2, 0.1 g, 0.3 mmol) was added followed by N-methylmorpholine (0.07 mL, 0.63 mmol). The mixture was stirred until everything dissolved, approximately 5 min 1-(3-Dimethylaminopropyl)-3-ethylcarbodiimide hydrochloride (0.061 g, 0.315 mmol) was added and the mixture was stirred at 25° C. for 4 h. Triethylamine (0.126 mL, 0.9 mmol) was added and the mixture was stirred at 50° C. for 16 h. Upon cooling to 25° C., the solution was diluted with ethyl acetate (25 mL) and washed with 1.0 M aqueous hydrochloric acid solution (2×25 mL), saturated aqueous brine solution (10 mL), dried over magnesium sulfate, filtered, and concentrated in vacuo to afford a golden oil. The oil was dissolved in methanol (4 mL) and the product was precipitated by the addition of 1.0 M aqueous hydrochloric acid solution (4 mL) while stirring. The solid was collected by vacuum filtration and further dried in vacuo to afford the desired product, N-{3-[(1R,2R,7S,8S)-3-(4-fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide (0.0781 g, 0.139 mmol, 46%), as a white powder. $^1$H NMR (400 MHz, DMSO-d$_6$) δ: 1.23-1.48 (6H, m), 2.67-2.68 (2H, m), 3.06 (3H, s), 3.24 (1H, d, J=15.0 Hz), 3.72 (1H, d, J=11.9 Hz), 4.07 (1H, d, J=15.6 Hz), 5.12 (1H, d, J=15.7 Hz), 7.14 (2H, t, J=8.4 Hz), 7.39 (2H, dd, J$_1$=8.2 Hz, J$_2$=5.8 Hz), 7.51 (1H, dd, J$_1$=8.4 Hz, J$_2$=2.3 Hz), 7.57-7.60 (2H, m), 10.18 (1H, s). LC-MS (ESI) calcd for $C_{25}H_{25}FN_4O_6S_2$ 560.12. found 561.3 [M+H$^+$]. ee=99% [HPLC-analysis: Chiralpak AS-RH 4.6×250 mm, 5 micron at r.t., Solvent A-Solvent B (see table for gradient), 0.8 mL/min, 310 nm, t1=7.58 min, t2=10.08 min (major)].

Biological Testing

The ability of Formula I compounds to reduce serum uric acid levels in a patient was demonstrated in a Phase I study of healthy subjects. Six patients were administered a single 800 mg oral dose of N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7- yl}-methanesulfonamide (the compound of Example 2) while two patients received a matching placebo. Significant unexpected decreases (24-40%) in uric acid from the baseline to the end of the trial were found in all patients receiving the compound (see Table 1).

TABLE 1

| Subject No. | Age/Gender | | Screen | Predose | 4 hr | 24 hr | 48 hr | 144 hr |
|---|---|---|---|---|---|---|---|---|
| 1 | 38/M | | 5.1 | 5.3 | 5.0 | 3.4 | 3.3 | 4.6 |
| 2 | 33/F | | 2.9 | 2.8 | 2.9 | 1.6 | 1.8 | 2.8 |
| 3 | 53/M | | 6.3 | 5.0 | 5.0 | 2.8 | 3.4 | 5.3 |
| 4 | 32/M | P | 5.1 | 4.3 | 4.3 | 4.7 | 4.7 | 6.0 |
| 5 | 41/F | | 4.9 | 4.8 | 4.9 | 2.4 | 2.3 | 4.3 |
| 6 | 28/F | P | 3.5 | 3.4 | 3.4 | 3.8 | 3.3 | 4.3 |
| 7 | 25/M | | 6.2 | 6.2 | 6.2 | 4.6 | 4.5 | 5.8 |
| 8 | 35/M | | 5.9 | 6.4 | 5.5 | 4.9 | 4.3 | 5.8 |

Uric Acid (mg/dL)
P = Placebo

Inhibition of Uric Acid Uptake

Uric Acid (UA) is the end product of purine metabolism in humans. It is secreted into the urine and 90% of it is reabsorbed into the blood stream. Screening lead compounds for the inhibition of URAT1 evaluates their potential to decrease UA reabsorption thus decreasing UA blood levels which might be beneficial to certain patient populations.

The $EC_{50}$ values of the inhibition of uric acid uptake were measured. Human Embryonic Kidney (HEK293) cells expressing URAT1 (HEK293 cells transfected with vectors containing human URAT1 cDNA) and control cells (HEK293 cells transfected with only vectors) were used. Prior to the experiments, cells were cultured in 75-cm² bottom flasks and subjected to passage every 3 or 4 days. The control cells and URAT1 expressing cells were seeded in Collagen I coated 24 well plates at a density of 1 to 4×10⁵ cells/well, and incubated in a $CO_2$ incubator (37° C. and 5% $CO_2$) for 1 to 3 days to prepare cell monolayers for the determination of the cellular transport activity (cleared volume).

The $EC_{50}$ values of the inhibition of UA uptake into HEK293 cells facilitated by URAT1 expressed in the cells range from ~0.5 μM to 14.8 μM for the compounds of Examples 1-11 tested. Under the same conditions, the $EC_{50}$ of benzbromarone, the positive control URAT1 inhibitor, is <0.1 μM.

What is claimed is:

1. A method for lowering serum uric acid in a patient comprising administering to the patient a therapeutically effective amount of a compound of Formula I

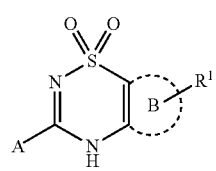

wherein
Ring B is

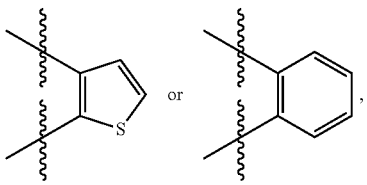 [SMILES: *c1ccsc1* ; *c1ccccc1*]

A is

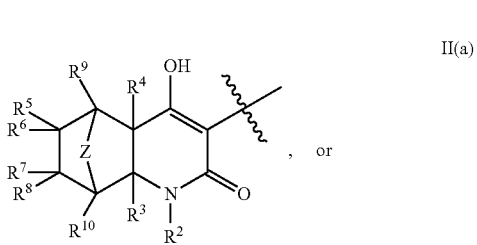

Z is $-(CR^{11}R^{12})_n-$,
Y is $-(CR^{13}R^{14})_m-$,
n is 1 or 2,
m is 2 or 3,
$R^1$ is H, $-NH_2$, or $-(CH_2)_q-NH-S(O)_2CH_3$, wherein q is 0 or 1,
$R^2$ is $C_1$-$C_6$ alkyl, $C_3$-$C_6$ cycloalkyl, aryl, or $-(CH_2)-R^{15}$, wherein $R^{15}$ is

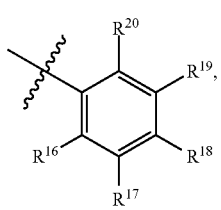

wherein $R^{16}$, $R^{17}$, $R^{18}$, $R^{19}$ and $R^{20}$ are independently H, $C_1$-$C_6$ alkyl, hydroxy, or halo, $R^3$, $R^4$, $R^5$, $R^6$, $R^7$, $R^8$, $R^9$, $R^{10}$, $R^{11}$, $R^{12}$, $R^{13}$, and $R^{14}$ are independently H or $C_1$-$C_6$ alkyl, wherein each alkyl, cycloalkyl, or aryl are optionally substituted by one or more alkyl, hydroxyl, or halo substituents,
or a pharmaceutically acceptable salt, hydrate, solvate, tautomer or stereoisomer thereof.

2. The method of claim 1 wherein Ring B is

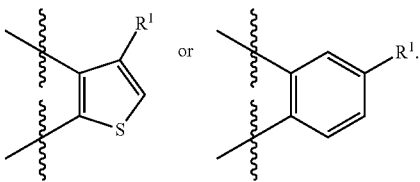

3. The method of claim 1 wherein q is 1 and Ring B is

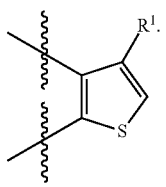

4. The method of claim 1 where A is

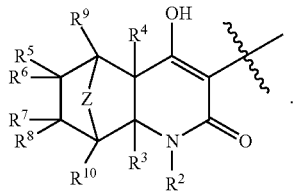

II(a)

5. The method of claim 1 wherein $R^1$ is H.

6. The method of claim 1 wherein $R^2$ is —(CH$_2$)—$R^{15}$ and $R^{15}$ is selected from

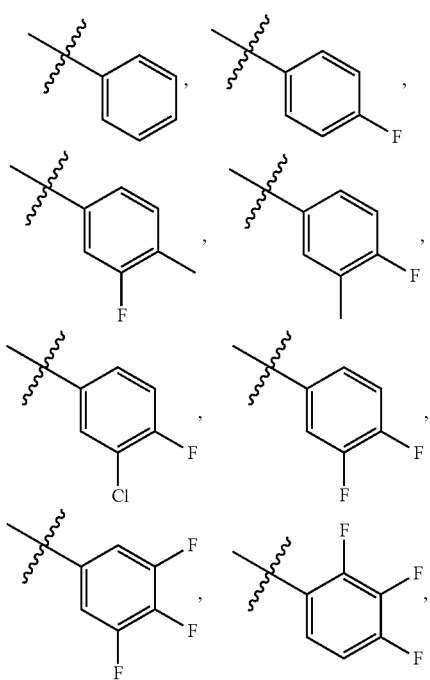

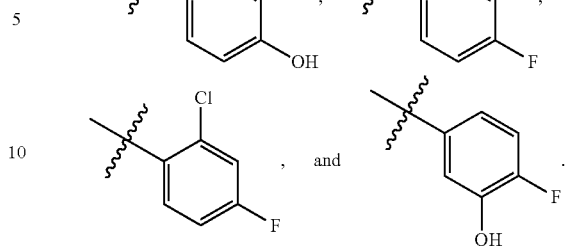

7. The method of claim 1 wherein q is 0.
8. The method of claim 1 wherein n is 1.
9. The method of claim 1 wherein q is 0 and n is 1.
10. The method of claim 1 wherein $R^3$, $R^4$, $R^5$, $R^6$, $R^7$, $R^8$, $R^9$, $R^{10}$, $R^{11}$, $R^{12}$, $R^{13}$, and $R^{14}$ are H.
11. The method of claim 1 wherein $R^{16}$, $R^{17}$, $R^{18}$, $R^{19}$, and $R^{20}$ are independently H, methyl, or halo.
12. The method of claim 1 wherein $R^{16}$, $R^{17}$, $R^{18}$, $R^{19}$, and $R^{20}$ are independently H or halo.
13. The method of claim 1 wherein $R^{18}$ is fluoro and $R^{16}$, $R^{17}$, $R^{19}$, and $R^{20}$ are H.
14. The method of claim 1 wherein
q is 0 and n is 1,
$R^3$, $R^4$, $R^5$, $R_6$, $R^7$, $R^8$, $R^9$, $R^{10}$, $R^{11}$, $R^{12}$, $R^{13}$, and $R^{14}$ are H, and
$R^{16}$, $R^{17}$, $R^{18}$, $R^{19}$, and $R^{20}$ are independently H or halo.
15. The method of claim 1 wherein the patient is a human.
16. The method of claim 1 further comprising administering an additional therapeutic agent to the patient.
17. A method for lowering serum uric acid in a patient in need thereof comprising administrating to said patient a therapeutically effective amount of a compound or pharmaceutically acceptable salt thereof selected from N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-ylmethyl}-methanesulfonamide, N-{3-[(1R,2S,7R,8S)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide, (1R,2S,7R,8S)-5-(1,1-Dioxo-1,4-dihydro-1λ$^6$-benzo[1,2,4]thiadiazin-3-yl)-3-(4-fluoro-benzyl)-6-hydroxy-3-aza-tricyclo[6.2.1.0$^{2,7}$]undec-5-en-4-one, (4aR,7aS)—N-{3-[1-(4-Fluoro-benzyl)-4-hydroxy-2-oxo-2,4-a,5,6,7,7a-hexahydro-1H-[1]pyrindin-3-yl]-1,1-dioxo-1,4-dihydro-1λ$^6$-benzo[1,2,4]thiadiazin-7-yl}-methanesulfonamide, N-[3-(1R,2S,7R,8S)-3-Cyclopentyl-6-hydroxy-4-oxo-3-aza-tricyclo[6.2.1.0$^{2,7}$]undec-5-en-5-yl)-1,1-dioxo-1,4-dihydro-1λ$^6$-benzo[1,2,4]thiadiazin-7-yl]-methanesulfonamide, (1R,2S,7R,8S)-5-(7-Amino-1,1-dioxo-1,4-dihydro-1λ$^6$-benzo[1,2,4]thiadiazin-3-yl)-3-(4-fluoro-benzyl)-6-hydroxy-3-aza-tricyclo[6.2.1.0$^{2,7}$]undec-5-en-4-one, N-{3-[(1S,2R,7S,8R)-3-(4-Fluoro-benzyl)-6-hydroxy-4-oxo-3-aza-tricyclo[6.2.1.0$^{2,7}$]undec-5-en-5-yl]-1,1-dioxo-1,4-dihydro-1λ$^6$-benzo[1,2,4]thiadiazin-7-yl}-methanesulfonamide, (1R,2S,7R,8S)—N-{3-[3-(4-Fluoro-benzyl)-6-hydroxy-4-oxo-3-aza-tricyclo[6.2.1.0$^{2,7}$]undec-5-en-5-yl]-1,1- dioxo-1,4-dihydro-1λ⁶-thieno[2,3-e][1,2,4]thiadiazin-7-ylmethyl}-methanesulfonamide, N-{3-[(2S,7R)-3-(4-Fluoro-benzyl)-6-hydroxy-4-oxo-3-aza-tricyclo[6.2.2.0²,⁷]dodec-5-en-5-yl]-1,1-dioxo-1,4-dihydro-1λ⁶-benzo[1,2,4]thiadiazin-7-yl}-methanesulfonamide, N-{3-[(1S,2S,7R,8R)-3-(4-Fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-yl}-methanesulfonamide, and N-{3-[(1R,2R,7S,8S)-3-(4-Fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-yl}methanesulfonamide.

18. The method of claim 17 wherein said compound is N-{3-[(1R,2S,7R,8S)-3-(4-Fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-yl}-methanesulfonamide.

19. A method for treating or preventing hyperuricemia, gout, urinary urolithiasis, a reperfusion disease, or renal dysfunction, such as tumor-lysis syndrome, hypertension, or cardiovascular disease in a patient in need thereof, comprising administering to the patient a therapeutically effective amount of a Formula I compound according to claim 1, or a pharmaceutically acceptable salt thereof.

20. The method of claim 19 for treating or preventing gout.

21. The method of claim 19 wherein the compound or pharmaceutically acceptable salt thereof is selected from N-{3-[(1R,2S,7R,8S)-3-(4-Fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-ylmethyl}-methanesulfonamide, N-{3-[(1R,2S,7R,8S)-3-(4-Fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-yl}-methanesulfonamide, (1R,2S,7R,8S)-5-(1,1-Dioxo-1,4-dihydro-1λ⁶-benzo[1,2,4]thiadiazin-3-yl)-3-(4-fluoro-benzyl)-6-hydroxy-3-aza-tricyclo[6.2.1.0²,⁷]undec-5-en-4-one, (4aR,7aS)—N-{3-[1-(4-Fluoro-benzyl)-4-hydroxy-2-oxo-2,4-a,5,6,7,7a-hexahydro-1H-[1]pyrindin-3-yl]-1,1-dioxo-1,4-dihydro-1λ⁶-benzo[1,2,4]thiadiazin-7-yl}-methanesulfonamide, N-[3-(1R,2S,7R,8S)-3-Cyclopentyl-6-hydroxy-4-oxo-3-aza-tricyclo[6.2.1.0²,⁷]undec-5-en-5-yl)-1,1-dioxo-1,4-dihydro-1λ⁶-benzo[1,2,4]thiadiazin-7-yl]-methanesulfonamide, (1R,2S,7R,8S)-5-(7-Amino-1,1-dioxo-1,4-dihydro-1λ⁶-benzo[1,2,4]thiadiazin-3-yl)-3-(4-fluoro-benzyl)-6-hydroxy-3-aza-tricyclo[6.2.1.0²,⁷]undec-5-en-4-one, N-{3-[(1S,2R,7S,8R)-3-(4-Fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-yl}-methanesulfonamide, (1R,2S,7R,8S)—N-{3-[3-(4-Fluoro-benzyl)-6-hydroxy-4-oxo-3-aza-tricyclo[6.2.1.0²,⁷]undec-5-en-5-yl]-1,1-dioxo-1,4-dihydro-1λ⁶-thieno[2,3-e][1,2,4]thiadiazin-7-ylmethyl}-methanesulfonamide, N-{3-[(2S,7R)-3-(4-Fluoro-benzyl)-6-hydroxy-4-oxo-3-aza-tricyclo[6.2.2.0²,⁷]undec-5-en-5-yl]-1,1-dioxo-1,4-dihydro-1λ⁶-benzo[1,2,4]thiadiazin-7-yl}-methanesulfonamide, N-{3-[(1S,2S,7R,8R)-3-(4-Fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-yl}-methanesulfonamide, and N-{3-[(1R,2R,7S,8S)-3-(4-Fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-yl}-methanesulfonamide.

22. The method of claim 19 wherein the compound is N-{3-[(1R,2S,7R,8S)-3-(4-Fluoro-benzyl)-6-hydroxy-4-oxo-3-aza-tricyclo[6.2.1.0²,⁷]undec-5-en-5-yl]-1,1-dioxo-1,4-dihydro-1λ⁶-benzo[1,2,4]thiadiazin-7-yl}-methanesulfonamide.

\* \* \* \* \*